US008686004B2

(12) United States Patent
Bretschneider et al.

(10) Patent No.: US 8,686,004 B2
(45) Date of Patent: Apr. 1, 2014

(54) HETEROCYCLIC COMPOUNDS AS PESTICIDES

(75) Inventors: Thomas Bretschneider, Lohmar (DE); Reiner Fischer, Monheim (DE); Martin Füβlein, Düsseldorf (DE); Peter Jeschke, Bergisch Gladbach (DE); Adeline Köhler, Wuppertal (DE); Joachim Kluth, Langenfeld (DE); Friedrich August Mühlthau, Bad Soden am Taunus (DE); Yoshitaka Sato, Ibaraki (JP); Arnd Voerste, Köln (DE); Eiichi Shimojo, Oyama (JP)

(73) Assignee: Bayer CropScience AG, Monheim (DE)

( * ) Notice: Subject to any disclaimer, the term of this patent is extended or adjusted under 35 U.S.C. 154(b) by 69 days.

(21) Appl. No.: 13/171,030

(22) Filed: Jun. 28, 2011

(65) Prior Publication Data

US 2012/0165345 A1 Jun. 28, 2012

Related U.S. Application Data

(60) Provisional application No. 61/359,058, filed on Jun. 28, 2010.

(30) Foreign Application Priority Data

Jun. 28, 2010 (EP) .................................. 10167453
Mar. 24, 2011 (EP) .................................. 11159576

(51) Int. Cl.
*C07D 401/14* (2006.01)
*A01N 43/56* (2006.01)

(52) U.S. Cl.
USPC ........... 514/318; 514/333; 514/341; 514/342; 546/193; 546/256; 546/268.7; 546/269.7; 546/270.4

(58) Field of Classification Search
USPC ................. 546/193, 256, 268.7, 269.7, 270.4; 514/318, 333, 341, 342
See application file for complete search history.

(56) References Cited

U.S. PATENT DOCUMENTS

| 5,252,540 | A  | 10/1993 | Heistracher et al. |
| 6,265,411 | B1 | 7/2001  | Thomas et al. |
| 6,673,817 | B1 | 1/2004  | Zhu et al. |
| 8,252,723 | B2 | 8/2012  | Jakobi et al. |
| 8,513,260 | B2 | 8/2013  | Schwarz et al. |
| 8,536,204 | B2 | 9/2013  | Bretschneider et al. |
| 2004/0006143 | A1 | 1/2004 | Hattori et al. |
| 2004/0116744 | A1 | 6/2004 | Furuya et al. |
| 2004/0167334 | A1 | 8/2004 | Shermolovich et al. |
| 2008/0139627 | A1 | 6/2008 | Beckmann et al. |
| 2008/0318941 | A1 | 12/2008 | Dunn et al. |
| 2009/0076282 | A1 | 3/2009 | Toriyabe et al. |
| 2009/0111847 | A1 | 4/2009 | Li et al. |
| 2009/0247551 | A1 | 10/2009 | Jeschke et al. |
| 2009/0253749 | A1 | 10/2009 | Jeschke et al. |
| 2009/0312330 | A1 | 12/2009 | Mita et al. |
| 2009/0318694 | A1 | 12/2009 | Hamamoto et al. |
| 2010/0035935 | A1 | 2/2010 | Koyanagi et al. |
| 2010/0240705 | A1 | 9/2010 | Jeschke et al. |
| 2011/0098287 | A1 | 4/2011 | Bretschneider et al. |
| 2011/0166143 | A1 | 7/2011 | Bretschneider et al. |
| 2011/0190365 | A1 | 8/2011 | Werner et al. |
| 2011/0212949 | A1 | 9/2011 | Bretschneider et al. |
| 2011/0275583 | A1 | 11/2011 | Bretschneider et al. |
| 2011/0319428 | A1 | 12/2011 | Füβlein et al. |
| 2012/0094837 | A1 | 4/2012 | Mühlthau et al. |
| 2012/0095023 | A1 | 4/2012 | Bretschneider et al. |

FOREIGN PATENT DOCUMENTS

| CA | 2095967 | 11/1993 |
| CA | 2 671 179 A1 | 6/2008 |
| CA | 2 730 844 A1 | 1/2010 |
| DE | 100 14 006 A1 | 9/2001 |
| EP | 0 482 349 A2 | 4/1992 |
| EP | 0 539 588 A1 | 5/1993 |
| EP | 0 569 810 A1 | 11/1993 |
| EP | 2 107 060 A1 | 10/2009 |
| JP | 2008-110953 A | 5/2008 |
| JP | 2010-18586 A | 1/2010 |
| WO | WO 96/33270 A1 | 10/1996 |
| WO | WO 01/09098 A1 | 2/2001 |
| WO | WO 03/028458 A1 | 4/2003 |
| WO | WO 03/106457 A1 | 12/2003 |
| WO | WO 2004/099160 A1 | 11/2004 |
| WO | WO 2005/035486 A1 | 4/2005 |
| WO | WO 2005/058299 A1 | 6/2005 |
| WO | WO 2005/063094 A1 | 7/2005 |
| WO | WO 2006/002099 A2 | 1/2006 |
| WO | WO 2006/019831 A1 | 2/2006 |

(Continued)

OTHER PUBLICATIONS

Alvey, L., et al., "Diversity-oriented synthesis of furo[3,2-f]chromanes with antimycobacterial activity," *Eur. J. Med. Chem.* 44:2497-2505, Elsevier Masson SAS, France (2009).

Boal, B.W., et al., "An Interrupted Fischer Indolization Approach toward Fused Indoline-Containing Natural Products," *Org. Let.* 11(15):3458-3461, American Chemical Society, United States (2009).

Boger, D.L. and Panek, J.S., "Inverse Electron Demand Diels-Alder Reactions of Heterocyclic Azadienes: Formal Total Synthesis of Streptonigrin," *J. Am. Chem. Soc.* 107(20):5745-5754, American Chemical Society, United States (1985).

Bonnefous, C., et al., "Biphenyl-indanones: Allosteric potentiators of the metabotropic glutamate subtype 2 receptor," *Bioorg. Med. Chem. Lett.* 15:4354-4358, Elsevier Ltd., United States (2005).

Cristau, H.-J., et al., "Mild Conditions for Copper-Catalysed N-Arylation of Pyrazoles," *Eur. J. Org. Chem.*:695-709, Wiley-VCH Verlag GmbH & Co. KGaA, Germany (2004).

Groutas, W.C., et al., "Inhibition of Serine Proteases by Functionalized Sulfonamides Coupled to the 1,2,5-thiadiazolidin-3-one 1,1 Dioxide Scaffold," *Bioorg. Med. Chem.* 9:1543-1548, Elsevier Science Ltd., England (2001).

Hendrickse, T.F., et al., "Phosphoric-Carboxylic Imides. III. The Benzoylation of N-Methyldiethylphosphoramidate and Related Anions," *Phosphorus and Sulfur* 20:93-105, Gordon and Breach, Science Publishers, Inc., United States (1984).

(Continued)

*Primary Examiner* — Deepak Rao
(74) *Attorney, Agent, or Firm* — Sterne, Kessler, Goldstein & Fox P.L.L.C.

(57) ABSTRACT

The present application relates to novel heterocyclic compounds, to the use thereof for controlling animal pests, which include arthropods and especially insects, and to processes for preparing the novel compounds.

11 Claims, No Drawings

(56) References Cited

FOREIGN PATENT DOCUMENTS

| | | | |
|---|---|---|---|
| WO | WO 2006/056433 A2 | 6/2006 | |
| WO | WO 2006/100288 A2 | 9/2006 | |
| WO | WO 2007/024782 A2 | 3/2007 | |
| WO | WO 2007/027777 A2 | 3/2007 | |
| WO | WO 2007/045588 A1 | 4/2007 | |
| WO | WO 2007/057407 A2 | 5/2007 | |
| WO | WO 2007/075459 A2 | 7/2007 | |
| WO | WO 2007/083239 A1 | 7/2007 | |
| WO | WO 2007/103755 A2 | 9/2007 | |
| WO | WO 2007/114532 A1 | 10/2007 | |
| WO | WO 2007/132475 A1 | 11/2007 | |
| WO | WO 2007/149134 A1 | 12/2007 | |
| WO | WO 2008/104503 A1 | 9/2008 | |
| WO | WO 2008/154528 A2 | 12/2008 | |
| WO | WO 2009/049851 A1 | 4/2009 | |
| WO | WO 2009/143039 | * | 11/2009 |
| WO | WO 2010/005692 A2 | 1/2010 | |
| WO | WO 2010/006713 A2 | 1/2010 | |
| WO | WO 2010-074747 A1 | 7/2010 | |
| WO | WO 2010/074751 A1 | 7/2010 | |

OTHER PUBLICATIONS

Hrubiec, R.T., et al., "Synthesis and Evaluation of 2-Substituted 1-Methyl-1-(4-tolylsulfonyl)hydrazines as Antineoplastic Agents," *J. Med. Chem.* 29:1299-1301, American Chemical Society, United States (1986).

Khan, M.A. and Pinto, A.A.A., "Hetarylpyrazoles. II. (1) Reactions of Pyrazol-l'-ylpyridines," *J. Heterocycl. Chem.* 18:9-14, HeteroCorporation, United States (1981).

McDonald, I.M., et al., "Optimization of 1,3,4-Benzotriazepine-Based $CCK_2$ Antagonists to Obtain Potent, Orally Active Inhibitors of Gastrin-Mediated Gastric Acid Secretion," *J. Med. Chem.* 50:3101-3112, American Chemical Society, United States (2007).

Sondhi, S.M., et al., "Conventional and microwave assisted synthesis of small molecule based biologically active heterocyclic amidine derivatives," *European Journal of Medicinal Chemistry* 45(3):902-908, Elsevier Masson SAS, France (2009).

Suryakiran, N., et al., "Synthesis of 3-Amino-substituted *N*-Alkylindazoles via Palladium(II)-catalyzed Intramolecular N-Arylation of Tosylhydrazines," *Chemistry Letters* 36(11):1370-1371, The Chemical Society of Japan, Japan (2007).

Wu, X. and Hu, L., "Efficient Amidation from Carboxylic Acids and Azides via Selenocarboxylates: Application to the Coupling of Amino Acids and Peptides with Azides," *J. Org. Chem.* 72:765-774, American Chemical Society, United States (2007).

Zhu, X., et al., "2,4-Diaryl-4,6,7,8-tetrahydroquinazoin-5(1*H*)-one derivatives as anti-HBV agents targeting at capsid assembly," *Bioorg. Med. Chem. Lett.* 20:299-301, Elsevier Ltd., England (2009).

English Language Abstract of WIPO patent Publication No. WO 01/09098 A1, European Patent Office, espacenet database—Worldwide (2001).

English language Abstract of Japanese Patent Publication No. 2008-110953 A, Japanese Patent Office, Patent and Utility Model Gazette DB Patent Abstracts of Japan (2008).

English language Abstract of Japanese Patent Publication No. 2010-018586 A, Japanese Patent Office, Patent and Utility Model Gazette DB Patent Abstracts of Japan (2010).

International Search Report for International Application No. PCT/EP2011/060596, European Patent Office, Netherlands, mailed on Jan. 30, 2012.

Office Action mailed Sep. 28, 2012, in U.S. Appl. No. 12/902,878, inventors Bretschneider, T. et al., filed Oct. 12, 2010.

Office Action mailed Apr. 8, 2013, in U.S. Appl. No. 12/902,878, inventors Bretschneider, T. et al., filed Oct. 12, 2010.

Office Action mailed Jan. 1, 2013, U.S. Appl. No. 13/054,401, inventors Bretschneider, T. et al., filed May 17, 2011.

Office Action mailed Aug. 28, 2013, in U.S. Appl. No. 13/054,401, inventors Bretschneider, T. et al., filed May 17, 2011.

* cited by examiner

HETEROCYCLIC COMPOUNDS AS PESTICIDES

The present application relates to novel heterocyclic compounds, to processes for preparation thereof and to the use thereof for controlling animal pests, which include arthropods and especially insects, and also to intermediates for preparation of the heterocyclic compounds.

Particular thiazolyl, thiadiazolyl and pyrazolyl compounds have already become known as insecticidally active ingredients (cf. WO 2010/006713 A2).

Modern crop protection compositions have to meet many demands, for example in relation to the level, duration and breadth of their action and possible use. Questions of toxicity and of combinability with other active ingredients or formulation auxiliaries play a role, as does the question of the expense that the synthesis of an active ingredient requires. In addition, resistances can occur. For all these reasons, the search for novel crop protection compositions cannot be considered to be complete, and there is a constant need for novel compounds having properties which, compared to the known compounds, are improved at least in relation to individual aspects.

It was an object of the present invention to provide compounds which widen the spectrum of the pesticides in various respects.

This object, and further objects which are not stated explicitly but can be discerned or derived from the connections discussed herein, are achieved by novel compounds of the formula (I)

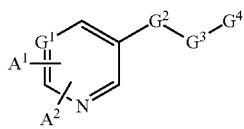
(I)

in which $A^1$ and $A^2$ are each independently hydrogen, halogen, cyano, nitro, alkyl, cycloalkyl or alkoxy, $G^1$ is N or C-$A^1$ and $G^2$ is a radical from the group of

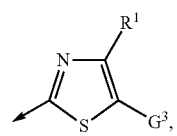
(A)

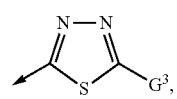
(B)

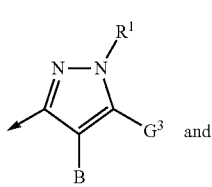
(C) and

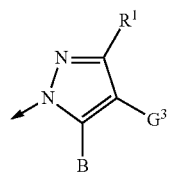
(D)

in which the arrow in each case marks the bond to the adjacent ring, $R^1$ in the case of the heterocycles (A) and (D) is hydrogen, halogen, cyano, alkyl, alkoxy, amino, alkylamino, dialkylamino, alkylthio or haloalkyl and $R^1$ in the case of heterocycle (C) is hydrogen, alkyl or haloalkyl, B is hydrogen, halogen, cyano, nitro, alkyl, cycloalkyl, haloalkyl, amino, alkylamino, dialkylamino, alkylthio or alkoxy and $G^3$ is optionally substituted heterocyclyl, optionally substituted heteroaryl or optionally substituted aryl and $G^4$ is a radical from the group of

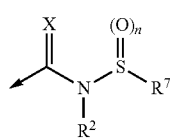
(E)

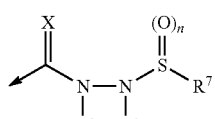
(F)

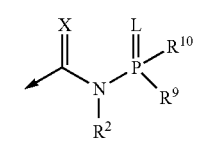
(G)

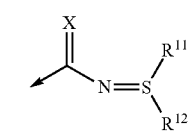
(H)

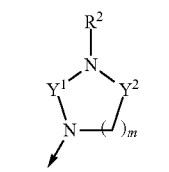
(I)

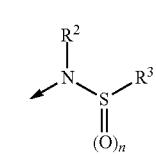
(J)

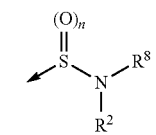
(K)

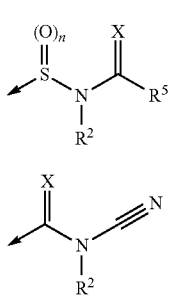

(L)

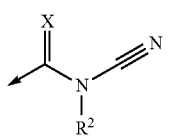

(M)

and in the case of the heterocycles (A), (B) and (C) is also the radical

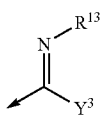

(N)

in which the arrow in each case marks the bond to $G^3$,

X is oxygen or sulphur, n is 1 or 2, $R^2$ is a radical from the group of hydrogen, alkyl, haloalkyl, cyanoalkyl, alkoxy, haloalkoxy, alkenyl, alkynyl and alkoxyalkyl, in each case optionally halogen-substituted alkylcarbonyl and alkylsulphonyl, in each case optionally halogen-substituted alkoxycarbonyl, in each case optionally halogen-, alkyl-, alkoxy-, haloalkyl- and cyano-substituted cycloalkylcarbonyl, or a cation, for example a mono- or divalent metal ion or an optionally alkyl- or arylalkyl-substituted ammonium ion, $R^3$ and $R^7$ are each independently a radical from the group of in each case optionally substituted alkyl, alkenyl and alkynyl, in each case optionally substituted cycloalkyl, cycloalkylalkyl and cycloalkenyl, in which the rings may contain at least one heteroatom from the group of sulphur, oxygen (where oxygen atoms must not be immediately adjacent) and nitrogen, in each case optionally substituted aryl, heteroaryl, arylalkyl and heteroarylalkyl and an optionally substituted amino group, $R^2$ and $R^3$ may also form, together with the N—S(O)$_n$ group to which they are bonded, a saturated or unsaturated and optionally substituted 4- to 8-membered ring which may contain one or more further heteroatoms from the group of sulphur, oxygen (where oxygen atoms must not be immediately adjacent) and nitrogen and/or at least one carbonyl group, $R^5$ is a radical from the group of in each case optionally substituted alkyl, alkoxy, alkenyl and alkynyl, in each case optionally substituted cycloalkyl, cycloalkylalkyl and cycloalkenyl, in which the rings may contain at least one heteroatom from the group of sulphur, oxygen (where oxygen atoms must not be immediately adjacent) and nitrogen, in each case optionally substituted aryl, heteroaryl, arylalkyl and heteroarylalkyl and an optionally substituted amino group, $R^8$ is a radical from the group of hydrogen, in each case optionally substituted alkyl, alkoxy, alkenyl and alkynyl, in each case optionally substituted cycloalkyl, cycloalkylalkyl and cycloalkenyl, in which the rings may contain at least one heteroatom from the group of sulphur, oxygen (where oxygen atoms must not be immediately adjacent) and nitrogen, in each case optionally substituted aryl, heteroaryl, arylalkyl and heteroarylalkyl and an optionally substituted amino group, $R^2$ and $R^5$ may also form, together with the N—C(X) group to which they are bonded, a saturated or unsaturated and optionally substituted 4- to 8-membered ring which may contain one or more further heteroatoms from the group of sulphur, oxygen (where oxygen atoms must not be immediately adjacent) and nitrogen and/or at least one carbonyl group, $R^6$ is hydrogen or alkyl, $R^2$ and $R^6$ may also form, together with the nitrogen atoms to which they are bonded, a saturated or unsaturated and optionally substituted 4- to 8-membered ring which may contain at least one further heteroatom from the group of sulphur, oxygen (where oxygen atoms must not be immediately adjacent) and nitrogen and/or at least one carbonyl group, $R^2$ and $R^7$ in the radical (E) may also form, together with the N—S(O)$_n$ group to which they are bonded, a saturated or unsaturated and optionally substituted 4- to 8-membered ring which may contain one or more further heteroatoms from the group of sulphur, oxygen (where oxygen atoms must not be immediately adjacent) and nitrogen and/or at least one carbonyl group, $R^6$ and $R^7$ may also form, together with the N—S(O)$_n$ group to which they are bonded, a saturated or unsaturated and optionally substituted 4- to 8-membered ring which may contain one or more further heteroatoms from the group of sulphur, oxygen (where oxygen atoms must not be immediately adjacent) and nitrogen and/or at least one carbonyl group, $R^2$ and $R^8$ may also form, together with the nitrogen atom to which they are bonded, a saturated or unsaturated and optionally substituted 4- to 8-membered ring which may contain one or more further heteroatoms from the group of sulphur, oxygen (where oxygen atoms must not be immediately adjacent) and nitrogen and/or at least one carbonyl group, L is oxygen or sulphur, $R^9$ and $R^{10}$ are each independently an in each case optionally substituted radical from the group of alkyl, alkenyl, alkynyl, alkoxy, alkenyloxy, alkynyloxy, cycloalkyl, cycloalkyloxy, cycloalkenyloxy, cycloalkylalkoxy, alkylthio, alkenylthio, phenoxy, phenylthio, benzyloxy, benzylthio, heteroaryloxy, heteroarylthio, heteroarylalkoxy and heteroarylalkylthio, $R^9$ and $R^{10}$ may also form, together with the phosphorus atom to which they are bonded, a saturated or unsaturated and optionally substituted 5- to 7-membered ring which may contain one or two heteroatoms from the group of oxygen (where oxygen atoms must not be immediately adjacent) and sulphur, and $R^{11}$ and $R^{12}$ are each independently an in each case optionally substituted radical from the group of alkyl, alkenyl, alkynyl, phenyl and phenylalkyl, $Y^1$ and $Y^2$ are each independently CO or S(O)$_2$, m is 1, 2, 3 or 4, $R^{13}$ is a radical from the group of hydrogen, alkyl, haloalkyl, cyano, cyanoalkyl, hydroxyalkyl, hydroxyl, alkoxy, alkoxyalkyl, alkylthioalkyl, alkenyl, haloalkenyl, cyanoalkenyl, alkynyl, haloalkynyl, cyanoalkynyl, alkylcarbonyl and alkoxycarbonyl, $Y^3$ is a radical from the group of alkoxy, haloalkoxy, alkylthio, haloalkylthio and NR$^{14}$R$^{15}$ where R$^{14}$ and R$^{15}$ are each independently radicals from the group of hydrogen, alkyl, cycloalkyl, cycloalkylalkyl, haloalkyl, cyano, cyanoalkyl, hydroxyl, alkoxy, haloalkoxy, hydroxyalkyl, alkoxyalkyl, alkylthioalkyl, alkenyl, haloalkenyl, cyanoalkenyl, alkynyl, haloalkynyl, cyanoalkynyl, alkylcarbonyl and alkoxycarbonyl, or $R^{14}$ and $R^{15}$ together with the nitrogen atom to which they are bonded may form an optionally substituted saturated or unsaturated 5- to 8-membered ring optionally containing heteroatoms, $G^3$ and $G^4$ may additionally also together form an optionally substituted heterocycle which optionally contains one or more further heteroatoms from the group of oxygen, nitrogen and sulphur, and salts and N-oxides of the compounds of the formula (I).

When $G^1$ is N, compounds of the formula (Ia) are thus obtained

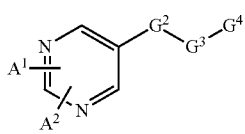

(Ia)

and, when $G^1$ is C-$A^1$, compounds of the formula (Ib) are obtained

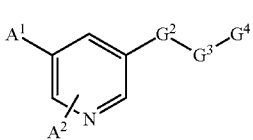

(Ib)

in which the remaining substituents are each as defined above.

It has additionally been found that the compounds of the formula (I) can be obtained by the processes described below.

Depending on the $G^4$ radical, the compounds of the formula (I) can be divided into the substructures ($I_E$) to ($I_M$).

Compounds of the formula ($I_{E-G}$, $I_M$) can be prepared, for example, by reacting the carboxylic acids of the formula ($II_1$) or the acid chlorides thereof with amine derivatives of the formula ($III_{E-G}$, $III_M$).

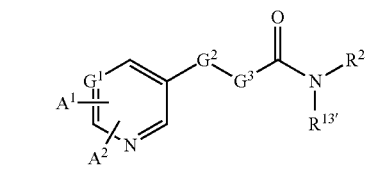

($II_1$)     ($III_{E-G}$, $III_M$)

($I_{E-G}$, $I_M$)

where $R^{13'}$ is

($III_E$)

($III_F$)

($III_G$)   or

($III_M$)

Compounds of the formula ($I_1$) can be prepared, for example, as will be explained in detail later, from the amines of the formula ($II_2$).

Compounds of the formula ($I_J$) can be prepared, for example, by reacting the heterocyclic amines of the formula ($II_2$) with sulphonyl chlorides of the formula ($III_J$).

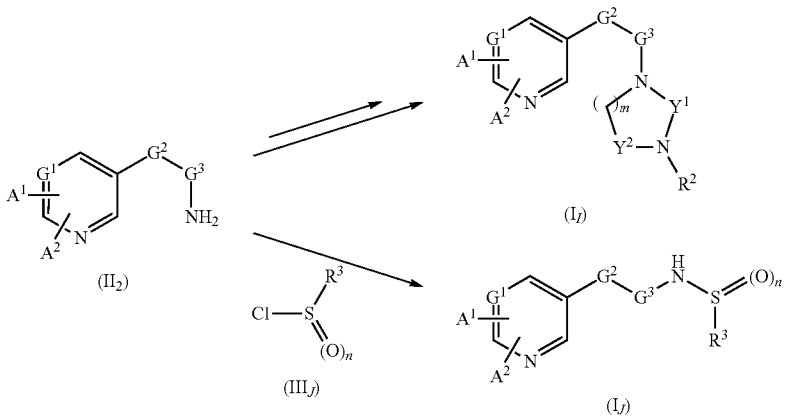

Compounds of the formula ($I_K$) can be prepared, for example, by reacting sulphonyl chlorides of the formula ($II_3$) with amines of the formula ($III_K$).

Compounds of the formula ($I_L$) can be prepared, for example, by reacting sulphonyl chlorides of the formula ($II_3$) with amides of the formula ($III_L$).

The compounds of the general formula (I) may, where appropriate, depending on the nature of the substituents, be in the form of geometric and/or optically active isomers or corresponding isomer mixtures in different compositions. The invention relates both to the pure isomers and to the isomer mixtures.

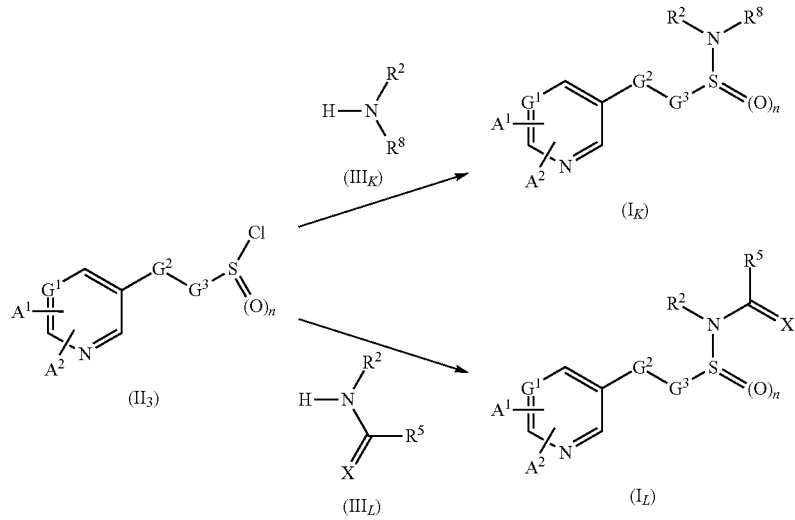

Compounds of the formula ($I_N$) can be prepared, for example, by reacting nitriles of the formula ($II_4$) or thio amides of the formula ($II_5$) with oxy, thio or amino derivatives of the formula ($III_N$).

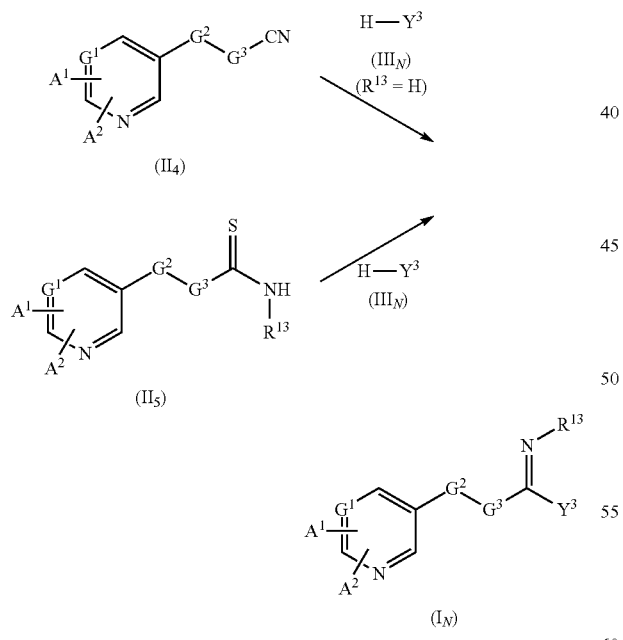

Finally, it has been found that novel compounds of the formula (I) have very pronounced biological properties and are suitable in particular for controlling animal pests, especially insects, arachnids and nematodes, which are encountered in agriculture, in forests, in the protection of stored products and materials and in the hygiene sector.

The inventive compounds may also be present as metal complexes, as described for other amides, for example, in DE 2221647.

Preferred substituents or ranges for the radicals shown in the compounds of the formula (I) are elucidated below.

$A^1$ and $A^2$ are each independently hydrogen, halogen, cyano, nitro, $C_1$-$C_6$-alkyl, $C_3$-$C_6$-cycloalkyl or $C_1$-$C_6$-alkoxy.

$G^1$ is N or C-$A^1$.

$G^2$ is a radical from the group of

(A)

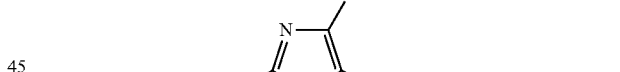

(B)

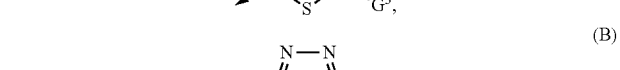

(C)

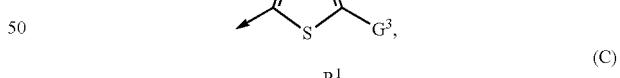

and (D)

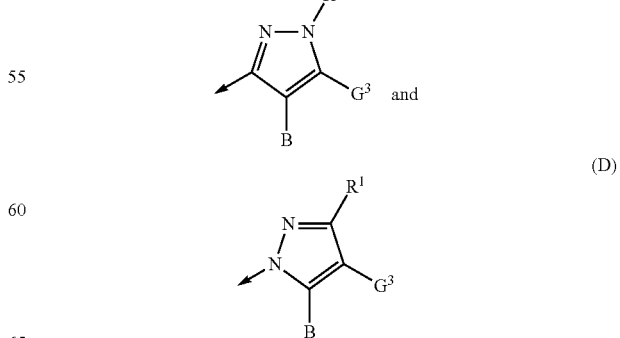

in which the arrow marks the bond to the adjacent ring.

$R^1$ in the case of the heterocycles (A) and (D) is hydrogen, halogen, cyano, $C_1$-$C_6$-alkyl, $C_1$-$C_6$-alkoxy or $C_1$-$C_6$-haloalkyl.

$R^1$ in the case of heterocycle (C) is hydrogen, $C_1$-$C_6$-alkyl or $C_1$-$C_6$-haloalkyl.

B is hydrogen, halogen, cyano, nitro, $C_1$-$C_6$-alkyl, $C_1$-$C_6$-haloalkyl, $C_1$-$C_6$-alkoxy or $C_3$-$C_6$-cycloalkyl.

$G^3$ is in each case optionally halogen-, cyano-, nitro-, amino-, $C_1$-$C_6$-alkylamino-, alkylamino-, $C_1$-$C_6$-alkyl-, $C_3$-$C_6$-cycloalkyl-, $C_1$-$C_6$-haloalkyl-, hydroxyl-, $C_1$-$C_6$-alkoxy-, $C_1$-$C_6$-haloalkoxy-, $C_1$-$C_6$-alkylthio-, $C_1$-$C_6$-alkylcarbonyl-, $C_1$-$C_6$-alkoxycarbonyl-, $C_2$-$C_6$-alkenyl- or $C_2$-$C_6$-alkynyl-substituted 5-membered heteroaryl or 6-membered heteroaryl; $G^3$ is especially in each case optionally halogen-, cyano-, nitro-, amino-, $C_1$-$C_6$-alkylamino-, di-($C_1$-$C_6$)-alkylamino-, $C_1$-$C_6$-alkyl-, $C_3$-$C_6$-cycloalkyl-, $C_1$-$C_6$-haloalkyl-, hydroxyl-, $C_1$-$C_6$-alkoxy-, $C_1$-$C_6$-haloalkoxy-, $C_1$-$C_6$-alkylthio-, $C_1$-$C_6$-alkylcarbonyl-, $C_1$-$C_6$-alkoxycarbonyl-, $C_2$-$C_6$-alkenyl- or $C_2$-$C_6$-alkynyl-substituted pyrazolyl, oxazolyl, thiazolyl, oxadiazolyl, triazolyl, pyridinyl, pyridazinyl, pyrimidinyl, pyrazinyl or triazinyl, and additionally optionally halogen-, cyano-, nitro-, amino-, $C_1$-$C_6$-alkylamino-, alkylamino-, $C_1$-$C_6$-alkyl-, $C_3$-$C_6$-cycloalkyl-, $C_1$-$C_6$-haloalkyl-, hydroxyl-, $C_1$-$C_6$-alkoxy-, $C_1$-$C_6$-haloalkoxy-, $C_1$-$C_6$-alkylthio-, $C_1$-$C_6$-alkylcarbonyl-, $C_1$-$C_6$-alkoxycarbonyl-, $C_2$-$C_6$-alkenyl- or $C_2$-$C_6$-alkynyl-substituted phenyl, and when $G^4$ is one of the radicals (E), (F), (G), (H), (K), (L) and (M), $G^3$ may also be optionally halogen-, cyano-, nitro-, amino-, $C_1$-$C_6$-alkylamino-, $C_1$-$C_6$-alkyl-, $C_3$-$C_6$-cycloalkyl-, $C_1$-$C_6$-haloalkyl-, hydroxyl-, $C_1$-$C_6$-alkoxy-, $C_1$-$C_6$-haloalkoxy-, $C_1$-$C_6$-alkylthio-, $C_1$-$C_6$-alkylcarbonyl-, $C_1$-$C_6$-alkoxycarbonyl-, $C_2$-$C_6$-alkenyl- or $C_2$-$C_6$-alkynyl-substituted 5-membered heterocyclyl or 6-membered heterocyclyl; $G^3$ in that case is especially a radical from the group of

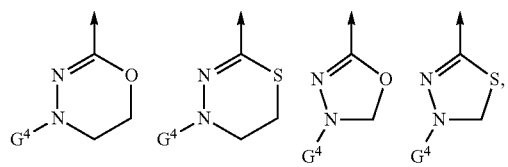

in which the arrow in each case marks the bond to $G^2$, and $G^4$ is also shown for illustration.

$G^4$ is a radical from the group of

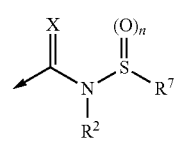 (E)

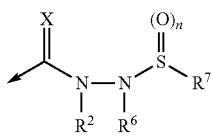 (F)

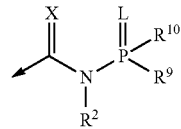 (G)

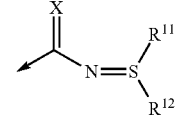 (H)

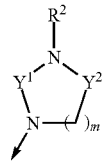 (I)

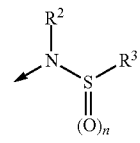 (J)

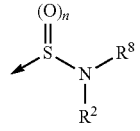 (K)

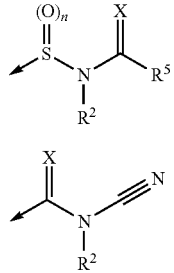 (L)

(M)

and in the case of the heterocycles (A), (B) and (C) is also the radical

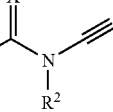 (N)

in which the arrow marks the bond to $G^3$.

X is oxygen or sulphur.

n is 1 or 2.

$R^2$ is a radical from the group of hydrogen, $C_1$-$C_6$-alkyl, $C_1$-$C_6$-haloalkyl, cyano-$C_1$-$C_6$-alkyl, $C_1$-$C_6$-alkoxy, $C_1$-$C_6$-haloalkoxy, $C_2$-$C_6$-alkenyl, $C_2$-$C_6$-alkynyl, $C_1$-$C_6$-alkoxy-$C_1$-$C_6$-alkyl, in each case optionally halogen-substituted $C_1$-$C_6$-alkylcarbonyl and $C_1$-$C_6$-alkylsulphonyl, optionally halogen-substituted $C_1$-$C_6$-alkoxycarbonyl, optionally halogen-, $C_1$-$C_6$-alkyl-, $C_1$-$C_6$-alkoxy-, $C_1$-$C_6$-haloalkyl- and cyano-substituted $C_3$-$C_6$-cycloalkylcarbonyl, or a cation, for example a mono- or divalent metal ion, such as Na⁺ and K⁺, or an optionally $C_1$-$C_6$-alkyl- or aryl-$C_1$-$C_6$-alkyl-substituted ammonium ion.

$R^3$ and $R^7$ are each independently a radical from the group of in each case optionally halogen-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl- and $C_1$-$C_6$-haloalkylsulphonyl-substituted $C_1$-$C_6$-alkyl, $C_2$-$C_6$-alkenyl and $C_2$-$C_6$-alkynyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl, $C_3$-$C_6$-cycloalkyl-$C_1$-$C_6$-alkyl and $C_3$-$C_6$-cycloalkenyl, in which the rings may contain at least one heteroatom from the group of sulphur, oxygen (where oxygen atoms must not be immediately adjacent) and nitrogen (and especially

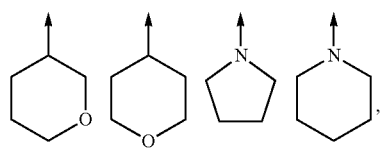

where the arrow in each case marks the bond to the sulphur atom in the radicals (E), (F) and (J)), in each case optionally halogen-, cyano- (including in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted aryl, heteroaryl, aryl-$C_1$-$C_6$-alkyl and heteroaryl-$C_1$-$C_6$-alkyl, or NR'R" in which R" and R" are each independently a radical from the group of hydrogen, $C_1$-$C_6$-alkyl, $C_1$-$C_6$-haloalkyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-alkylcarbonyl and $C_1$-$C_6$-alkoxylcarbonyl.

$R^2$ and $R^3$ may also, together with the N—S(O)$_n$ group to which they are bonded, form a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or more further heteroatoms from the group of sulphur, oxygen (where oxygen atoms must not be immediately adjacent) and nitrogen and/or at least one carbonyl group; $R^2$ and $R^3$ may especially, together with the N—S(O)$_n$ group to which they are bonded, be a radical from the group of

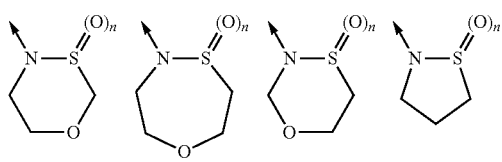

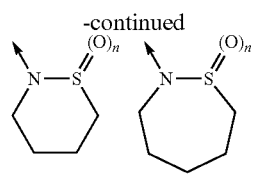

(in which the arrow again in each case marks the bond to $G^3$).

$R^5$ is a radical from the group of in each case optionally halogen-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl- or $C_1$-$C_6$-haloalkylsulphonyl-substituted $C_1$-$C_6$-alkyl, $C_1$-$C_6$-alkoxy, $C_2$-$C_6$-alkenyl and $C_2$-$C_6$-alkynyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl, $C_3$-$C_6$-cycloalkyl-$C_1$-$C_6$-alkyl and $C_3$-$C_6$-cycloalkenyl, in which the rings may contain at least one heteroatom from the group of sulphur, oxygen (where oxygen atoms must not be immediately adjacent) and nitrogen, in each case optionally halogen-, cyano-(including in the alkyl moiety), nitro-, $C_1$-$C_6$-alkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkyl sulphonyl-, $C_1$-$C_6$-haloalkylsulphonyl-, amino-, $C_1$-$C_6$-alkylamino-, $C_1$-$C_6$-alkylcarbonylamino-, $C_1$-$C_6$-alkoxycarbonylamino-, $C_1$-$C_6$-haloalkoxy-$C_1$-$C_6$-alkyl-, $C_2$-$C_6$-alkenyl-, $C_2$-$C_6$-alkynyl-, $C_1$-$C_6$-alkyl carbonyl-, $C_1$-$C_6$-alkoxycarbonyl- or aminocarbonyl-substituted aryl, heteroaryl, aryl-$C_1$-$C_6$-alkyl and heteroaryl-$C_1$-$C_6$-alkyl, or NR'R" in which R' and R" are each independently a radical from the group of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxylcarbonyl.

$R^8$ is a radical from the group of hydrogen, in each case optionally halogen-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl- or $C_1$-$C_6$-haloalkylsulphonyl-substituted $C_1$-$C_6$-alkyl, $C_1$-$C_6$-alkoxy, $C_2$-$C_6$-alkenyl and $C_2$-$C_6$-alkynyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl, $C_3$-$C_6$-cycloalkyl-$C_1$-$C_6$-alkyl and $C_3$-$C_6$-cycloalkenyl, in which the rings may contain at least one heteroatom from the group of sulphur, oxygen (where oxygen atoms must not be immediately adjacent) and nitrogen, in each case optionally halogen-, cyano-(including in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted aryl, heteroaryl, aryl-$C_1$-$C_6$-alkyl and heteroaryl-$C_1$-$C_6$-alkyl, or NR'R" in which R' and R" are each independently a radical from the group of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxylcarbonyl.

$R^2$ and $R^5$ may also, together with the N—C(X) group to which they are bonded, form a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or more further heteroatoms from the group of sulphur, oxygen (where oxygen atoms must not be immediately adjacent) and nitrogen and/or at least one carbonyl group; $R^2$ and $R^5$ may especially, together with the N—C(X) group to which they are bonded, be a radical from the group of

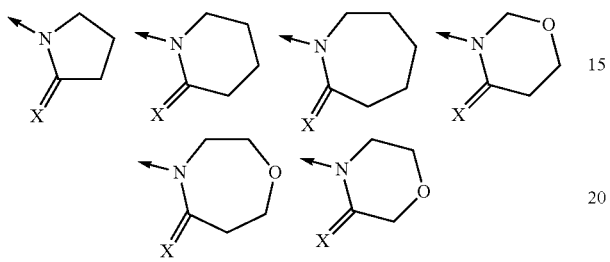

(in which the arrow in each case marks the bond to the sulphur atom in the radical (L)).

$R^6$ is hydrogen or $C_1$-$C_6$-alkyl.

$R^2$ and $R^6$ may also, together with the nitrogen atoms to which they are bonded, be a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain at least one further heteroatom from the group of sulphur, oxygen (where oxygen atoms must not be immediately adjacent) and nitrogen and/or at least one carbonyl group; $R^2$ and $R^6$ may especially, together with the N—N group to which they are bonded, be a radical from the group of

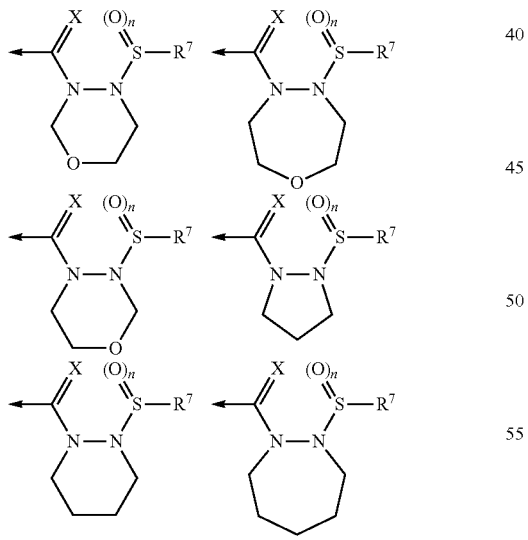

(where the whole radical (F) is depicted and the arrow again in each case marks the bond to $G^3$).

$R^2$ and $R^7$ may also, in the case that $G^3$ is (E), together with the N—S(O)$_n$ group to which they are bonded, form a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or more further heteroatoms from the group of sulphur, oxygen (where oxygen atoms must not be immediately adjacent) and nitrogen and/or at least one carbonyl group; $R^2$ and $R^7$ may especially, together with the N—S(O)$_n$ group to which they are bonded, be a radical from the group of

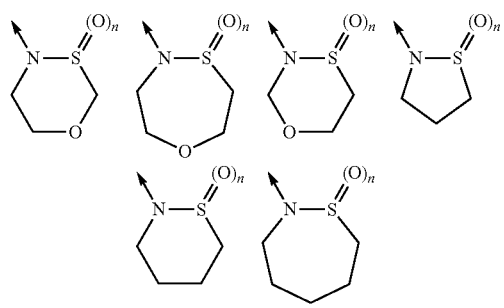

(in which the arrow in each case marks the bond to the C(X) group).

$R^6$ and $R^7$ may also, in the case that $G^3$ is (F), together with the N—S(O)$_n$ group to which they are bonded, form a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or more further heteroatoms from the group of sulphur, oxygen (where oxygen atoms must not be immediately adjacent) and nitrogen and/or at least one carbonyl group; $R^6$ and $R^7$ may especially, together with the N—S(O)$_n$ group to which they are bonded, be a radical from the group of

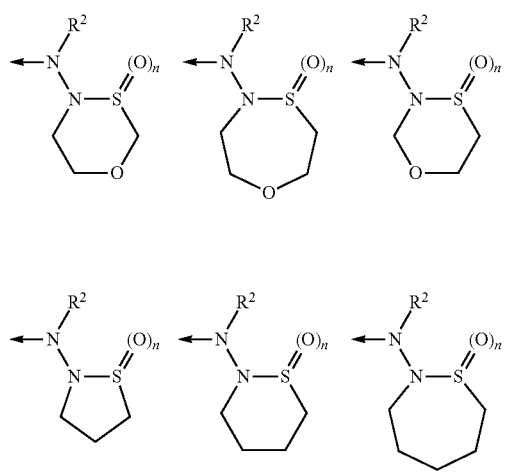

(in which the N—$R^2$ group is also shown and the arrow in each case marks the bond to the C(X) group).

$R^2$ and $R^8$ may also, together with the nitrogen atom to which they are bonded, form a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or more further heteroatoms from the group of sulphur, oxygen (where oxygen atoms must not be immediately adjacent) and nitrogen and/or at least one carbonyl group; $R^2$ and $R^8$ may especially, together with the nitrogen atom to which they are bonded, be a radical from the group of

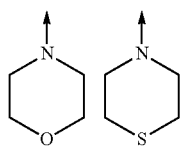

(in which the arrow in each case marks the bond to the sulphur atom in the radical (K)).

L is oxygen or sulphur.

$R^9$ and $R^{10}$ are each independently an in each case optionally halogen-substituted radical from the group of $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_3$-$C_6$-cycloalkyl, $C_3$-$C_6$-cycloalkyloxy, $C_3$-$C_6$-cycloalkenyloxy, $C_3$-$C_6$-cycloalkyl-$C_1$-$C_6$-alkoxy, $C_1$-$C_6$-alkylthio, $C_2$-$C_6$-alkenylthio, phenoxy, phenylthio, benzyloxy, benzylthio, heteroaryloxy, heteroarylthio, heteroaryl-$C_1$-$C_6$-alkoxy and heteroaryl-$C_1$-$C_6$-alkylthio.

$R^9$ and $R^{10}$ may also, together with the phosphorus atom to which they are bonded, form a saturated or unsaturated and optionally halogen-, $C_1$-$C_6$-alkyl-, $C_1$-$C_6$-alkoxy-, $C_1$-$C_6$-haloalkoxy-substituted 5- to 7-membered ring which may contain one or two heteroatoms from the group of oxygen (where oxygen atoms must not be immediately adjacent) and sulphur; $R^9$ and $R^{10}$ may especially, together with the phosphorus atom to which they are bonded, be the radical

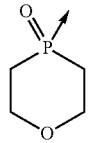

(in which the arrow marks the bond to the nitrogen atom in the radical (G)).

$R^{11}$ and $R^{12}$ are each independently an in each case optionally halogen-, $C_1$-$C_6$-alkyl-, $C_1$-$C_6$-haloalkyl-, $C_1$-$C_6$-alkoxy-, $C_1$-$C_6$-haloalkoxy-substituted radical from the group of $C_1$-$C_6$-alkyl, $C_2$-$C_6$-alkenyl, $C_2$-$C_6$-alkynyl, phenyl and phenyl-$C_1$-$C_6$-alkyl.

$Y^1$ and $Y^2$ are each independently C=O or $S(O)_2$.

m is 1, 2, 3 or 4.

$R^{13}$ is a radical from the group of hydrogen, $C_1$-$C_6$-alkyl, $C_1$-$C_6$-haloalkyl, cyano, $C_1$-$C_6$-cyanoalkyl, $C_1$-$C_6$-hydroxyalkyl, hydroxyl, $C_1$-$C_6$-alkoxy, $C_2$-$C_6$-alkenyl, $C_2$-$C_6$-haloalkenyl, $C_2$-$C_6$-cyanoalkenyl, $C_2$-$C_6$-alkynyl, $C_2$-$C_6$-haloalkynyl, $C_2$-$C_6$-cyanoalkynyl, $C_1$-$C_7$-alkylcarbonyl and $C_1$-$C_7$-alkoxycarbonyl.

$Y^3$ is a radical from the group of $C_1$-$C_6$-alkoxy, $C_1$-$C_6$-haloalkoxy, $C_1$-$C_6$-alkylthio, haloalkylthio and $NR^{14}R^{15}$ where $R^{14}$ and $R^{15}$ are each independently a radical from the group of hydrogen, $C_1$-$C_6$-alkyl, $C_3$-$C_8$-cycloalkyl, $C_1$-$C_6$-haloalkyl, cyano, $C_1$-$C_6$-cyanoalkyl, hydroxyl, $C_1$-$C_6$-alkoxy, $C_1$-$C_6$-haloalkoxy, $C_1$-$C_6$-hydroxyalkyl, $C_2$-$C_6$-alkenyl, $C_2$-$C_6$-haloalkenyl, $C_2$-$C_6$-cyanoalkenyl, $C_2$-$C_6$-alkynyl, $C_2$-$C_6$-haloalkynyl, $C_2$-$C_6$-cyanoalkynyl, $C_1$-$C_7$-alkylcarbonyl and $C_1$-$C_7$-alkoxycarbonyl, or $R^{14}$ and $R^{15}$ together with the nitrogen atom to which they are bonded are an optionally halogen-, cyano-, $C_1$-$C_6$-alkyl-, $C_1$-$C_6$-haloalkyl-, $C_1$-$C_6$-alkoxy-, $C_3$-$C_8$-cycloalkyl- or $C_1$-$C_6$-alkylthio-substituted saturated or unsaturated 5- to 8-membered ring which may contain one or more further atoms from the group of sulphur, oxygen (where oxygen atoms must not be immediately adjacent) and nitrogen and/or at least one carbonyl group; $R^{14}$ and $R^{15}$ may especially, together with the nitrogen atom to which they are bonded, be a radical from the group of

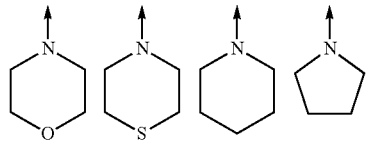

(in which the arrow in each case marks the bonds to the carbon atom in the (N) radical).

$G^3$ and $G^4$ may additionally together form an optionally substituted heterocycle which optionally contains further heteroatoms from the group of oxygen, nitrogen and sulphur; $G^3$ and $G^4$ may especially form a bicycle from the group of

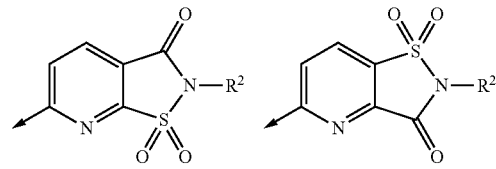

(in which the arrow marks the bond to $G^2$).

Particularly preferred substituents or ranges for the radicals shown in the compounds of the formula (I) are elucidated below.

$A^1$ is hydrogen, halogen or cyano, and $A^1$ is especially a radical from the group of hydrogen, fluorine and chlorine.

$A^2$ is hydrogen.

$G^1$ is N or C-$A^1$.

$G^2$ is a radical from the group of

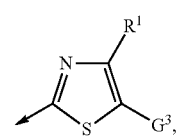
(A)

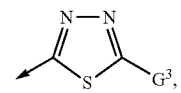
(B)

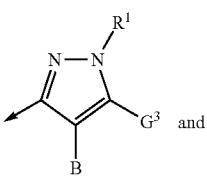
(C) and

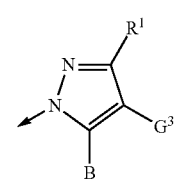
(D)

in which the arrow marks the bond to the adjacent ring.

$R^1$ is hydrogen or $C_1$-$C_4$-alkyl, and $R^1$ is especially hydrogen or methyl.

B is hydrogen.

$G^3$ is in each case optionally halogen-, cyano-, nitro-, amino-, $C_1$-$C_6$-alkylamino-, di-$C_1$-$C_6$-alkylamino-, $C_1$-$C_6$-alkyl-, $C_3$-$C_6$-cycloalkyl-, $C_1$-$C_6$-haloalkyl-, hydroxyl-, $C_1$-$C_6$-alkoxy-, $C_1$-$C_6$-haloalkoxy-, $C_1$-$C_6$-alkylthio-, $C_1$-$C_6$-alkylcarbonyl-, $C_1$-$C_6$-alkoxycarbonyl-, $C_2$-$C_6$-alkenyl- or $C_2$-$C_6$-alkynyl-substituted 5-membered heteroaryl or 6-membered heteroaryl;

$G^3$ is especially optionally halogen-, cyano-, nitro-, amino-, $C_1$-$C_6$-alkylamino-, di-$C_1$-$C_6$-alkylamino-, $C_1$-$C_6$-alkyl-, $C_3$-$C_6$-cycloalkyl-, $C_1$-$C_6$-haloalkyl-, hydroxyl-, $C_1$-$C_6$-alkoxy-, $C_1$-$C_6$-haloalkoxy-, $C_1$-$C_6$-alkylthio-, $C_1$-$C_6$-alkylcarbonyl-, $C_1$-$C_6$-alkoxycarbonyl-, $C_2$-$C_6$-alkenyl- or $C_2$-$C_6$-alkynyl-substituted pyrazolyl, oxazolyl, triazolyl, oxadiazolyl, triazolyl, pyridinyl, pyridazinyl, pyrimidinyl, pyrazinyl or triazinyl; $G^3$ is with emphasis an optionally halogen-, cyano-, methyl-, methoxy-, trifluoromethyl-, amino- or dimethylamino-substituted radical from the group of

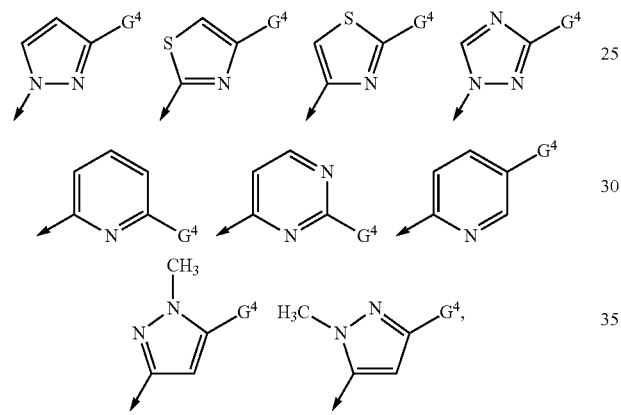

in which the arrow in each case marks the bond to $G^2$, and $G^4$ is also shown for illustration, and additionally optionally halogen-, cyano-, nitro-, amino-, $C_1$-$C_6$-alkylamino-, alkylamino-, $C_1$-$C_6$-alkyl-, $C_3$-$C_6$-cycloalkyl-, $C_1$-$C_6$-haloalkyl-, hydroxyl-, $C_1$-$C_6$-alkoxy-, $C_1$-$C_6$-haloalkoxy-, $C_1$-$C_6$-alkylthio-, $C_1$-$C_6$-alkylcarbonyl-, $C_1$-$C_6$-alkoxycarbonyl-, $C_2$-$C_6$-alkenyl- or $C_2$-$C_6$-alkynyl-substituted phenyl, and when $G^4$ is one of the radicals (E) and (L), $G^3$ may also be optionally halogen-, cyano-, nitro-, amino-, $C_1$-$C_6$-alkylamino-, $C_1$-$C_6$-alkyl-, $C_3$-$C_6$-cycloalkyl-, $C_1$-$C_6$-haloalkyl-, $C_1$-$C_6$-alkoxy-, $C_1$-$C_6$-haloalkoxy-, $C_1$-$C_6$-alkylthio-, $C_1$-$C_6$-alkylcarbonyl-, $C_1$-$C_6$-alkoxycarbonyl-, $C_2$-$C_6$-alkenyl- or $C_2$-$C_6$-alkynyl-substituted 5-membered heterocyclyl or 6-membered heterocyclyl from the group of

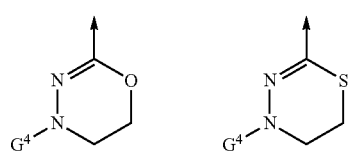

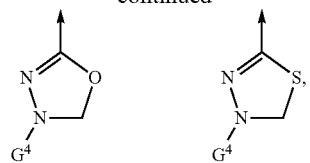

in which the arrow in each case marks the bond to $G^2$, and $G^4$ is also shown for illustration.

$G^4$ is a radical from the group of

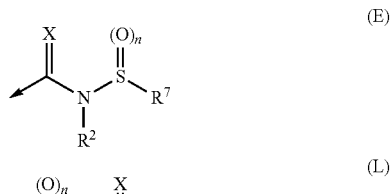

and in the case of the heterocycles (A), (B), and (C) is also the radical

in which the arrow in each case marks the bond to $G^3$.

X is oxygen.

n is 2.

$R^2$ is a radical from the group of hydrogen, $C_1$-$C_4$-alkyl, $C_2$-$C_4$-alkynyl, cyano-$C_1$-$C_4$-alkyl and $C_1$-$C_4$-alkoxy-$C_1$-$C_4$-alkyl, optionally halogen-substituted $C_1$-$C_4$-alkylcarbonyl or $C_1$-$C_4$-alkylsulphonyl, optionally halogen-substituted $C_1$-$C_4$-alkoxycarbonyl, optionally halogen-, $C_1$-$C_4$-alkyl-, $C_1$-$C_4$-alkoxy-, $C_1$-$C_4$-haloalkyl- and cyano-substituted $C_3$-$C_6$-cycloalkylcarbonyl, or a cation, for example a mono- or divalent metal ion or an optionally $C_1$-$C_4$-alkyl- or aryl-$C_1$-$C_4$-alkyl-substituted ammonium ion; $R^2$ is especially a radical from the group of hydrogen, methyl, ethyl, $CH_2OCH_3$, $CH_2OCH_2CH_3$, $COCH_3$, $COCH_2CH_3$, cyclopropyl, $Na^+$, $K^+$ and $^+N(CH_3)_4$.

$R^5$ is a radical from the group of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl, in which the rings may contain at least one heteroatom from the group of sulphur, oxygen (where oxygen atoms must not be immediately adjacent) and nitrogen (and especially

where the arrow in each case marks the bond to the carbon atom in the radical (L)), in each case optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-haloalkylsulphonyl-, amino-, $C_1$-$C_4$-alkylamino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl, or NR'R" in which R' and R" are each independently a radical from the group of hydrogen and $C_1$-$C_4$-alkyl, and $R^5$ is especially a radical from the group of methyl, ethyl, i-propyl, $CF_3$, $CHF_2$, $CH_2F$, $CH_2CF_3$, cyclopropyl, dimethylamino, diethylamino, phenyl and benzyl.

$R^7$ is a radical from the group of in each case optionally halogen-, $C_1$-$C_4$-alkoxy-, haloalkoxy-, $C_1$-$C_4$-alkylthio-, $C_1$-$C_4$-haloalkylthio-, $C_1$-$C_4$-alkylsulphinyl-, haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl, in which the rings may contain at least one heteroatom from the group of sulphur, oxygen (where oxygen atoms must not be immediately adjacent) and nitrogen (and especially

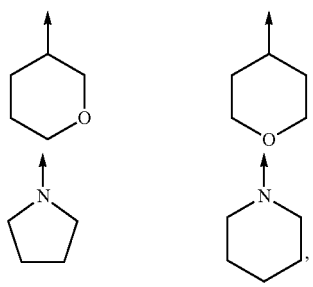

where the arrow in each case marks the bond to the sulphur atom in the radical (E)), in each case optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonyl amino-, $C_1$-$C_4$-alkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl or NR"R" in which R' and R" are each independently a radical from the group of hydrogen, $C_1$-$C_4$-alkyl and $C_3$-$C_6$-cycloalkyl-$C_1$-$C_4$-alkyl, and $R^7$ is especially a radical from the group of methyl, ethyl, i-propyl, $CF_3$, $CHF_2$, $CH_2F$, $CH_2CF_3$, cyclopropyl, cyclopropylmethyl, cyclopropylethyl, dimethylamino, diethylamino, phenyl and benzyl.

$G^3$ and $G^4$ may additionally also form an optionally substituted heterocycle which optionally contains further heteroatoms from the group of oxygen, nitrogen and sulphur; $G^3$ and $G^4$ may especially form a bicycle from the group of

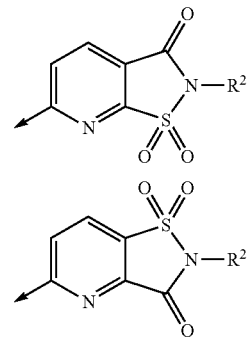

(in which the arrow marks the bond to $G^2$).

$R^{13}$ is a radical from the group of hydrogen, $C_1$-$C_4$-alkyl, $C_1$-$C_4$-haloalkyl, cyano, $C_1$-$C_4$-cyanoalkyl, $C_1$-$C_4$-hydroxyalkyl, hydroxyl, $C_1$-$C_4$-alkoxy, $C_1$-$C_4$-alkoxy-$C_1$-$C_4$-alkyl, $C_1$-$C_4$-alkylthio-$C_1$-$C_4$-alkyl, $C_2$-$C_4$-alkenyl, $C_2$-$C_4$-haloalkenyl, $C_2$-$C_4$-cyanoalkenyl, $C_2$-$C_4$-alkynyl, $C_2$-$C_4$-haloalkynyl, $C_2$-$C_4$-cyanoalkynyl, $C_1$-$C_5$-alkylcarbonyl and $C_1$-$C_5$-alkoxycarbonyl.

$Y^3$ is a radical from the group of $C_1$-$C_4$-alkoxy, $C_1$-$C_4$-haloalkoxy, $C_1$-$C_4$-alkylthio, $C_1$-$C_4$-haloalkylthio and $NR^{14}R^{15}$ where $R^{14}$ and $R^{15}$ are each independently a radical from the group of hydrogen, $C_1$-$C_4$-alkyl, $C_3$-$C_6$-cycloalkyl, $C_3$-$C_6$-cycloalkyl-$C_1$-$C_4$-alkyl, $C_1$-$C_4$-haloalkyl, cyano, $C_1$-$C_4$-cyanoalkyl, hydroxyl, $C_1$-$C_4$-alkoxy, $C_1$-$C_4$-haloalkoxy, hydroxyalkyl, $C_1$-$C_4$-alkylthio-$C_1$-$C_4$-alkyl, $C_2$-$C_4$-alkenyl, $C_2$-$C_4$-haloalkenyl, $C_2$-$C_4$-cyanoalkenyl, $C_2$-$C_4$-alkynyl, $C_2$-$C_4$-haloalkynyl, $C_2$-$C_4$-cyanoalkynyl, $C_1$-$C_5$-alkylcarbonyl, $C_1$-$C_5$-alkoxycarbonyl, or $R^{14}$ and $R^{15}$ together with the nitrogen atom to which they are bonded are an optionally halogen-, cyano-, $C_1$-$C_4$-alkyl-, $C_1$-$C_4$-haloalkyl-, $C_1$-$C_4$-alkoxy-, $C_3$-$C_6$-cycloalkyl- or $C_1$-$C_4$-alkylthio-substituted saturated or unsaturated five- to eight-membered ring which may contain a further atom from the group of sulphur, oxygen and nitrogen and/or one carbonyl group; $R^{14}$ and $R^{15}$ may especially, together with the nitrogen atom to which they are bonded, be a radical from the group of

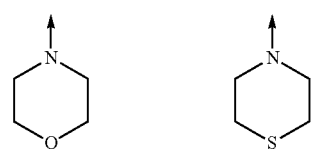

-continued

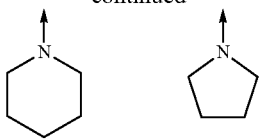

(in which the arrow in each case marks the bonds to the carbon atom in the (N) radical).

Very particularly preferred substituents or ranges of the radicals shown in the compounds of the formula (I) are elucidated hereinafter.

$A^1$ is a radical from the group of hydrogen, fluorine and chlorine.

$A^2$ is hydrogen.

$G^1$ is N or $C-A^1$, which leads to compounds containing the following structural elements:

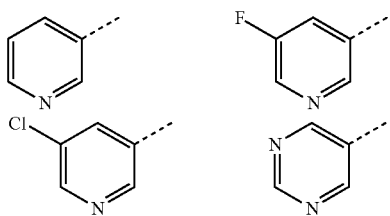

in which the broken line means the bond to $G^2$.

$G^2$ is a radical from the group of

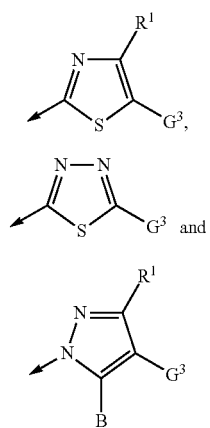

in which the arrow in each case marks the bond to the adjacent ring.

$R^1$ is hydrogen or methyl.

B is hydrogen.

$G^3$ is an optionally halogen-, cyano-, methyl-, methoxy-, trifluoromethyl-, amino- or dimethylamino-substituted radical from the group of

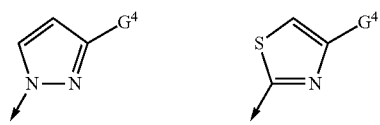

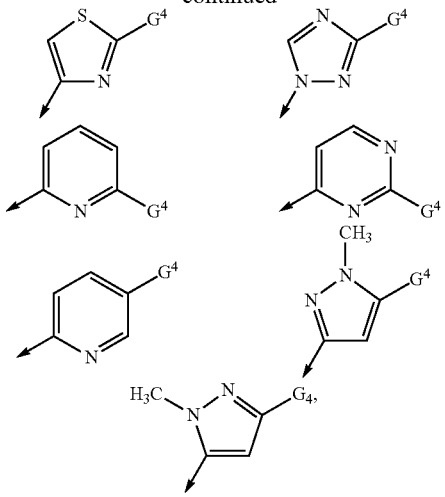

in which the arrow in each case marks the bond to $G^2$, and $G^4$ is also shown for illustration.

$G^4$ is a radical from the group of

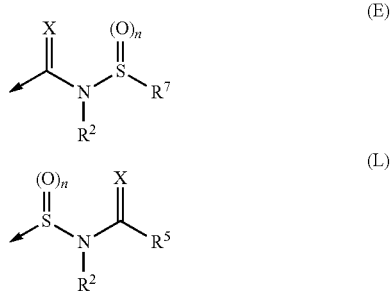

and in the case of the heterocycles (A) and (B) is also the radical

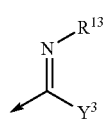

in which the arrow in each case marks the bond to $G^3$.

X is oxygen.

n is 2.

$R^2$ is a radical from the group of hydrogen, $C_1$-$C_4$-alkyl, $C_2$-$C_4$-alkynyl, cyano-$C_1$-$C_4$-alkyl and $C_1$-$C_4$-alkoxy-$C_1$-$C_4$-alkyl, optionally halogen-substituted $C_1$-$C_4$-alkylcarbonyl or $C_1$-$C_4$-alkylsulfonyl, optionally halogen-substituted $C_1$-$C_4$-alkoxycarbonyl, optionally halogen-, $C_1$-$C_4$-alkyl-, $C_1$-$C_4$-alkoxy-, $C_1$-$C_4$-halogenalkyl- and cyano-substituted $C_3$-$C_6$-cycloalkylcarbonyl, or a cation, for example a mono- or divalent metal ion or an optionally $C_1$-$C_4$-alkyl- or aryl-$C_1$-$C_4$-alkyl-substituted ammonium ion; $R^2$ is especially a radical from the group of hydrogen, methyl, ethyl, $CH_2OCH_3$, $CH_2OCH_2CH_3$, $COCH_3$, $COCH_2CH_3$, $CH_2CN$, propynyl, cyclopropyl, $Na^+$, $K^+$ and $^+N(CH_3)_4$.

$R^5$ is a radical from the group of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl, $C_1$-$C_4$-haloalkyl-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl, in which the rings may contain at least one heteroatom from the group of sulphur, oxygen (where oxygen atoms must not be immediately adjacent) and nitrogen (and is especially

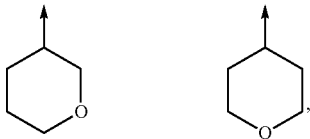

where the arrow in each case marks the bond to the carbon atom in the (L) radical), in each case optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl, or NR'R" in which R' and R" are each independently a radical from the group of hydrogen and $C_1$-$C_1$-alkyl, and $R^5$ is especially a radical from the group of methyl, ethyl, i-propyl, $CF_3$, $CHF_2$, $CH_2F$, $CH_2CF_3$, cyclopropyl, dimethylamino, diethylamino, phenyl and benzyl.

$R^7$ is a radical from the group of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl, in which the rings may contain at least one heteroatom from the group of sulphur, oxygen (where oxygen atoms must not be immediately adjacent) and nitrogen (and is especially

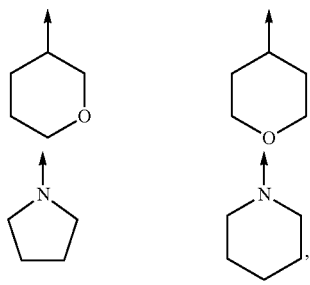

where the arrow in each case marks the bond to the sulphur atom in the (E) radical), in each case optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkylamino-, di($C_1$-$C_4$-alkylamino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl, or NR'R" in which R' and R" are each independently a radical from the group of hydrogen and $C_1$-$C_4$-alkyl, and $R^7$ is especially a radical from the group of methyl, ethyl, i-propyl, $CF_3$, $CHF_2$, $CH_2F$, $CH_2CF_3$, cyclopropyl, dimethylamino, diethylamino, phenyl and benzyl.

$R^{13}$ is a radical from the group of hydrogen, $C_1$-$C_4$-alkyl, $C_1$-$C_4$-haloalkyl, cyano, $C_1$-$C_4$-cyanoalkyl, $C_1$-$C_4$-hydroxyalkyl, hydroxyl, $C_1$-$C_4$-alkoxy, $C_1$-$C_4$-alkoxy-$C_1$-$C_4$-alkyl, $C_1$-$C_4$-alkylthio-$C_1$-$C_4$-alkyl, $C_2$-$C_4$-alkenyl, $C_2$-$C_4$-haloalkenyl, $C_2$-$C_4$-cyanoalkenyl, $C_2$-$C_4$-alkynyl, $C_2$-$C_4$-haloalkynyl, $C_2$-$C_4$-cyanoalkynyl, $C_1$-$C_5$-alkylcarbonyl and $C_1$-$C_5$-alkoxycarbonyl.

$Y^3$ is a radical from the group of $C_1$-$C_4$-alkoxy, $C_1$-$C_4$-haloalkoxy, $C_1$-$C_4$-allylthio, $C_1$-$C_4$-haloalkylthio and $NR^{14}R^{15}$ where $R^{14}$ and $R^{15}$ are each independently a radical from the group of hydrogen, $C_1$-$C_4$-alkyl, $C_3$-$C_6$-cycloalkyl, $C_3$-$C_6$-cycloalkyl-$C_1$-$C_4$-alkyl, $C_1$-$C_4$-haloalkyl, cyano, $C_1$-$C_4$-cyanoalkyl, hydroxyl, $C_1$-$C_4$-alkoxy, $C_1$-$C_4$-haloalkoxy, $C_1$-$C_4$-hydroxyalkyl, $C_1$-$C_4$-alkylthio-$C_1$-$C_4$-alkyl, $C_2$-$C_4$-alkenyl, $C_2$-$C_4$-haloalkenyl, $C_2$-$C_4$-cyanoalkenyl, $C_2$-$C_4$-alkynyl, $C_2$-$C_4$-haloalkynyl, $C_2$-$C_4$-cyanoalkynyl, $C_1$-$C_5$-alkylcarbonyl and $C_1$-$C_5$-alkoxycarbonyl, or $R^{14}$ and $R^{15}$ together with the nitrogen atom to which they are bonded may form an optionally halogen-, cyano-, $C_1$-$C_4$-alkyl-, $C_1$-$C_4$-haloalkyl-, $C_3$-$C_6$-cycloalkyl- or $C_1$-$C_4$-thioalkyl-substituted saturated or unsaturated five- to six-membered ring which may contain a further atom from the group of sulphur, oxygen and nitrogen and/or a carbonyl group; $R^{14}$ and $R^{15}$ together with the nitrogen atom to which they are bonded may especially be a radical from the group of

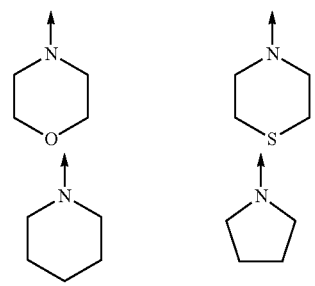

(in which the arrow in each case marks the bond to the carbon atom in the (N) radical).

In the preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl, and is preferably in turn phenyl, hetaryl (synonymous with heteroaryl, including as part of a larger unit, for example hetarylalkyl) is selected from the group of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, 5-membered heterocyclyl is a partially saturated 5-membered ring which contains 1 or 2 nitrogen atoms and/or one oxygen atom and/or one sulphur atom, 6-membered heterocyclyl is a partially saturated 6-membered ring which contains 1 or 2 nitrogen atoms and/or one oxygen atom and/or one sulphur atom.

In the particularly preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl, and is preferably in turn phenyl, hetaryl (including as part of a larger unit, for example hetarylalkyl) is selected from the group of pyridyl, pyrimidyl, oxadiazolyl, oxazolyl, pyrazinyl, imidazolyl, thiazolyl, thiadiazolyl and furanyl.

In the very particularly preferred definitions, unless stated otherwise, aryl is phenyl and hetaryl (equivalent to heteroaryl, including as part of a larger unit, for example hetarylalkyl) is a radical selected from the group of pyrazolyl, oxazolyl, thiazolyl, pyridyl, pyrimidinyl, pyridazinyl and pyrazinyl.

Halogen-substituted radicals, for example haloalkyl, mono- or polyhalogenate, up to the maximum number of possible substituents. In the case of polyhalogenation, the halogen atoms may be identical or different. In this case, halogen is fluorine, chlorine, bromine or iodine, especially fluorine, chlorine or bromine.

Saturated or unsaturated hydrocarbyl radicals, such as alkyl or alkenyl, may in each case be straight-chain or branched as far as possible, including in combination with heteroatoms, as, for example, in alkoxy.

Optionally substituted radicals may be mono- or polysubstituted, where the substituents in the case of polysubstitution may be the same or different.

In the radicals (A), (B), (C) and (D) that $G^2$ can represent, the arrow in each case marks the bond to the adjacent ring.

In an emphasized group of inventive compounds, $G^2$ is the radical (A).

In a further emphasized group of inventive compounds, $G^2$ is the radical (B).

In a further emphasized group of inventive compounds, $G^2$ is the radical (C).

In a further emphasized group of inventive compounds, $G^2$ is the radical (D).

In a further emphasized group of inventive compounds, X is oxygen.

In a further emphasized group of inventive compounds, X is sulphur.

In a further emphasized group of inventive compounds, $G^1$ is C—H.

In a further emphasized group of inventive compounds, $G^1$ is C—F.

In a further emphasized group of inventive compounds, $G^1$ is N (nitrogen).

In a further emphasized group of inventive compounds, $A^1$ is hydrogen.

In a further emphasized group of inventive compounds, $A^2$ is hydrogen.

In a further emphasized group of inventive compounds, n is 2.

In a further emphasized group of inventive compounds, $R^1$ is hydrogen.

In a further emphasized group of inventive compounds, $R^1$ is methyl.

In a further emphasized group of inventive compounds, $R^1$ is fluorine.

In a further emphasized group of inventive compounds, $G^4$ is the radical (E).

In a further emphasized group of inventive compounds, $G^4$ is the radical (I).

In a further emphasized group of inventive compounds, $G^4$ is the radical (L).

In a further emphasized group of inventive compounds, $G^4$ is the radical (N).

In a further emphasized group of inventive compounds, $G^3$ is a pyrazolyl radical.

In a further emphasized group of inventive compounds, $G^3$ is a thiazolyl radical.

In a further emphasized group of inventive compounds, $G^3$ is a triazolyl radical.

In a further emphasized group of inventive compounds, $G^3$ is a pyridinyl radical.

In a further emphasized group of inventive compounds, $G^3$ is a pyrimidinyl radical.

An emphasized embodiment of the invention relates to compounds of the formula (IA)

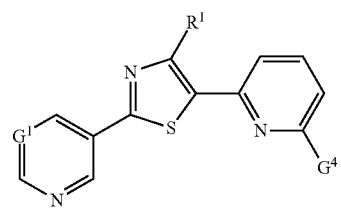

(IA)

in which $G^1$ is C—H, C—F, C—Cl or N, $R^1$ is hydrogen or methyl and $G^4$ is one of the (E), (L) and (N) radicals and especially the (E) radical.

A group of compounds preferred among the compounds of the formula (IA) are those in which $G^1$ is C—F, $R^1$ is hydrogen and $G^4$ is the (E) radical.

A further emphasized embodiment of the invention relates to compounds of the formula (IB)

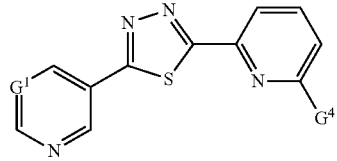

in which
G¹ is C—H, C—F, C—Cl or N and
G⁴ is one of the (E), (L) and (N) radicals.

A further emphasized embodiment of the invention relates to compounds of the formula (IC)

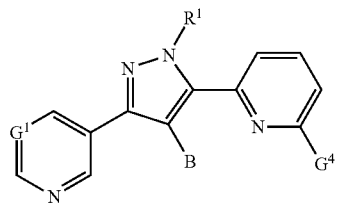

in which
G¹ is C—H, C—F, C—Cl or N,
R¹ is hydrogen or methyl,
B is hydrogen and
G⁴ is one of the (E), (L) and (N) radicals.

A further emphasized embodiment of the invention relates to compounds of the formula (ID)

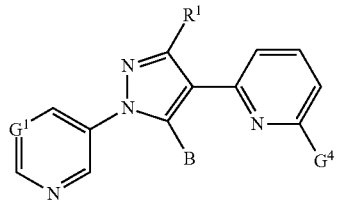

in which
G¹ is C—H, C—F, C—Cl or N,
R¹ is hydrogen or methyl,
B is hydrogen and
G⁴ is one of the (E) and (L) radicals.

The substituents in the (E), (L) and (N) radicals in the compounds of the formulae (IA), (IB), (IC) and (ID) may each assume the definitions specified in the description above.

The radical definitions or illustrations given above in general terms or within areas of preference apply to the end products of the formula (I) (and hence to the compounds of the formulae (Ia), (Ib), (IA), (IB), (IC) and (ID)) and correspondingly to starting materials and intermediates. These radical definitions can be combined with one another as desired, i.e. including combinations between the respective preferred ranges.

Preference is given in accordance with the invention to compounds of the formula (I) in which a combination of the definitions listed above as preferred is present.

Particular preference is given in accordance with the invention to compounds of the formula (I) in which a combination of the definitions listed above as particularly preferred is present.

Very particular preference is given in accordance with the invention to compounds of the formula (I) in which a combination of the definitions listed above as very particularly preferred is present.

The preparation of the inventive compounds is explained in detail hereinafter.

The compounds of the formula (II₁), (II₂), (II₃), (II₄) and (II₅) in which G² represents the radicals (A), (B) and (C), which are required as starting materials, can be prepared analogously to the methods described in WO 2010/006713 A2.

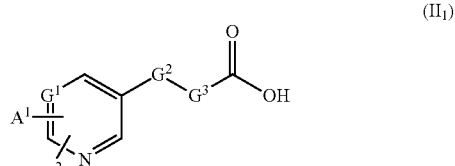

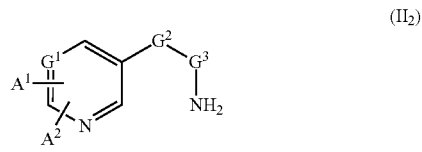

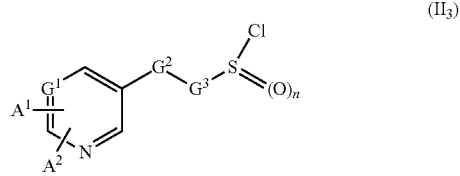

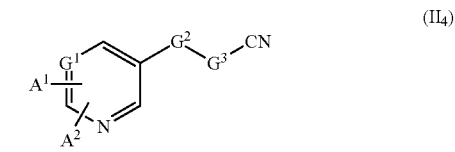

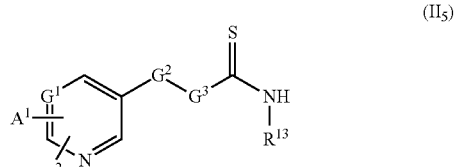

The starting compounds of the formula (II₁), (II₃), (II₃), (II₄) and (II₅) in which G² represents the radical (D), which are required as starting materials, can be prepared analogously to the methods described in the literature, as follows.

Reaction scheme 1

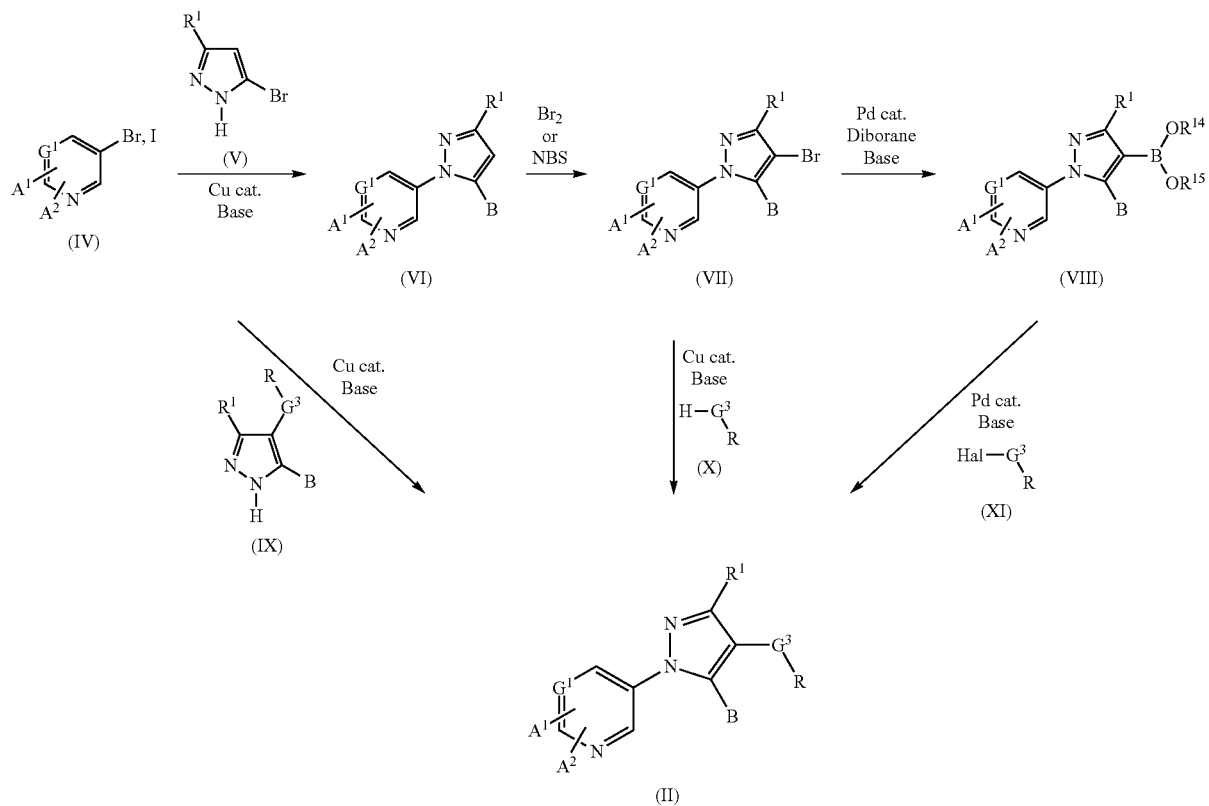

For example, reaction of a bromide of the formula (IV) with a pyrazole of the formula (V) in the presence of a copper catalyst and of a base such as potassium carbonate gives the compounds of the formula (VI). See, for example, for 3-(4-bromopyrazol-1-yl)pyridine: Journal of Heterocyclic Chemistry 1981, 18, 9-14; European Journal of Organic Chemistry, 2004, 695. These pyrazoles of the formula (VI) are used to obtain, by reaction with bromine or N-bromosuccinimide, the bromides of the formula (VII). See, for example, for 3-(4-bromopyrazol-1-yl)pyridine: Journal of Heterocyclic Chemistry 18, 1981, 9-14. The bromides of the formula (VII) are used to obtain, by reaction with, for example, bis(pinacolato) diborane in the presence of a palladium catalyst and of a base, the boronic esters of the formula (VIII). The starting compounds of the formula (II) required can be obtained from the bromides of the formula (VII) by reaction with a compound of the formula (X), which constitutes an H-G$^3$-R unit which contains an N—H, for example a pyrazole, in the presence of a copper catalyst and of a base, or according to the same process by reaction of the bromides of the formula (IV) with a suitable pyrazole of the formula (IX).

In addition, inventive compounds of the formula (I) can be obtained by reaction of the boronic esters of the formula (VIII) with a halide of the formula (XI) in the presence of a palladium catalyst and of a base (Suzuki reaction).

When R is a protected carboxylic acid, for example an ester, the carboxylic acid (II$_1$) can be prepared easily by known methods.

When R is a protected amine, the amine (II$_2$) can be prepared easily by known methods.

When R is halogen, for example bromine, (analogously to WO2007/45588 A1 and US2008/318941), the halogen can be exchanged for a metal, for example lithium. The metal compound reacts with sulphur dioxide and then with a chlorinating reagent such as sulphuryl chloride or N-chlorosuccinimide to give the starting compound (II$_3$).

Reaction scheme 2

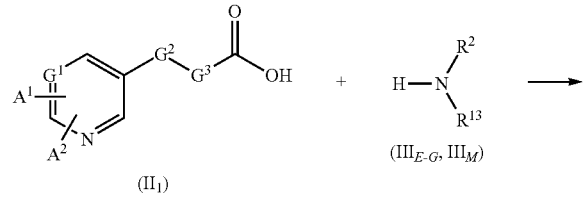

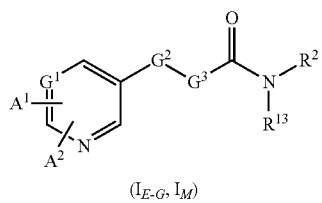

(I$_{E-G}$, I$_M$)

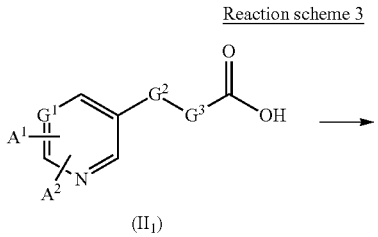

Reaction scheme 3

(II$_1$)

where R$^{13}$ is

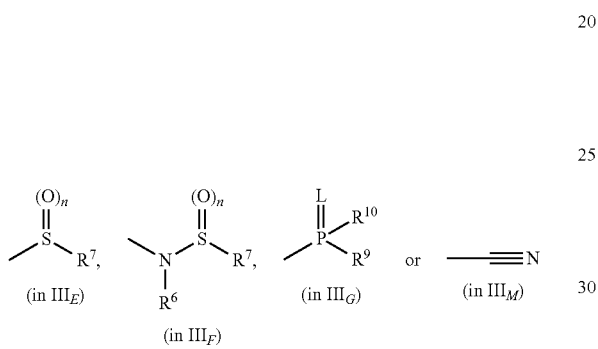

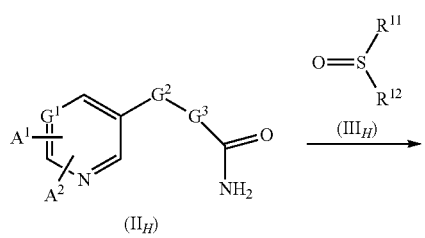

(II$_H$)

The amine derivatives of the formula (III$_{E-G}$, III$_M$) required as starting materials are known or can be prepared by methods known in principle.

The acids of the formula (II$_1$) can be reacted, after activation, for example to give the acid chloride (see, for example, Bioorg & MedChem Letters 15, 4354 (2005)), or by means of activating reagents such as CDI (carbonyldiimidazole; see, for example, Bioorg & MedChem 9, 1543 (2001), EDC (1-ethyl-3-[3-dimethylaminopropyl]carbodiimide hydrochloride) in the presence of DMAP (dimethylaminopyridine; see, for example, J. Med. Chem. 50, 3101 (2007)), or DCC (dicyclohexylcarbodiimide) in the presence of HOBT (1-hydroxybenzotriazole; see, for example, J. Med. Chem. 50, 3101 (2007)), with sulphonamides of the formula (III$_E$), optionally in the presence of a base such as a metal hydride (especially sodium hydride) or DBU (diazabicycloundecene), to give the inventive compounds of the formula (I$_E$) in which X is oxygen.

The further radicals mentioned for R$^{13}$ can be prepared from the acids of the formula (II$_1$) or the acid chlorides thereof by means of literature methods, or analogously to these methods, for example reacted with compounds of the formula (III$_F$) according to Chem. Letters 36, 1370 (2007) or J. Med. Chem. 29, 1299 (1986) to give the inventive compounds of the formula (I$_F$), or, for example, with compounds of the formula (III$_G$) according to J. Org. Chem. 72, 465 (2007) or Phosphorus & Sulfur 20, 93 (1984) to give the inventive compounds of the formula (I$_G$) and, for example, with cyanamines of the formula (III$_M$) according to WO2006/002099 A2 to give the inventive compounds of the formula (I$_M$).

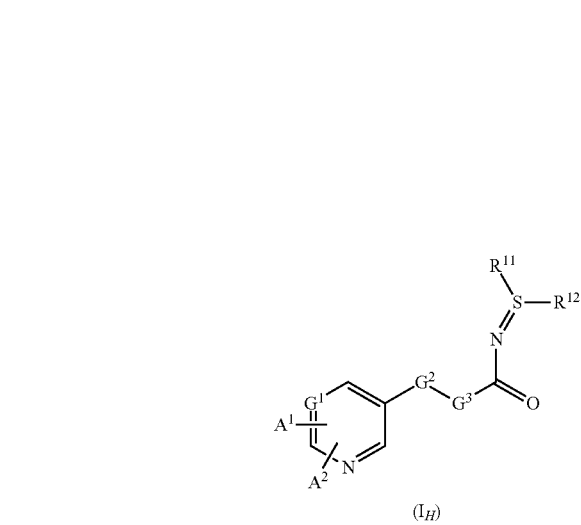

(I$_H$)

Compounds of the formula (I$_H$) can be prepared, for example, by reacting the carboxamides of the formula (II$_H$) with sulphoxides of the formula (III$_H$) by means of literature methods or analogous methods; see, for example, WO 2008/154528 A2.

The carboxamides of the formula (II$_H$) required as starting materials can be prepared from the acids (II$_1$) or the acid chlorides by means of literature methods or analogous methods, for example as described in WO 2007/103755 A2 or US 2009/203657 A1.

The sulphoxides of the formula (III$_H$) are compounds known from the literature.

Reaction scheme 4

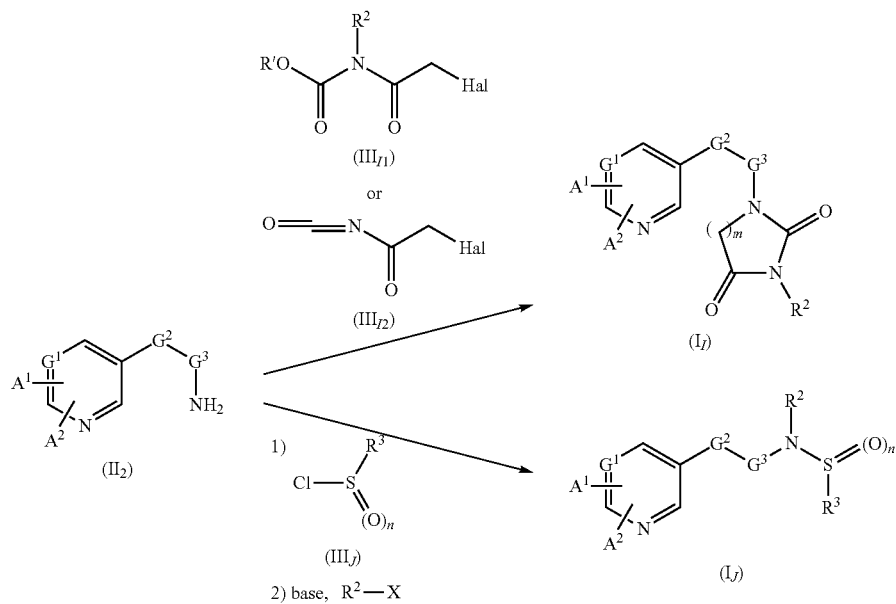

Compounds of the formula (I₁) can be prepared, for example, by reacting the amines of the formula (II₂) with compounds of the formula (III_{I1}) or (III_{I2}), analogously to the methods described in WO2007/132475 A1 or WO2006/019831 A1.

The compounds of the formula (III_{I1}) and (III_{I2}) are known or can be prepared by methods known in principle.

Compounds of the formula (I_J) can be prepared, for example, by reacting, heterocyclic amines of the formula (II₂) with sulphonyl chlorides of the formula (III_J) in the presence of a base, for example pyridine or sodium hydroxide; cf., for example, WO 2007/114532 A1 and US 2006/211603 A1.

The chlorosulphinyl or chlorosulphonyl derivatives of the formula (III_J) required as starting materials are known or can be prepared by methods known in principle.

Reaction scheme 5

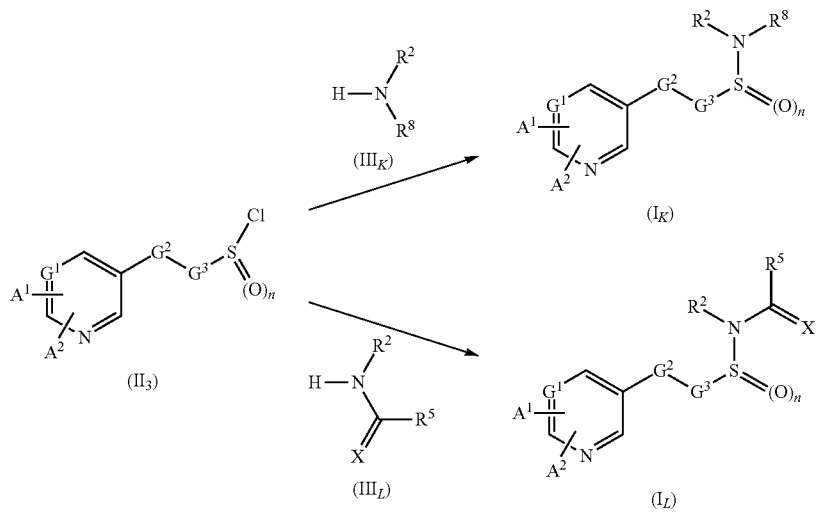

Compounds of the formula ($I_K$) can be prepared, for example, by reacting the sulphonyl chlorides of the formula ($II_3$) with amines of the formula ($III_K$), optionally in the presence of a base, for example pyridine or triethylamine, analogously to the methods described in U.S. Pat. No. 6,265,411, WO 2007/114532 A1 or U.S. Pat. No. 6,673,817.

The amines of the formula ($III_K$) required as starting materials are known or can be prepared by methods known in principle.

Compounds of the formula ($I_L$) in which X is oxygen can be prepared, for example, by reacting sulphonyl chlorides of the formula ($II_3$) with amides of the formula ($III_L$) in the presence of a base, for example sodium hydride or n-butyllithium, analogously to the methods described in US2004/006143 or Org. Let. 3458-3461 (2009).

The amides of the formula ($III_L$) required as starting materials are known or can be prepared by methods known in principle.

Reaction scheme 6

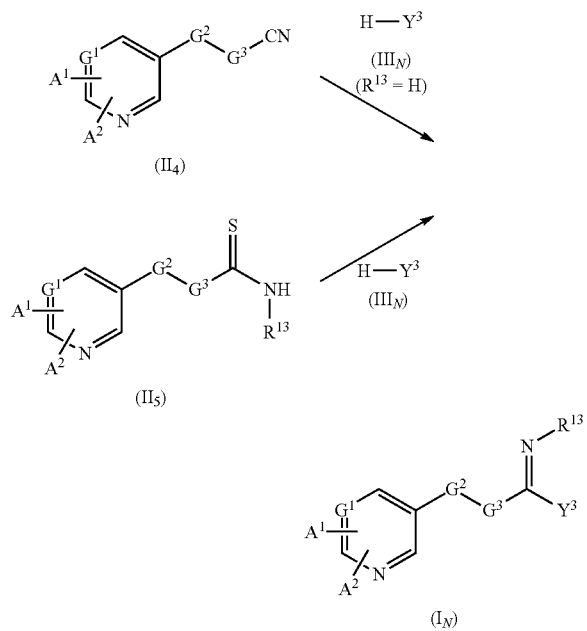

Compounds of the formula ($I_N$) can be prepared, for example, by reaction of nitriles of the formula ($II_4$) or thio amides of the formula ($II_5$) with oxy, thio or amino derivatives of the formula ($III_N$). Oxy derivatives can be used, for example, by the methods described in European Journal of Medicinal Chemistry 2009, 44(6), 2497-2505; thio derivatives can be used, for example, by the methods described in Journal of the America Chemical Society 1985, 107(28), 5745-5754. Amino derivatives can be used, for example, by the methods described in Bioorganic & Medicinal Chemistry Letter 2010, 20(1), 299-301, WO2007/083239 A1 or European Journal of Medicinal Chemistry 2010, 45(3), 902-908.

The compounds of the formula ($III_N$) required as starting materials are known or can be prepared by methods known in principle.

Compounds of the formula ($I_{E-H}$), ($I_1$) and ($I_L$) in which X is sulphur can be prepared from the corresponding compounds of the formula ($I_{E-H}$), ($I_1$) and ($I_L$) in which X is oxygen by reaction with a thionating reagent. The sulphiding agents (thionating reagents) used are preferably phosphorus reagents, for example diphosphorus pentasulphide ($P_2S_5$), diphosphorus pentasulphide/pyridine ($P_2S_5$/PY), diphosphorus pentasulphide/triethylamine ($P_2S_5$/NEt$_3$), diphosphorus pentasulphide/sodium hydrogencarbonate ($P_2S_5$/NaHCO$_3$ "Scheeren's reagent"), or more preferably 2,4-bis(4-methoxyphenyl)-2,4-dithioxo-1,3,2,4-dithiadiphosphetane "Lawesson's Reagent (LR)", 2,4-bis(4-phenoxyphenyl)-2,4-dithioxo-1,3,2,4-dithiadiphosphetane "Belleau's reagent (BR)" or 2,4-bis(4-phenylthiophenyl)-2,4-dithioxo-1,3,2,4-dithiadiphosphetane.

N-Oxides can be obtained, for example, by reacting compounds of the formula (I) with mCPBA (meta-chloroperbenzoic acid). Salts of compounds of the formula (I) are obtainable by reacting compounds of the formula (I) with compounds of the formula RX in which X is, for example, halogen such as chlorine or bromine and R is, for example, an in each case optionally substituted alkyl, alkenyl or alkynyl radical.

The intermediates of the formulae (XII), (XIII), (XIV), (XV), (XVI), (XVII) and (XVIII) which follow are novel and also form part of the subject-matter of the invention.

Compounds of the formula (XII)

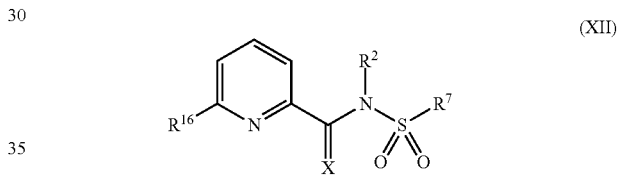

in which $R^{16}$ is fluorine, chlorine, bromine or iodine (especially chlorine, bromine or iodine) and X, $R^2$ and R are each as defined above.

Particular mention should be made of the following compounds of the formula (XII).

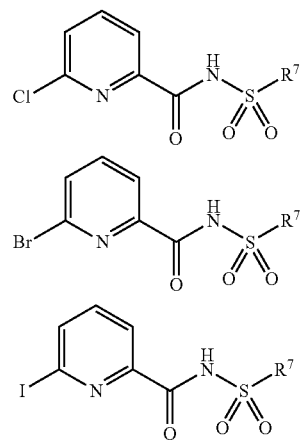

where $R^7$ is methyl, ethyl, cyclopropyl, $CF_3$, $CH_2CF_3$, dimethylamino, diethylamino, phenyl or benzyl.

Compounds of the formula (XIII)

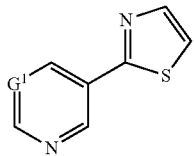
(XIII)

in which G¹ is nitrogen, C-halogen, C-cyano, C-nitro, C-alkyl, C-cycloalkyl or C-alkoxy, preferably nitrogen, C-halogen, C-cyano, C-nitro, C—$C_1$-$C_6$-alkyl, C—$C_3$-$C_6$-cycloalkyl or C—$C_1$-$C_6$-alkoxy.

Particular mention should be made of the following compounds of the formula (XIII).

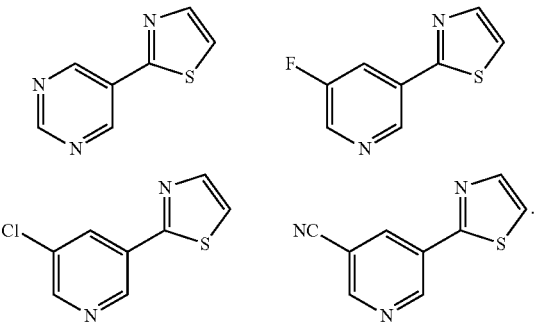

Compounds of the formula (XIV)

(XIV)

in which $R^{16}$ is fluorine, chlorine, bromine or iodine (especially chlorine, bromine or iodine) and X, $R^2$ and $R^5$ are each as defined above.

Particular mention should be made of the following compounds of the formula (XIV):

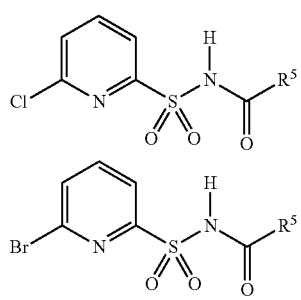

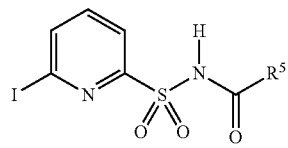

where $R^5$ is a radical from the group of methyl, ethyl, i-propyl, $CF_3$, $CHF_2$, $CH_2F$, $CH_2CF_3$, cyclopropyl, dimethylamino, diethylamino, phenyl and benzyl.

Compounds of the formula (XV)

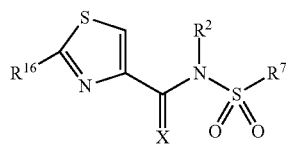
(XV)

in which $R^{16}$ is fluorine, chlorine, bromine or iodine (especially chlorine, bromine or iodine) and X, $R^2$ and $R^7$ are each as defined above.

Particular mention should be made of the following compounds of the formula (XV):

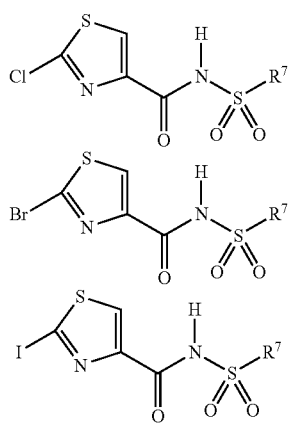

where $R^7$ is methyl, ethyl, cyclopropyl, $CF_3$, $CH_2CF_3$, dimethylamino, diethylamino, phenyl or benzyl.

Compounds of the formula (XVI)

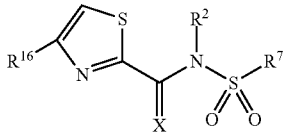
(XVI)

in which $R^{16}$ is fluorine, chlorine, bromine or iodine (especially chlorine, bromine or iodine) and X, $R^2$ and $R^7$ are each as defined above.

Particular mention should be made of the following compounds of the formula (XVI):

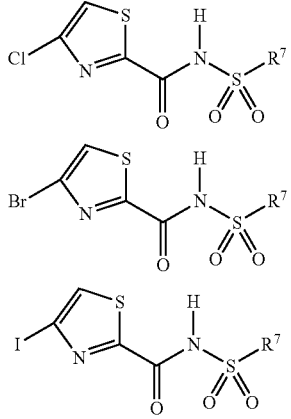

where R⁷ is as defined above and is especially methyl, ethyl, cyclopropyl, CF₃, CH₂CF₃, dimethylamino, diethylamino, phenyl or benzyl.

Compounds of the formula (XVII)

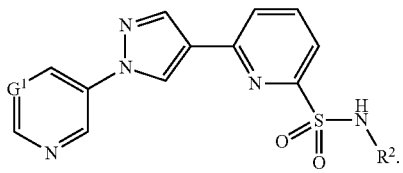

in which
G¹ is nitrogen, C-halogen, C-cyano, C-nitro, C-alkyl, C-cycloalkyl or C-alkoxy, preferably nitrogen, C-halogen, C-cyano, C-nitro, C—C₁-C₆-alkyl, C—C₃-C₆-cycloalkyl or C—C₁-C₆-alkoxy and
R² is as defined above.

Particular mention should be made of the following compounds of the formula (XVII).

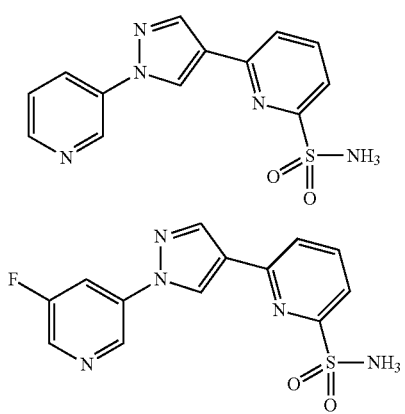

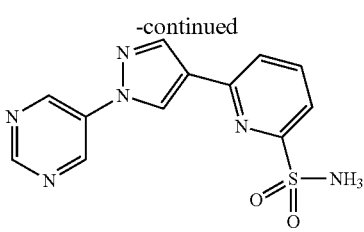

Compounds of the formula (XVIII)

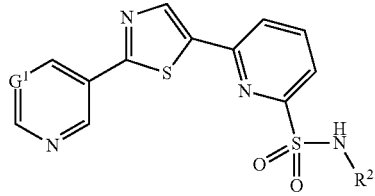

in which
G¹ is nitrogen, C-halogen, C-cyano, C-nitro, C-alkyl, C-cycloalkyl or C-alkoxy, preferably nitrogen, C-halogen, C-cyano, C-nitro, C—C₁-C₆-alkyl, C—C₃-C₆-cycloalkyl or C—C₁-C₆-alkoxy and
R² is as defined above.

Particular mention should be made of the following compounds of the formula (XVIII):

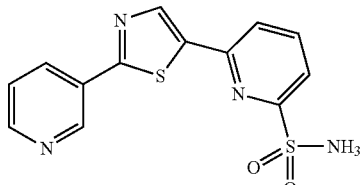

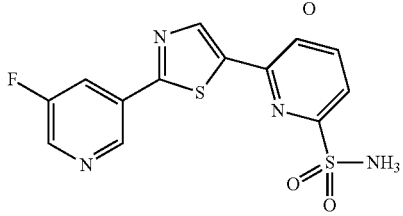

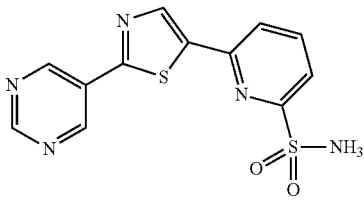

The inventive active ingredients, given good plant tolerance, favourable homeotherm toxicity and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection compositions. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp. *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Anon* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus Maria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti*.

It is also possible to control protozoa, such as *Eimeria*.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Dias is* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella firrcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis* and *Vespa* spp.

From the order of the Isopoda, for example, *Armadillidium vulgare, Oniscus asellus* and *Porcellio scaber*.

From the order of the Isoptera, for example, *Reticulitermes* spp. and *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola biselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria*.

From the order of the Siphonaptera, for example, *Ceratophyllus* spp. and *Xenopsylla* cheopis.

From the order of the Symphyla, for example, *Scutigerella immaculata*.

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni* and *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans* and *Xiphinema* spp.

The inventive compounds can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). They can also be used as intermediates or precursors for the synthesis of further active ingredients.

The active ingredients can be converted to the customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active ingredient, synthetic substances impregnated with active ingredient, fertilizers and also microencapsulations in polymeric substances.

These formulations are produced in a known manner, for example by mixing the active ingredients with extenders, that is, liquid solvents and/or solid carriers, optionally with the use of surfactants, that is to say emulsifiers and/or dispersants and/or foam-formers. The formulations are prepared either in suitable facilities or else before or during application.

The auxiliaries used may be those substances which are suitable for imparting particular properties to the composition itself and/or to preparations derived therefrom (for example spray liquors, seed dressings), such as certain technical properties and/or also particular biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents essentially include: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Useful solid carriers include:
for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, maize cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Additionally suitable are oligo- or polymers, for example those derived from vinylic monomers, from acrylic acid, from EO and/or PO alone or in combination with, for example, (poly)alcohols or (poly)amines. It is also possible to use lignin and its sulphonic acid derivatives, unmodified and modified celluloses, aromatic and/or aliphatic sulphonic acids and also their adducts with formaldehyde.

In the formulations it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Further additives may be perfumes, mineral or vegetable, optionally modified oils, waxes and nutrients (including trace nutrients), such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability.

The formulations contain generally between 0.01 and 98 percent by weight of active ingredient, preferably between 0.5 and 90%.

The inventive active ingredients may also be present, as such or in their formulations, in a mixture with one or more suitable fungicides, bactericides, acaricides, nematicides, insecticides, microbicides, fertilizers, attractants, sterilants, synergists, safeners, semiochemicals and/or plant growth regulators, in order thus to broaden the spectrum of activity, to prolong the duration of action, to increase the speed of action, to prevent repellency or to preclude the development of resistance. In addition, such combinations can improve plant growth, increase tolerance to high or low temperatures, to drought or to water content or soil salinity, enhance flowering performance, facilitate harvesting and increase yields, accelerate ripening, increase quality and/or the nutritional value of the harvested products, prolong storage life and/or improve the processability of the harvested products. In general, combination of the inventive active ingredients and mixing partners gives synergistic effects, which means that the efficacy of the particular mixture is greater than the efficacy of the individual components. It is generally possible to use the combinations either as seed applications or in premixes, tankmixes or readymixes.

Particularly favourable mixing partners are, for example, the following:

Insecticides/Acaricides/Nematicides:

The active ingredients identified here by their common name are known and are described, for example, in the pesticide handbook ("The Pesticide Manual" 14th Ed., British Crop Protection Council 2006) or can be found on the Internet (e.g. http://www.alanwood.net/pesticides).

(1) Acetylcholinesterase (AChE) inhibitors, for example
carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or
organophosphates, for example acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion.

(2) GABA-gated chloride channel antagonists, for example
cyclodiene-organochlorines, for example chlordane and endosulfan; or
phenylpyrazoles (fiproles), for example ethiprole and fipronil.

(3) Sodium channel modulators/voltage-dependent sodium channel blockers, for example
pyrethroids, for example acrinathrin, allethrin, d-cis-trans allethrin, d-trans allethrin, bifenthrin, bioallethrin, bioallethrin S-cyclopentenyl isomer, bioresmethrin, cyclopro-thrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomers], deltamethrin, empenthrin [(EZ)-(1R)-isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans-isomer], prallethrin, pyrethrins (pyrethrum), resmethrin, silafluofen, tefluthrin, tetramethrin, tetramethrin [(1R)-isomers], tralomethrin and transfluthrin; or
DDT; or methoxychlor.

(4) Nicotinergic acetylcholine receptor (nAChR) agonists, for example
neonicotinoids, for example acetamiprid, clothianidin, dinotefuran, imidacloprid, nitenpyram, thiacloprid and thiamethoxam; or
nicotine.

(5) Nicotinergic acetylcholine receptor (nAChR) allosteric activators, for example
spinosins, for example spinetoram and spinosad.

(6) Chloride channel activators, for example
avermectins/milbemycins, for example abamectin, emamectin benzoate, lepimectin and milbemectin.

(7) Juvenile hormone imitators, for example
Juvenile hormone analogues, for example hydroprene, kinoprene and methoprene; or fenoxycarb or pyriproxyfen.

(8) Active ingredients with unknown or nonspecific mechanisms of action, for example
alkyl halides, for example methyl bromide and other alkyl halides; or
chloropicrin; or sulphuryl fluoride; or borax; or tartar emetic.

(9) Selective antifeedants, for example pymetrozine; or flonicamid.

(10) Mite growth inhibitors, for example clofentezine, hexythiazox and diflovidazin; or etoxazole.

(11) Microbial disruptors of the insect gut membrane, for example Bacillus thuringiensis subspecies *israelensis*, Bacillus sphaericus, Bacillus thuringiensis subspecies *aizawai*, Bacillus thuringiensis subspecies *kurstaki*, Bacillus thuringiensis subspecies *tenebrionis* and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron; or
organotin compounds, for example azocyclotin, cyhexatin and fenbutatin oxide; or
propargite; or tetradifon.

(13) Oxidative phosphorylation decouplers acting by interrupting the H proton gradient, for example chlorfenapyr, DNOC and sulfluramid.

(14) Nicotinergic acetylcholine receptor antagonists, for example bensultap, cartap-hydrochloride, thiocyclam and thiosultap-sodium.

(15) Chitin biosynthesis inhibitors, type 0, for example bistrifluoron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin;

(17) Moulting disruptors, dipteran, for example cyromazine;

(18) Ecdysone receptor agonists, for example chromafenozide, halofenozide, methoxyfenozide and tebufenozide.

(19) Octopaminergic agonists, for example amitraz;

(20) Complex-III electron transport inhibitors, for example hydramethylnone; or acequinocyl; or fluacrypyrim;

(21) Complex-I electron transport inhibitors, for example METI acaricides, for example fenazaquin, fenpyroximate, pyrimidifen, pyridaben, tebufenpyrad and tolfenpyrad; or rotenone (Derris).

(22) Voltage-dependent sodium channel blockers, for example indoxacarb; or metaflumizone.

(23) Inhibitors of acetyl-CoA carboxylase, for example tetronic and tetramic acid derivatives, for example spirodiclofen, spiromesifen and spirotetramat.

(24) Complex-IV electron transport inhibitors, for example phosphines, for example aluminium phosphide, calcium phosphide, phosphine and zinc phosphide; or cyanide.

(25) Complex-II electron transport inhibitors, for example cyenopyrafen.

(28) Ryanodine receptor effectors, for example diamides, for example chlorantraniliprole and flubendiamide.

Further active ingredients with unknown mechanism of action, for example amidoflumet, azadirachtin, benclothiaz, benzoximate, bifenazate, bromopropylate, chinomethionat, cryolite, cyantraniliprole (Cyazypyr), cyflumetofen, dicofol, diflovidazine, fluensulfone, flufenerim, flufiprole, fluopyram, flufenozide, imidaclothiz, iprodione, pyridalyl, pyrifluquinazon and iodomethane; and also products based on *Bacillus firmus* (1-1582, BioNeem, Votivo) and the following known active ingredients:

3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934), 4-{[(6-bromopyrid-3-yl)methyl](2-fluoroethyl)amino}furan-2(5H)-one (known from WO 2007/115644), 4-{[(6-fluoropyrid-3-yl)methyl](2,2-difluoroethyl)amino}furan-2(5H)-one (known from WO 2007/115644), 4-{[(2-chloro-1,3-thiazol-5-yl)methyl](2-fluoroethyl)amino}furan-2(5H)-one (known from WO 2007/115644), 4-{[(6-chloropyrid-3-yl)methyl](2-fluoroethyl)amino}furan-2(5H)-one (known from WO 2007/115644), 4-{[(6-chloropyrid-3-yl)methyl](2,2-difluoroethyl)amino}furan-2(5H)-one (known from WO 2007/115644), 4-{[(6-chloro-5-fluoropyrid-3-yl)methyl](methyl)amino}furan-2(5H)-one (known from WO 2007/115643), 4-{[(5,6-dichloropyrid-3-yl)methyl](2-fluoroethyl)amino}furan-2(5H)-one (known from WO 2007/115646), 4-{[(6-chloro-5-fluoropyrid-3-yl)methyl](cyclopropyl)amino}furan-2(5H)-one (known from WO 2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), {[1-(6-chloropyridin-3-yl)ethyl](methyl)oxido-$\lambda^4$-sulphanylidene}cyanamide (known from WO 2007/149134), and its diastereomers {[(1R)-1-(6-chloropyridin-3-yl)ethyl](methyl)oxido-$\lambda^4$-sulphanylidene}cyanamide (A) and {[(1S)-1-(6-chloropyridin-3-yl)ethyl](methyl)oxido-$\lambda^4$-sulphanylidene}cyanamide (B) (likewise known from WO2007/149134) and sulfoxaflor (likewise known from WO 2007/149134), and its diastereomers [(R)-methyl(oxido) {(1R)-1-[6-(trifluoromethyl)pyridin-3-yl]ethyl}-$\lambda^4$-sulphanylidene]cyanamide (A1) and [(S)-methyl(oxido) {(1S)-1-[6-(trifluoromethyl)pyridin-3-yl]ethyl}-$\lambda^4$-sulphanylidene] cyanamide (A2), designated as diastereomer group A (known from WO 2010/074747, WO 2010/074751), [(R)-methyl (oxido) {(1S)-1-[6-(trifluoromethyl)pyridin-3-yl]ethyl}$\lambda^4$-sulphanylidene]cyanamide (B1) and [(S)-methyl(oxido) {(1R)-1-[6-(trifluoromethyl)pyridin-3-yl]ethyl}-$\lambda^4$-sulphanylidene]cyanamide (B2), designated as diastereomer group B (likewise known from WO 2010/074747, WO 2010/074751) and 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), 1-{2-fluoro-4-methyl-5-[(2,2,2-trifluoroethyl)sulphinyl]phenyl}-3-(trifluoromethyl)-1H-1,2,4-triazole-5-amine (known from WO 2006/043635), [(3S,4aR,12R,12aS,12bS)-3-(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (known from WO 2008/066153), 2-cyano-3-(difluoromethoxy)-N,N-dimethylbenzenesulphonamide (known from WO2006/056433), 2-cyano-3-(difluoromethoxy)-N-methylbenzenesulphonamide (known from WO2006/100288), 2-cyano-3-(difluoromethoxy)-N-ethylbenzenesulphonamide (known from WO2005/035486), 4-(difluoromethoxy)-N-ethyl-N-methyl-1,2-benzothiazole-3-amine 1,1-dioxide (known from WO2007/057407), N-[1-(2,3-dimethylphenyl)-2-(3,5-dimethylphenyl)ethyl]-4,5-dihydro-1,3-thiazole-2-amine (known from WO2008/104503), {1'-[(2E)-3-(4-chlorophenyl)prop-2-en-1-yl]-5-fluorospiro[indole-3,4'-piperidine]-1(2H)-yl}(2-chloropyridin-4-yl) methanone (known from WO2003/106457), 3-(2,5-dimethylphenyl)-4-hydroxy-8-methoxy-1,8-diazaspro[4.5]dec-3-en-2-one (known from WO2009/049851), 3-(2,5-dimethylphenyl)-8-methoxy-2-oxo-1,8-diazaspiro[4.5]dec-3-en-4-yl-ethyl carbonate (known from WO2009/049851), 4-(but-2-yn-1-yloxy)-6-(3,5-dimethyl piperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl)malononitrile (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO2007/040280), 2-ethyl-7-methoxy-3-methyl-6-[(2,2,3,3-tetrafluoro-2,3-dihydro-1,4-benzodioxin-6-yl)oxy]-quinolin-4-ylmethyl carbonate (known from JP2008/110953), 2-ethyl-7-methoxy-3-methyl-6-[(2,2,3,3-tetrafluoro-2,3-dihydro-1,4-benzodioxin-6-yl)oxy]quinolin-4-yl acetate (known from JP2008/110953), PF1364 (CAS Reg. No. 1204776-60-2) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzo-nitrite (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2(5H)-one, 4-{[(6-chloropyridin-3-yl)methyl]-(ethyl)amino}-1,3-oxazol-2(5H)-one, 4-{[(6-chloropyridin-3-yl)methyl](methyl)amino}-1,3-oxazol-2(5H)-one (all known from WO2010/005692), NNI-0711 (known from WO2002096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO2002096882), methyl 2-[2-({[3-bromo-1-(3-chloropyridin-2-yl)-1H-pyrazol-5-yl]carbonyl}amino)-5-chloro-3-methylbenzoyl]-2-methyl-hydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)-benzoyl]-2-ethylhydrazinecarboxylate (known from WO2005/085216), (5RS,7RS;5RS,7SR)-1-(6-chloro-3-pyridylmethyl)-1,2,3,5,6,7-hexahydro-7-methyl-8-nitro-5-propoxyimdazo[1,2-a]pyridine (known from WO2007/101369), 2-{6-[2-(5-fluoropyridin-3-yl)-1,3-thiazol-5-yl]pyridin-2-yl}pyrimidine (known from WO2010/006713), 2-{6-[2-(pyridin-3-yl)-1,3-thiazol-5-yl]pyridin-2-yl}pyrimidine (known from WO2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]m ethyl}-1H-pyrazole-5-carboxamide (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO2010/069502) and N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO2010/069502).

In a preferred embodiment of the invention, a penetrant is additionally added to the crop protection compositions to enhance the action. Useful penetrants also include, for example, substances which promote the availability of the compounds of the formula (I) in the spray coating. These include, for example, mineral and vegetable oils. Useful oils include all mineral or vegetable oils—modified or otherwise—which are typically usable in agrochemical compositions. Examples include sunflower oil, rapeseed oil, olive oil, castor oil, colza oil, cornseed oil, cottonseed oil and soybean oil or the esters of the oils mentioned. Preference is given to rapeseed oil, sunflower oil and their methyl or ethyl esters, especially rapeseed oil methyl ester.

The concentration of penetrant in the inventive compositions can be varied within a wide range. In the case of a formulated crop protection composition, it is generally 1 to 95% by weight, preferably 1 to 55% by weight, more preferably 15-40% by weight. In the ready-to-use compositions (spray liquors), the concentrations are generally between 0.1 and 10 g/l, preferably between 0.5 and 5 g/l.

When used as insecticides, the inventive active ingredients may also be present in their commercially available formulations and in the use forms, prepared from these formulations, as a mixture with synergists. Synergists are compounds which enhance the action of the active ingredients, without any need for the synergist added to be active itself.

When used as insecticides, the inventive active ingredients may also be present in their commercially available formulations and in the use forms, prepared from these formulations, as a mixture with inhibitors which reduce degradation of the active ingredient after use in the environment of the plant, on the surface of parts of plants or in plant tissues.

The active ingredient content of the use forms prepared from the commercially available formulations may vary within wide limits. The active ingredient concentration of the application forms may be from 0.00000001 to 95% by weight of active ingredient, preferably between 0.00001 and 1% by weight.

The compounds are applied in a customary manner appropriate for the use forms.

The good plant compatibility of the active ingredients in the concentrations needed for control of plant diseases allows treatment of above-ground plant parts, of plants and seed, and of the soil.

The inventive treatment of the plants and plant parts with the active ingredients is effected directly or by allowing them to act on the surroundings, habitat or storage space by the customary treatment methods, for example by dipping, spraying, evaporating, fogging, scattering, painting on, injecting, and, in the case of propagation material, especially in the case of seeds, also by applying one or more coats.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant varieties which are protectable and non-protectable by plant breeders' rights. Parts of plants shall be understood to mean all above-ground and below-ground parts and organs of plants, such as shoot, leaf, flower and root, examples including leaves, needles, stems, trunks, flowers, fruit bodies, fruits and seeds, and also roots, tubers and rhizomes. The plant parts also include harvested material and vegetative and generative propagation material, for example cuttings, tubers, rhizomes, slips and seeds.

Plants which can be treated in accordance with the invention include the following: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Laztraceae* sp., *Musaceae* sp. (for example banana plants and banana plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cuma-bitaceae* sp. (for example cucumber), *Alliaceae* sp. (for example leeks, onions), *Papilionaceae* sp. (for example peas); major crop plants such as *Gramineae* sp. (for example maize, turf, cereals such as wheat, rye, rice, barley, oats, millet and triticale), *Poaceae* sp. (for example sugar cane), *Asteraceae* sp. (for example sunflower), *Brassicaceae* sp. (for example white cabbage, red cabbage, broccoli, cauliflower, Brussels sprouts, pak choi, kohlrabi, radishes, and also oilseed rape, mustard, horseradish and cress), *Fabacae* sp. (for example beans, peanuts), *Papilionaceae* sp. (for example soya beans), *Solanaceae* sp. (for example potatoes), *Chenopodiaceae* sp. (for example sugar beet, fodder beet, Swiss chard, beetroot); useful plants and ornamental plants in gardens and forests; and genetically modified types of each of these plants.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above. More preferably, plants of the plant cultivars which are each commercially available or in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The inventive treatment method can be used for the treatment of genetically modified organisms (GMOs), for example plants or seeds. Genetically modified plants (or transgenic plants) are plants in which a heterologous gene has been integrated stably into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene present in the genome is also called a transgene. A transgene that is defined by its specific presence in the plant genome is called a transformation or transgenic event.

Depending on the plant species or plant varieties, their location and growth conditions (soils, climate, vegetation period, diet), the treatment according to the invention may also result in superadditive ("synergistic") effects. For example, the following effects exceeding the effects actually to be expected are possible: reduced application rates and/or a widening of the activity spectrum and/or an increase in the activity of the active ingredients and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products.

At certain application rates, the inventive active ingredients may also have a fortifying effect on plants. They are therefore suitable for mobilizing the defence system of the plant against attack by unwanted phytopathogenic fungi and/or microorganisms and/or viruses. This may be one of the reasons for the enhanced activity of the inventive combinations, for example against fungi. Plant-fortifying (resistance-inducing) substances shall be understood to mean, in the present context, also those substances or combinations of substances which are capable of stimulating the defence system of plants in such a way that, when subsequently inoculated with unwanted phytopathogenic fungi, the plants treated display a substantial degree of resistance to these unwanted phytopathogenic fungi. The inventive substances can therefore be used for protection of plants from attack by the pathogens mentioned within a certain period of time after the treatment. The period within which protection is achieved generally extends for from 1 to 10 days, preferably 1 to 7 days, after the treatment of the plants with the active ingredients.

Plants and plant varieties which are preferably treated in accordance with the invention include all plants which have genetic material which imparts particularly advantageous, useful traits to these plants (whether obtained by breeding and/or biotechnological means).

Plants and plant varieties which are likewise preferably treated in accordance with the invention are resistant to one or more biotic stress factors, i.e. said plants have a better defence against animal and microbial pests, such as against nematodes, insects, mites, phytopathogenic fungi, bacteria, viruses and/or viroids.

Plants and plant varieties which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant varieties which can likewise be treated in accordance with the invention are those plants which are characterized by enhanced yield characteristics. Enhanced yield in these plants may be the result of, for example, improved plant physiology, improved plant growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processibility and better storage stability.

Plants that may be treated according to the invention are hybrid plants that already express the characteristics of heterosis, or hybrid effect, which results in generally higher yield, vigour, health and resistance towards biotic and abiotic stress factors. Such plants are typically produced by crossing an inbred male-sterile parent line (the female parent) with another inbred male-fertile parent line (the male parent). The hybrid seed is typically harvested from the male-sterile plants and sold to growers. Male-sterile plants can sometimes (for example in maize) be produced by detasseling (i.e. mechanical removal of the male reproductive organs or male flowers); however, it is more typical for male sterility to be the result of genetic determinants in the plant genome. In that case, and especially when seed is the desired product to be harvested from the hybrid plants, it is typically beneficial to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396, in which, for example, a ribonuclease such as a barnase is selectively expressed in the tapetum cells in the stamens. Fertility can then be restored by expression in the tapetum cells of a ribonuclease inhibitor such as barstar.

Plants or plant varieties (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are, for example, glyphosate-tolerant plants, i.e. plants which have been made tolerant to the herbicide glyphosate or salts thereof. For example, glyphosate-tolerant plants can be obtained by transforming the plant with a gene which encodes the enzyme 5-enolpyruvylshilcimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally occurring mutations of the abovementioned genes.

Other herbicide-resistant plants are for example plants that have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species). Plants expressing an exogenous phosphinothricin acetyltransferase have been described.

Further herbicide-tolerant plants are also plants that have been made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is converted to homogentisate. Plants tolerant to HPPD inhibitors can be transformed with a gene encoding a naturally occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme prephenate dehydrogenase in addition to a gene encoding an HPPD-tolerant enzyme.

Further herbicide-resistant plants are plants that have been made tolerant to acetolactate synthase (ALS) inhibitors. The known ALS inhibitors include, for example, sulphonylurea, imidazolinone, triazolopyrimidines, pyrimidinyl oxy(thio)benzoates and/or sulphonylaminocarbonyltriazolinone herbicides. Different mutations in the ALS enzyme (also known as acetohydroxy acid synthase, AHAS) are known to confer tolerance to different herbicides and groups of herbicides.

The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Other plants tolerant to imidazolinone and/or sulphonylurea can be obtained by induced mutagenesis, by selection in cell cultures in the presence of the herbicide or by mutation breeding.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation which imparts such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, such as the insecticidal crystal proteins compiled online at: http://www.lifesci.sussex.ac.uk/Home/Neil_Criclmore/Bt/, or insecticidal portions thereof, for example proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second other crystal protein than *Bacillus thuringiensis* or a portion thereof, such as the binary toxin made up of the Cy34 and Cy35 crystal proteins; or 3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or 4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR604; or 5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/Home/Neil_Crickmore/Bt/vip.html, for example proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins;

7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the abovementioned classes 1 to 8. In one embodiment, an insect-resistant plant contains more than one transgene encoding a protein of any one of the abovementioned classes 1 to 8, to expand the range of target insect species affected or to delay insect resistance development to the plants, by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:
a. plants which contain a transgene capable of reducing the expression and/or the activity of the poly(ADP-ribose) polymerase (PARP) gene in the plant cells or plants;
b. plants which contain a stress tolerance-enhancing transgene capable of reducing the expression and/or the activity of the PARG-encoding genes of the plants or plant cells;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which may also be treated according to the invention show altered quantity, quality and/or storage stability of the harvested product and/or altered properties of specific ingredients of the harvested product such as:
1) Transgenic plants which synthesize a modified starch which is altered with respect to its chemophysical traits, in particular the amylose content or the amylose/amylopectin ratio, the degree of branching, the average chain length, the distribution of the side chains, the viscosity behaviour, the gel resistance, the grain size and/or grain morphology of the starch in comparison to the synthesized starch in wild-type plant cells or plants, such that this modified starch is better suited for certain applications.
2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.
3) Transgenic plants which produce hyaluronan.

Plants or plant cultivars (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:
a) plants, such as cotton plants, which contain an altered form of cellulose synthase genes;
b) plants, such as cotton plants, which contain an altered form of rsw2 or rsw3 homologous nucleic acids;
c) plants, such as cotton plants, with an increased expression of sucrose phosphate synthase;
d) plants, such as cotton plants, with an increased expression of sucrose synthase;
e) plants, such as cotton plants, wherein the timing of the plasmodesmatal gating at the basis of the fibre cell is altered, for example through downregulation of fibre-selective β-1,3-glucanase;
f) plants, such as cotton plants, which have fibres with altered reactivity, for example through the expression of the N-acetylglucosaminetransferase gene including nodC and chitin synthase genes.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants containing a mutation imparting such altered oil characteristics and include:
a) plants, such as oilseed rape plants, which produce oil having a high oleic acid content;
b) plants, such as oilseed rape plants, which produce oil having a low linolenic acid content;
c) plants, such as oilseed rape plants, which produce oil having a low level of saturated fatty acids.

Particularly useful transgenic plants which may be treated according to the invention are plants which comprise one or more genes which encode one or more toxins are the transgenic plants which are sold under the following trade names: YIELD GARD® (for example maize, cotton, soya beans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaft10 (potato). Examples of herbicide-tolerant plants which should be mentioned are maize varieties, cotton varieties and soya bean varieties which are available under the following trade names: Roundup Ready® (tolerance to glyphosate, for example maize, cotton, soya beans), Liberty Link® (tolerance to phosphinothricin, for example oilseed rape); IMI® (tolerance to imidazolinone) and SCS® (tolerance to sulphonylurea, for example maize). Herbicide-resistant plants (plants bred in a conventional manner for herbicide tolerance) which should be mentioned include the varieties sold under the Clearfield® name (for example maize).

Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://www.agbios.com/dbase.php).

The plants listed can be treated in accordance with the invention in a particularly advantageous manner with the compounds of the general formula (I) and/or the active ingredient mixtures according to the invention. The preferred ranges stated above for the active ingredients or mixtures also apply to the treatment of these plants. Particular emphasis is given to the treatment of plants with the compounds or mixtures specifically mentioned in the present text.

The inventive active ingredients act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp. (*Ctenocephalides canis*, *Ctenocephalides felis*), *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis*, *Periplaneta americana*, *Blattella germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The inventive active ingredients of the formula (I) are also suitable for controlling arthropods which attack agricultural livestock, for example cattle, sheep, goats, horses, pigs, donkeys, camels, buffaloes, rabbits, chickens, turkeys, ducks, geese, honey-bees, other domestic animals such as, for example, dogs, cats, caged birds, aquarium fish, and experimental animals, for example hamsters, guinea pigs, rats and mice. The control of these arthropods is intended to reduce cases of death and reduced productivity (of meat, milk, wool, hides, eggs, honey etc.), and so more economic and easier animal husbandry is possible by use of the inventive active ingredients.

The inventive active ingredients are used in the veterinary sector and in animal husbandry in a known manner, by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active ingredient, such as collars, ear marks, tail marks, limb bands, halters, marking devices and the like.

When used for livestock, poultry, domestic animals and the like, the active ingredients of the formula (I) can be used as formulations (for example powders, emulsions, flowables) comprising the active ingredients in an amount of 1 to 80% by weight, either directly or after 100 to 10 000-fold dilution, or they may be used as a chemical bath.

It has also been found that the inventive compounds have strong insecticidal action against insects which destroy industrial materials.

Preferred but nonlimiting examples include the following insects:

beetles, such as *Hylotrupes bajulus*, *Chlorophorus pilosis*, *Anobium punctatum*, *Xestobium rufovillosum*, *Ptilinus pecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthes rugicollis*, *Xyleborus* spec. *Tryptodendron* spec., *Apate monachus*, *Bostrychus capucins*, *Heterobostrychus brunneus*, *Sinoxylon* spec. *Dinoderus minutus*;

dermapterans, such as *Sirex juvencus*, *Urocerus gigas*, *Urocerus gigas taignus*, *Urocerus augur*;

termites, such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis*, *Coptotermes formosanus*;

bristletails, such as *Lepisma saccarina*.

Industrial materials in the present connection are understood to mean inanimate materials, such as preferably plastics, adhesives, sizes, papers and cards, leather, wood, processed wood products and coating compositions.

The ready-to-use compositions may optionally also comprise other insecticides, and optionally one or more fungicides.

With respect to possible additional mixing partners, reference is made to the insecticides and fungicides mentioned above.

At the same time, the inventive compounds can be employed for protection of objects which come into contact with saltwater or brackish water, especially hulls, screens, nets, buildings, moorings and signalling systems, against fouling.

In addition, the inventive compounds can be used as antifouling compositions, alone or in combinations with other active ingredients.

The active ingredients are also suitable for controlling animal pests in the domestic sector, in the hygiene sector and in the protection of stored products, especially insects, arachnids and mites, which are found in enclosed spaces, for example homes, factory halls, offices, vehicle cabins and the like. They can be used to control these pests alone or in combination with other active ingredients and auxiliaries in domestic insecticide products. They are effective against sensitive and resistant species, and against all developmental stages. These pests include:

From the order of the Scorpionidea, for example, *Buthus occitanus*.

From the order of the Acarina, for example, *Argas persicus*, *Argas reflexus*, *Bryobia* spp., *Dermanyssus gallinae*, *Glyciphagus domesticus*, *Ornithodorus moubat*, *Rhipicephalus sanguineus*, *Trombicula alfreddugesi*, *Neutrombicula autumnalis*, *Dermatophagoides pteronissimus*, *Dermatophagoides forinae*.

From the order of the Araneae, for example, Avicularidae, Araneidae.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalis, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of domestic insecticides, they are used alone or in combination with other suitable active ingredients, such as phosphoric esters, carbamates, pyrethroids, neonicotinoids, growth regulators or active ingredients from other known classes of insecticides.

They are employed in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free or passive evaporation systems, moth papers, moth bags and moth gels, as granules or dusts, in baits for spreading or in bait stations.

PREPARATION EXAMPLES

Example A

N-{6-[1-(Pyridin-3-yl)-1H-pyrazol-4-yl]pyridin-2-yl}methanesulphonamide

Stage 1: 3-(4-Bromopyrazol-1-yl)pyridine

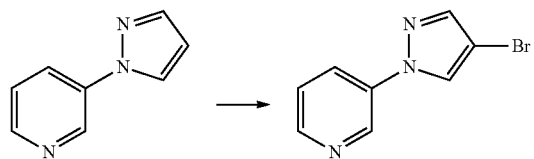 [SMILES: c1cncc(-n2cccn2)c1 ; Brc1cnn(-c2cccnc2)c1]

3-Pyrazol-1-ylpyridine (500 mg, 3.44 mmol) was dissolved in acetonitrile (15 ml), and ammonium cerium(IV) nitrate (944 mg, 1.72 mmol) was added (slightly exothermic). N-Bromosuccinimide (736 mg, 4.13 mmol) was added in portions (slightly exothermic) and the mixture was stirred at room temperature for 30 minutes (min) and then heated under reflux for 3 hours (h). After the mixture had cooled, ethyl acetate was added. The organic phase was washed with water, washed with a sodium sulphate solution and then dried over magnesium sulphate. The solvent was removed on a rotary evaporator under reduced pressure.

Yield: 750 mg (93% of theory), log P(HCOOH) 1.56, [M$^+$+1] 224.0

$^1$H NMR (d$_6$-DMSO): 7.54 (m, 1H), 7.90 (s, 1H), 8.20 (m, 1H), 8.55 (m, 1H), 8.79 (s, 1H), 9.06 (m, 1H).

Stage 2: 3-[4-(4,4,5,5-Tetramethyl-[1,3,2]dioxaborolan-2-yl)pyrazol-1-yl]pyridine

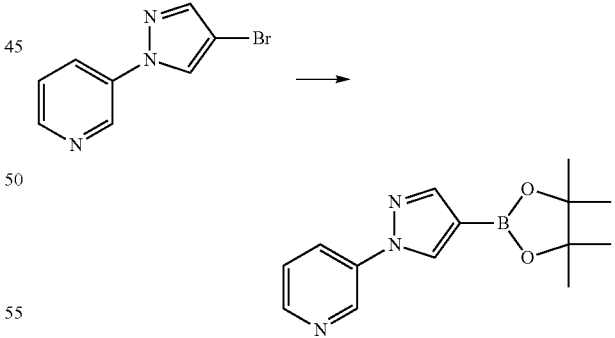

Under argon, 3-(4-bromopyrazol-1-yl)pyridine (1.00 g, 4.46 mmol), 1,1'-bis(diphenylphosphino)-ferrocene (dppf) (74 mg, 0.13 mmol), palladium dichloride-dppf (109 mg, 0.13 mmol), potassium acetate (1.31 g, 13.3 mmol) and pinacolatodiborane (1.19 g, 4.68 mmol) were added to dioxane (11 ml). The mixture was heated under reflux for 24 h and then cooled. The solvent was removed on a rotary evaporator under reduced pressure, dichloromethane (100 ml) and water (100 ml) were added to the residue, and the solids formed were filtered off with suction and discarded. The filtrate was extracted with dichloromethane and the organic phase was dried over magnesium sulphate. The solvent was removed on a rotary evaporator under reduced pressure and the residue was chromatographed (ethyl acetate, cyclohexane).

Yield: 680 mg (55% of theory), log P(HCOOH) 2.19, [M++1] 272.2

$^1$H NMR (d$_6$-DMSO): 1.30 (s, 12H), 7.51 (m, 1H), 7.90 (s, 1H), 8.25 (m, 1H), 8.51 (m, 1H), 8.73 (s, 1H), 9.12 (m, 1H).

Stage 3: 6-[1-(Pyridin-3-yl)-1H-pyrazol-4-yl]pyridine-2-amine

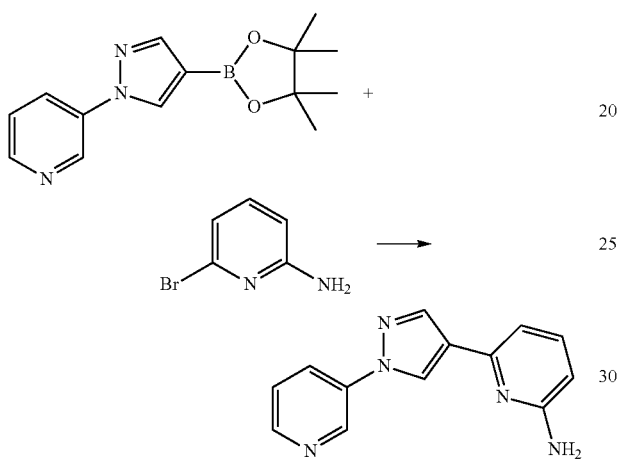

Under argon, 3.17 g (11.7 mmol) of 3-[4-(4,4,5,5-tetramethyl-1,3,2-dioxaborolan-2-yl)-1H-pyrazol-1-yl]pyridine, 2.02 g (11.7 mmol) of 6-bromopyridine-2-amine and 945 mg (817 µmol) of tetrakis(triphenylphosphine)palladium were added to a mixture, degassed by means of argon, of 23.3 ml of 2 M sodium carbonate solution in water and 63.3 ml of acetonitrile. The reaction mixture was heated to 75° C. for 18 hours, diluted with acetonitrile after cooling, dried over MgSO$_4$, filtered and concentrated. The crude product thus obtained was purified by chromatography (acetonitrile/acetone).

Yield 1.76 g (71% of theory)

HPLC-MS: log P(HCOOH): 0.30; mass (m/z): 238.1 (M+H)$^+$.

$^1$H NMR (d6-DMSO): 5.88 (s, 2H), 6.35 (d, 1H), 6.93 (d, 1H), 7.42 (t, 1H), 7.58 (dd, 1H), 8.22 (s, 1H), 8.28 (m, 1H), 8.54 (dd, 1H), 8.97 (s, 1H), 9.15 ppm (d, 1H).

Stage 4: N-{6-[1-(Pyridin-3-yl)-1H-pyrazol-4-yl]pyridin-2-yl}methanesulphonamide

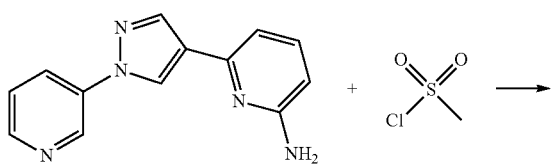

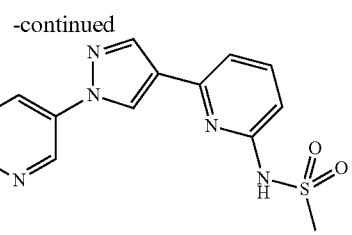

146 mg (585 µmol) of 6-[1-(pyridin-3-yl)-1H-pyrazol-4-yl]pyridine-2-amine and 54.0 µl (701 µmol) of N-methylmorpholine were initially charged in 10 ml of dichloromethane, and methanesulphonyl chloride was added at room temperature. The mixture was stirred overnight and the reaction mixture was filtered through silica gel (eluent: ethyl acetate). After concentration, the crude product was purified by chromatography (dichloromethane/methanol).

Yield: 50 mg (27% of theory); HPLC-MS: log P(HCOOH): 1.26; mass (m/z): 316.0 (M+H)$^+$;

$^1$H NMR (d6-DMSO): 6.82 (d, 1H), 7.45 (d, 1H), 7.59 (dd, 1H), 7.78 (t, 1H), 8.30 (m, 2H), 8.57 (dd, 1H), 9.09 (s, 1H), 9.17 (d, 1H), 10.55 ppm (s, 1H).

Example B

6-[2-(5-Fluoropyridin-3-yl)-1,3-thiazol-5-yl]-N-[(trifluoromethyl)sulphonyl]-pyridine-2-carboxamide Stage 1: 3-Fluoro-5-(1,3-thiazol-2-yl)pyridine

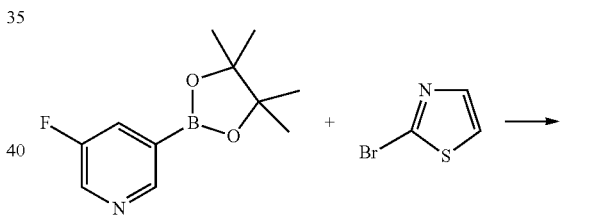

2.0 g (8.97 mmol) of the pyridyl boric ester, 1.47 g (8.97 mmol) of the 2-bromothiazole, 197 mg (0.27 mmol) of bis(diphenylphosphino)ferrocenepalladium(II) chloride and 3.72 g (26.9 mmol) of potassium carbonate were stirred under argon in 40 ml of dimethoxyethane at 80° C. for 16 h.

For workup, the mixture was concentrated and purified by means of column chromatography on silica gel (eluent: cyclohexane/ethyl acetate).

Yield: 778 mg (48% of theory)

HPLC-MS: log P(HCOOH): 1.48; mass (m/z): 180.9 (M+H)$^+$;

¹H NMR (d6-DMSO): 7.95 (m, 1H), 8.04 (m, 1H), 8.24 (m, 1H), 8.69 (m, 1H), 9.04 (m, 1H) ppm.

Stage 2: Methyl 6-[2-(5-fluoropyridin-3-yl)-1,3-thiazol-5-yl]pyridine-2-carboxylate

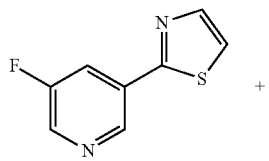
+
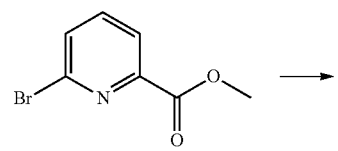
→
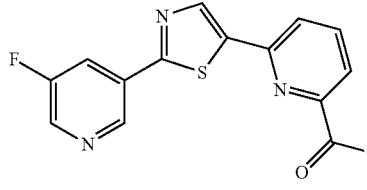

748 mg (4.15 mmol) of the fluoropyridylthiazole, 897 mg (4.15 mmol) of the bromopyridine, 62 mg (0.13 mmol) of dihydrogen dichloro bis(di-t-butylphosphinito-kP)palladate (2-) (dichloro{bis[di-tert-butyl(hydroxy)phosphoranyl]}palladium, POPd, from CombiPhos, USA) and 1.147 g (8.3 mmol) of potassium carbonate were stirred in 10 ml of dimethylformamide under argon at 120° C. for 16 h.

For workup, the mixture was concentrated and purified by means of column chromatography on silica gel (eluent: cyclohexane/ethyl acetate).

Yield: 615 mg (47% of theory)

HPLC-MS: log P(HCOOH): 2.37; mass (m/z): 316.0 (M+H)⁺;

¹H NMR (d6-DMSO): 3.93 (s, 3H), 8.03 (m, 1H), 8.14 (m, 1H), 8.36 (m, 2H), 8.73 (m, 1H), 8.80 (m, 1H), 9.12 (m, 1H) ppm.

Stage 3: 6-[2-(5-Fluoropyridin-3-yl)-1,3-thiazol-5-yl]pyridine-2-carboxylic acid

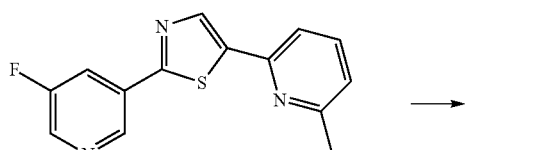

570 mg (1.81 mmol) of the methylpyridylcarboxylate were dissolved in a mixture of 25 ml of tetrahydrofuran and 8 ml of water, a solution of 152 mg (3.62 mmol) of lithium hydroxide monohydrate in 17 ml of water was added and the mixture was stirred at room temperature for 16 h.

For workup, the mixture was concentrated and partitioned between water and methyl t-butyl ether, the aqueous phase was acidified with 1N hydrochloric acid, and the precipitated solid was filtered off with suction and dried.

Yield: 556 mg (91% of theory)

HPLC-MS: log P(HCOOH): 1.72; mass (m/z): 302.1 (M+H)⁺;

¹H NMR (d6-DMSO): 8.00 (m, 1H), 8.10 (m, 1H), 8.32 (m, 2H), 8.72 (m, 1H), 8.78 (m, 1H), 9.10 (m, 1H), 13.5 (br) ppm.

Stage 4: 6-[2-(5-Fluoropyridin-3-yl)-1,3-thiazol-5-yl]-N-[(trifluoromethyl)sulphonyl]pyridine-2-carboxamide

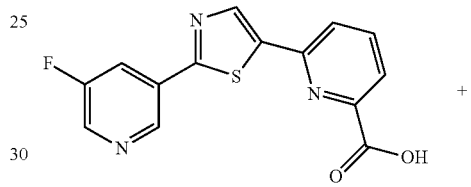
+
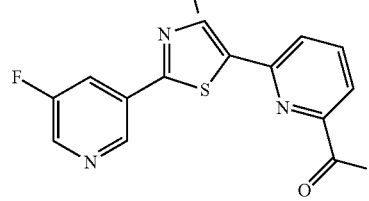
→
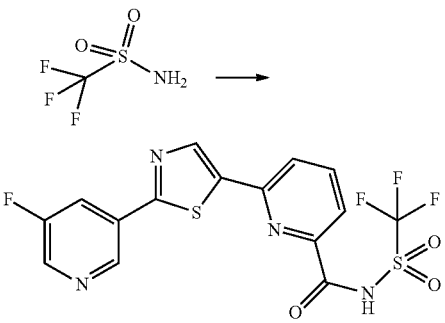

100 mg (0.33 mmol) of the pyridylcarboxylic acid were initially charged in 5 ml of tetrahydrofuran, 81 mg (0.50 mmol) of carbonyldiimidazole were added and the mixture was boiled at reflux for 1 h. After cooling to room temperature, 74 mg (0.50 mmol) of trifluoromethanesulphonamide were added, the mixture was stirred for 10 min, then 76 mg (0.50 mmol) of diazabicycloundecene (DBU) were added and the mixture was stirred at room temperature for 16 h.

For workup, the mixture was concentrated and purified by means of column chromatography on silica gel (eluent: dichloromethane/methanol).

Yield: 28 mg (20% of theory)

HPLC-MS: log P(HCOOH): 1.86; mass (m/z): 433.0 (M+H)⁺;

$^1$H NMR (d6-DMSO): 7.60 (m, 1H), 7.88 (m, 1H), 7.96 (m, 1H), 8.12 (m, 1H), 8.30 (m, 1H), 8.70 (m, 1H), 8.89 (m, 1H), 9.10 (m, 1H) ppm.

Example C

6-[5-(5-Fluoropyridin-3-yl)-1,3,4-thiadiazol-2-yl]-N-(methylsulphonyl)pyridine-2-carboxamide

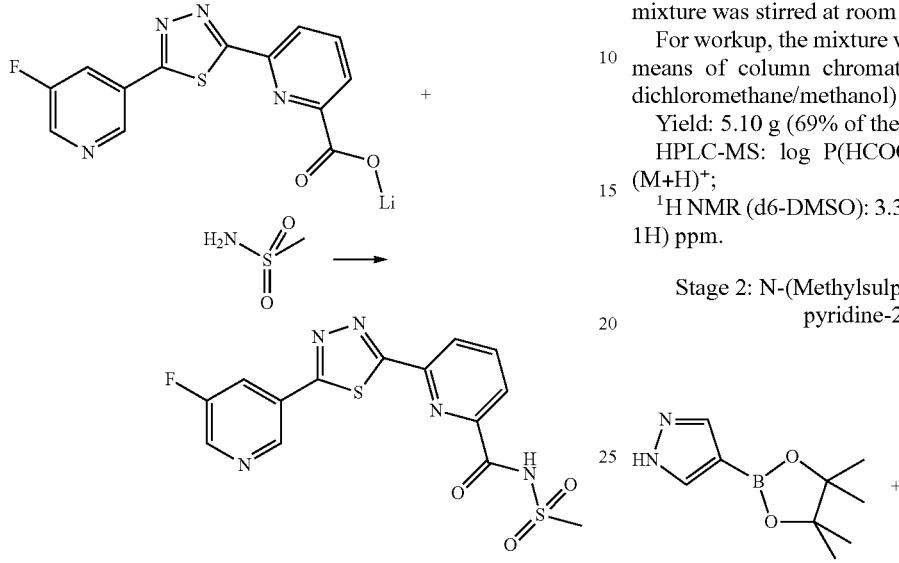

200 mg (0.64 mmol) of the lithium salt and 1.01 g (7.78 mmol) of diisopropylethylamine were initially charged in 5 ml of acetonitrile, 198 mg (0.77 mmol) of bis(2-oxo-3-oxazolidinyl)-phosphinyl chloride (BOP-Cl) were added, the mixture was stirred for 20 min, 185 mg (1.94 mmol) of methanesulphonamide and 99 mg (0.64 mmol) of diazabicycloundecene (DBU) were added and the mixture was stirred at room temperature for 16 h.

For workup, the mixture was concentrated and partitioned between water and ethyl acetate, and the organic phase was dried and concentrated. The further purification was effected by means of column chromatography on silica gel (eluent: dichloromethane/methanol) and then on RP18 silica gel (eluent: water/acetonitrile).

Yield: 37 mg (15% of theory)
HPLC-MS: log P(HCOOH): 1.79; mass (m/z): 380.1 (M+H)$^+$;
$^1$H NMR (d6-DMSO): 3.40 (s, 3H), 8.22 (m, 1H), 8.30 (m, 1H), 8.48 (m, 1H), 8.59 (m, 1H), 8.82 (m, 1H), 9.18 (m, 1H), 12.1 (br) ppm.

Example D

6-[1-(5-Fluoropyridin-3-yl)-1H-pyrazol-4-yl]-N-(methylsulphonyl)pyridine-2-carboxamide Stage 1:
6-Bromo-N-(methylsulphonyl)pyridine-2-carboxamide

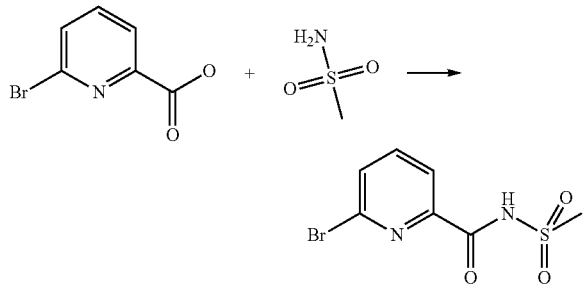

5.40 g (26.7 mmol) of 6-bromo-2-pyridinecarboxylic acid were initially charged in 150 ml of tetrahydrofuran, 6.51 g (40.0 mmol) of carbonyldiimidazole were added and the mixture was boiled at reflux for 1 h. After cooling to room temperature, 3.81 g (40.0 mmol) of methanesulphonamide were added, the mixture was stirred for 10 min, then 6.10 g (40 mmol) of diazabicycloundecene (DBU) were added and the mixture was stirred at room temperature for 16 h.

For workup, the mixture was concentrated and purified by means of column chromatography on silica gel (eluent: dichloromethane/methanol).

Yield: 5.10 g (69% of theory)
HPLC-MS: log P(HCOOH): 1.21; mass (m/z): 281.0 (M+H)$^+$;
$^1$H NMR (d6-DMSO): 3.37 (s, 3H), 7.95 (m, 2H), 8.06 (m, 1H) ppm.

Stage 2: N-(Methylsulphonyl)-6-(1H-pyrazol-4-yl)pyridine-2-carboxamide

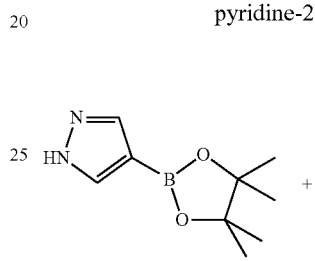

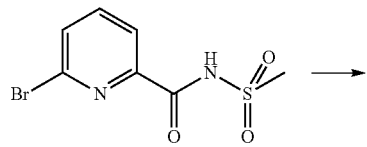

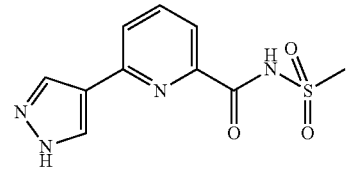

285 mg (1.47 mmol) of the 4-pyrazoleboronic ester, 410 mg (1.47 mmol) of the bromopyridine, 32 mg (0.04 mmol) of bis(diphenylphosphino)ferrocenepalladium(II) chloride and 467 mg (4.41 mmol) of potassium carbonate were stirred in 10 ml of dimethoxyethane under argon at 80° C. for 16 h.

For workup, the mixture was concentrated and purified by means of column chromatography on silica gel (eluent: cyclohexane/ethyl acetate).

Yield: 145 mg (37% of theory)
HPLC-MS: log P(HCOOH): 0.91; mass (m/z): 267.0 (M+H)$^+$ Stage 3: 6-[1-(5-Fluoropyridin-3-yl)-1H-pyrazol-4-yl]-N-(methylsulphonyl)pyridine-2-carboxamide

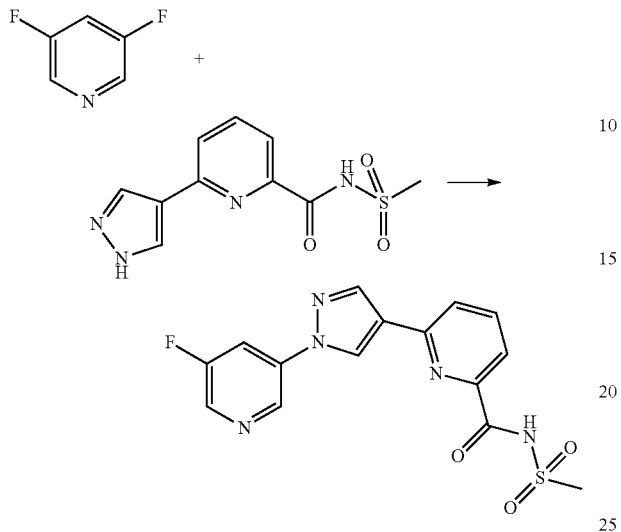

43 mg (0.37 mmol) of 3,5-difluoropyridine, 99 mg (0.37 mg) of the pyrazolylpyridine, 6 mg (0.01 mmol) of dihydrogen dichloro bis(di-t-butylphosphinito-kP)palladate(2-) (POPd, from CombiPhos, USA) and 102 mg (0.74 mmol) of potassium carbonate were stirred in 5 ml of dimethylformamide under argon at 120° C. for 12 h.

For workup, the mixture was concentrated and purified by means of column chromatography on silica gel (eluent: dichloromethane/methanol).

Yield: 35 mg (26% of theory)

HPLC-MS: log P(HCOOH): 1.98; mass (m/z): 362.1 (M+H)$^+$;

$^1$H NMR (d6-DMSO): 3.40 (s, 3H), 7.98 (m, 1H), 8.08 (m, 2H), 8.2 (m, 1H), 8.58 (m, 1H), 8.70 (m, 1H), 9.08 (m, 1H), 9.40 (m, 1H) ppm.

Example E

N-[({6-[2-(Pyridin-3-yl)-1,3-thiazol-5-yl]pyridin-2-yl}sulphonyl)acetamide

Stage 1:
N-[(6-Bromopyridin-2-yl)sulphonyl]acetamide

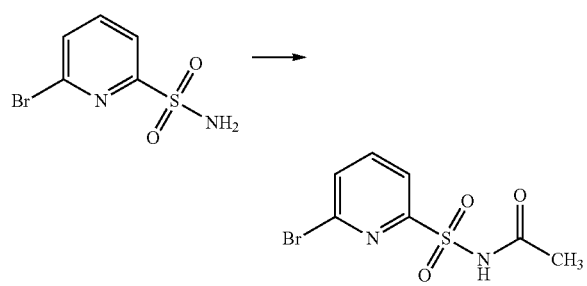

6-Bromopyridine-2-sulphonamide (0.5 g, 2.11 mmol, prepared by the methods described in WO2005/058299) and potassium carbonate (2.92 g, 21.1 mmol) were initially charged in acetonitrile (10 ml). While cooling with ice, acetyl chloride (1.16 g, 14.8 mmol) was added dropwise and the reaction mixture was stirred at room temperature for 16 h. The solvent was removed under reduced pressure, and the residue was taken up in water and acidified with dilute hydrochloric acid solution. It was extracted with ethyl acetate and the solvent was removed under reduced pressure. This gave 0.54 g (85% of theory) of N-[(6-bromopyridin-2-yl)sulphonyl]-acetamide.

HPLC-MS: log P(HCOOH): 0.95; mass (m/z): 278.9 (M+H)$^+$;

$^1$H NMR (d6-DMSO): 1.99 (s, 3H), 7.99-8.01 (m, 1H), 8.08 (t, 1H), 8.11-8.13 (m, 1H), 12.48 (s, 1H) ppm.

Stage 2: N-({6-[2-(Pyridin-3-yl)-1,3-thiazol-5-yl]pyridin-2-yl}sulphonyl)acetamide

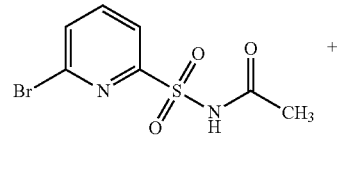

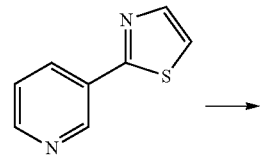

N-[(6-Bromopyridin-2-yl)sulphonyl]acetamide (0.112 g, 0.4 mmol), 3-(1,3-thiazol-2-yl)pyridine (0.065 g, 0.4 mmol, prepared by the methods described in WO 2010/006713), dichloro{bis[di-tert-butyl(hydroxy)phosphoranyl]}palladium (0.006 g, 0.012 mmol) and caesium carbonate (0.26 g, 0.8 mmol) were stirred in 10 ml of N,N-dimethylformamide at 120° C. under argon for 16 h. After cooling, the solvent was removed under reduced pressure and the residue was chromatographed (silica gel, dichloromethane/methanol eluent). This gave 0.024 g (15% of theory) of N-({6-[2-(pyridin-3-yl)-1,3-thiazol-5-yl]pyridin-2-yl}sulphonyl)acetamide.

HPLC-MS: log P(HCOOH): 1.30; mass (m/z): 361.0 (M+H)$^+$;

¹H NMR (d6-DMSO): 2.03 (s, 3H), 7.61 (m, 1H), 8.02 (m, 1H), 8.13 (m, 1H), 8.30 (m, 1H), 8.41 (m, 1H), 8.71 (m, 1H), 8.91 (m, 1H), 9.20 (m, 1H) ppm.

Example F

N-({6-[1-(Pyridin-3-yl)-1H-pyrazol-4-yl]pyridin-2-yl}sulphomnyl)acetamide

Stage 1: 6-[1-(Pyridin-3-yl)-1H-pyrazol-4-yl]pyridine-2-sulphonamide

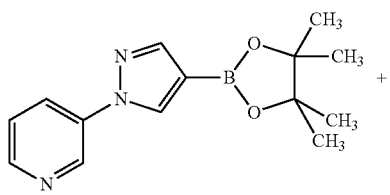

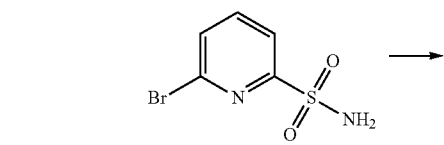

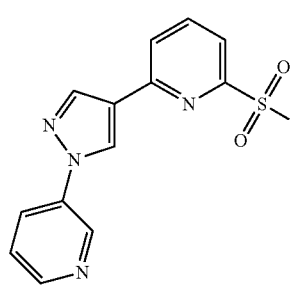

Under argon, 3-[4-(4,4,5,5-tetramethyl-1,3,2-dioxaborolan-2-yl)-1H-pyrazol-1-yl]pyridine (0.2 g, 0.74 mmol, prepared by the methods described in WO 2011/045224), 6-bromopyridin-2-sulphonamide (0.175 g, 0.74 mmol) and tetrakis(triphenylphosphine)palladium (0.025 g, 0.022 mmol) were added to a mixture, degassed by means of argon, of sodium carbonate solution in water (2.9 ml, 2 M/L) and acetonitrile (4 ml). The reaction mixture was stirred at 70° C. for 18 h. After cooling, the reaction mixture was poured onto water and the precipitated crystals were filtered off with suction. They were subsequently stirred with diethyl ether and filtered off with suction. This gave 0.23 g (97% of theory) of 6-[1-(pyridin-3-yl)-1H-pyrazol-4-yl]pyridine-2-sulphonamide.

HPLC-MS: log P(HCOOH): 0.99; mass (m/z): 302.1 (M+H)⁺

¹H NMR (d6-DMSO): 7.43 (s, 2H), 7.60-7.63 (m, 1H), 7.76 (d, 1H), 8.00 (d, 1H), 8.11 (t, 1H), 8.28-8.31 (m, 1H), 8.53 (s, 1H), 8.58-8.60 (m, 1H), 9.16-9.17 (m, 1H), 9.33 (s, 1H) ppm Stage 2: N-({6-[1-(Pyridin-3-yl)-1H-pyrazol-4-yl]pyridin-2-yl}sulphonyl)acetamide

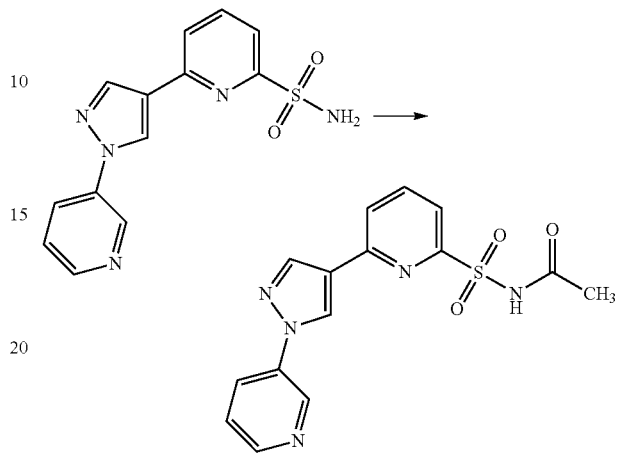

6-[1-(Pyridin-3-yl)-1H-pyrazol-4-yl]pyridin-2-sulphonamide (0.15 g, 0.44 mmol) was initially charged in acetonitrile (1.5 ml) under argon, and sodium hydride (0.026 g, 0.66 mmol, 60%) was added in portions. The reaction mixture was stirred at room temperature for 1 h, then acetyl chloride (0.052 g, 0.66 mmol) was added dropwise. The reaction mixture was stirred at 82° C. for 33 h and, after cooling, the solvent was removed under reduced pressure. The residue was taken up in saturated sodium hydrogencarbonate solution, dichloromethane was added and the precipitated solid was filtered off. The phases of the filtrate were separated; the aqueous phase was adjusted to pH 3 with hydrochloric acid and left to stand for 16 h. The precipitated crystals were filtered off with suction. Yield 0.02 g (12% of theory) of N-({6-[1-(pyridin-3-yl)-1H-pyrazol-4-yl]pyridin-2-yl}sulphonyl)acetamide.

HPLC-MS: log P(HCOOH): 1.17; mass (m/z): 344.1 (M+H)⁺

¹H NMR (d6-DMSO): 2.03 (s, 3H), 7.60-7.64 (m, 1H), 7.92-7.94 (m, 1H), 8.08-8.10 (m, 1H), 8.17-8.20 (m, 1H), 8.29-8.31 (m, 1H), 8.37 (s, 1H), 8.59-8.60 (m, 1H), 9.16-9.17 (m, 1H), 9.26 (s, 1H), 12.31 (s, 1H) ppm Example G N-(Methylsulphonyl)-2-[1-(pyridin-3-yl)-1H-pyrazol-4-yl]-1,3-thiazole-4-carboxamide Stage 1: 2-Bromo-N-(methylsulphonyl)-1,3-thiazole-4-carboxamide

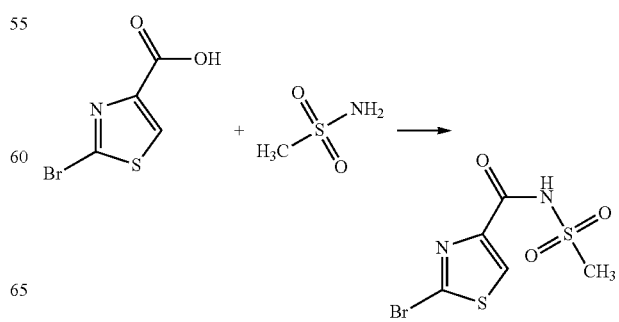

2-Bromo-1,3-thiazole-4-carboxylic acid (0.8 g, 3.85 mmol) was initially charged in tetrahydrofuran (10 ml). N,N'-Carbonyldiimidazole (0.94 g, 5.77 mmol) was added and the reaction mixture was heated under reflux for 1 h. Methanesulphonamide (0.55 g, 5.77 mmol) was added and, after 10 min, 1,8-diazabicyclo[5.4.0]undec-7-ene (0.88 g, 5.77 mmol). The reaction mixture was stirred at room temperature for 16 h and then the solvent was removed under reduced pressure. The residue was taken up in water and acidified with hydrochloric acid. The precipitated product was filtered off with suction. The aqueous phase was extracted with dichloromethane; the organic phase was dried over sodium sulphate and filtered, and the solvent was removed under reduced pressure. This gave a total of 1.0 g (89% of theory) of 2-bromo-N-(methylsulphonyl)-1,3-thiazole-4-carboxamide.

HPLC-MS: log P(HCOOH): 0.83; mass (m/z): 284.9 (M+H)$^+$;

$^1$H NMR (d6-DMSO): 3.33 (s, 3H), 8.61 (s, 1H), 12.00 (s, 1H)

Stage 2: N-(Methylsulphonyl)-2-[1-(pyridin-3-yl)-1H-pyrazol-4-yl]-1,3-thiazole-4-carboxamide

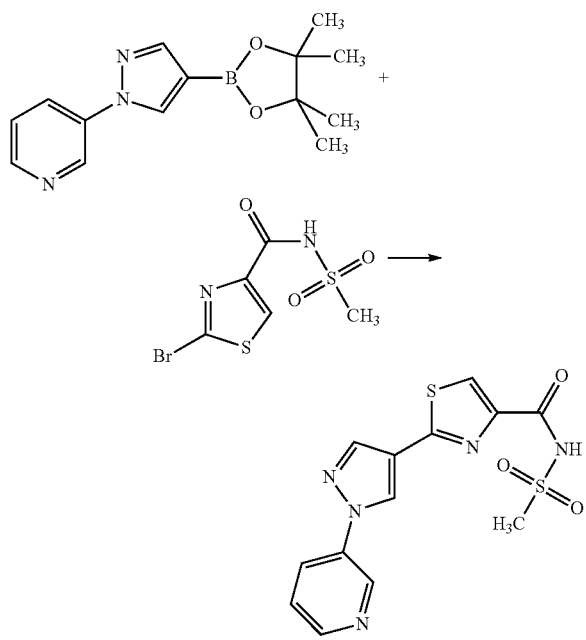

Under argon, 3-[4-(4,4,5,5-tetramethyl-1,3,2-dioxaborolan-2-yl)-1H-pyrazol-1-yl]pyridine (0.1 g, 0.37 mmol), 2-bromo-N-(methylsulphonyl)-1,3-thiazole-4-carboxamide (0.105 g, 0.37 mmol) and tetrakis(triphenylphosphine)palladium (0.013 g, 0.011 mmol) were added to a mixture, degassed by means of argon, of sodium carbonate solution in water (1.5 ml, 2 M/L) and acetonitrile (3.8 ml). The reaction mixture was stirred at 70° C. for 16 h. After cooling, the reaction mixture was poured onto water and extracted with dichloromethane. The organic phase was dried over sodium sulphate and the solvent was removed under reduced pressure. The residue was subsequently stirred with diethyl ether and filtered off with suction. This gave 0.23 g (97% of theory) of 6-[1-(pyridin-3-yl)-1H-pyrazol-4-yl]pyridine-2-sulphonamide.

HPLC-MS: log P(HCOOH): 1.25; mass (m/z): 350.1 (M+H)$^+$ $^1$H NMR (d6-DMSO): 3.38 (s, 3H), 7.48-7.49 (m, 1H), 8.32-8.35 (m, 1H), 8.45 (s, 1H), 8.56 (s, 1H), 8.59-8.60 (m, 1H), 9.19-9.20 (m, 1H), 9.34 (s, 1H) ppm Example H 4-[1-(5-Fluoropyridin-3-yl)-1H-pyrazol-4-yl]-N-(methylsulphonyl)-1,3-thiazole-2-carboxamide Stage 1: 4-Bromo-N-(methylsulphonyl)-1,3-thiazole-2-carboxamide

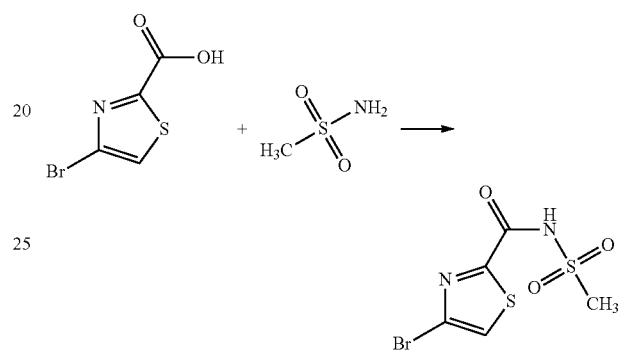

4-Bromo-1,3-thiazole-2-carboxylic acid (1.0 g, 4.8 mmol) were initially charged in tetrahydrofuran (10 ml). N,N'-Carbonyldiimidazole (1.17 g, 7.2 mmol) was added and the reaction mixture was heated under reflux for 1 h. Methanesulphonamide (0.69 g, 7.2 mmol) was added and, after 10 min, 1,8-diazabicyclo[5.4.0]undec-7-ene (1.10 g, 7.2 mmol). The reaction mixture was stirred at room temperature for 16 h and then the solvent was removed under reduced pressure. The residue was taken up in water and acidified with hydrochloric acid. The precipitated product was filtered off with suction. This gave 1.18 g (84% of theory) of 4-bromo-N-(methylsulphonyl)-1,3-thiazole-2-carboxamide.

HPLC-MS: log P(HCOOH): 0.63; mass (m/z): 284.9 (M+H)$^+$;

$^1$H NMR (d6-DMSO): 3.31 (s, 3H), 8.31 (s, 1H)

Stage 2: 4-[1-(5-Fluoropyridin-3-yl)-1H-pyrazol-4-yl]-N-(methylsulphonyl)-1,3-thiazole-2-carboxamide

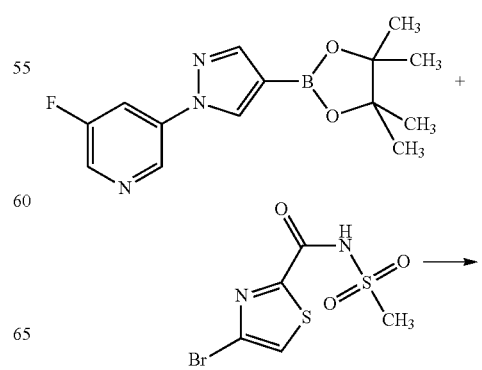

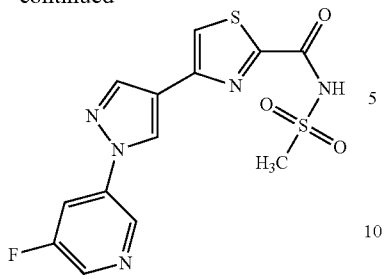

Under argon, 3-fluoro-5-[4-(4,4,5,5-tetramethyl-1,3,2-dioxaborolan-2-yl)-1H-pyrazol-1-yl]pyridine (0.2 g, 0.69 mmol, prepared by the methods described in WO 2011/045224), 2-bromo-N-(methylsulphonyl)-1,3-thiazole-4-carboxamide (0.2 g, 0.69 mmol) and tetrakis-(triphenylphosphine)palladium (0.024 g, 0.021 mmol) were added to a mixture, degassed by means of argon, of sodium carbonate solution in water (2.8 ml, 2 M/L) and acetonitrile (9.4 ml). The reaction mixture was stirred at 70° C. for 16 h. After cooling, the reaction mixture was poured onto water and extracted with dichloromethane. The aqueous phase was acidified with hydrochloric acid and the precipitated solid was filtered off with suction. The crude product was chromatographed with ethyl acetate/2-propanol on silica gel. This gave 0.21 g (8% of theory) of 4-[1-(5-fluoropyridin-3-yl)-1H-pyrazol-4-yl]-N-(methylsulphonyl)-1,3-thiazole-2-carboxamide.

HPLC-MS: log P(HCOOH): 1.68; mass (m/z): 368.1 (M+H)+

¹H NMR (d6-DMSO): 2.99 (s, 3H), 7.96 (s, 1H), 8.33 (s, 1H), 8.34 (s, 1H), 8.55-8.57 (m, 1H), 9.10 (s, 1H), 9.12 (s, 1H) ppm Example I 3-[2-(5-Fluoropyridin-3-yl)-4-methyl-1,3-thiazol-5-yl]-1-methyl-N-(methylsulphonyl)-1H-pyrazole-5-carboxamide Stage 1: Ethyl 4-[2-(5-fluoropyridin-3-yl)-4-methyl-1,3-thiazol-5-yl]-2,4-dioxobutanoate

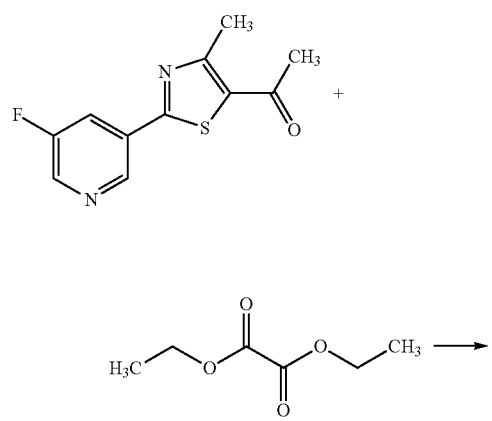

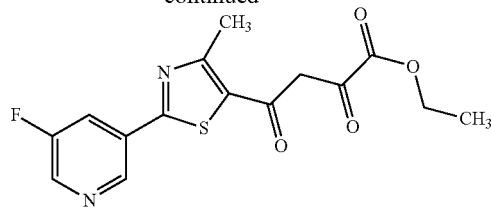

Under argon, lithium bis(trimethylsilyl)amide (21 ml, 1 M/L in tetrahydrofuran) was initially charged in tetrahydrofuran (150 ml). At −78° C., 1-[2-(5-fluoropyridin-3-yl)-4-methyl-1,3-thiazol-5-yl]ethanone (5.0 g, 21 mmol, prepared analogously to Biorg. & Med. Chem. Lett 1056 (2007) and 2828 (2010)) dissolved in diethyl ether was slowly added dropwise and the reaction mixture was stirred for 2 h. Diethyl oxalate (3.1 g, 21 mmol) dissolved in ether was added dropwise and the reaction mixture was stirred at room temperature for 16 h. Subsequently, potassium hydrogensulphate solution (5%) was added and the mixture was extracted repeatedly with ethyl acetate. The combined organic phases were dried and the solvent was removed under reduced pressure. This gave 7.1 g (99% of theory) of ethyl 4-[2-(5-fluoropyridin-3-yl)-4-methyl-1,3-thiazol-5-yl]-2,4-dioxobutanoate.

HPLC-MS: log P(HCOOH): 3.37; mass (m/z): 337.1 (M+H)+

¹H NMR (d6-DMSO): 1.31 (t, 3H), 2.79 (s, 3H), 4.31-4.32 (m, 2H), 6.71 (bs, 2H), 8.33 (d, 1H), 8.77 (s, 1H), 9.10 (s, 1H) ppm Stage 2: Ethyl 3-[2-(5-fluoropyridin-3-yl)-4-methyl-1,3-thiazol-5-yl]-1-methyl-1H-pyrazole-5-carboxylate

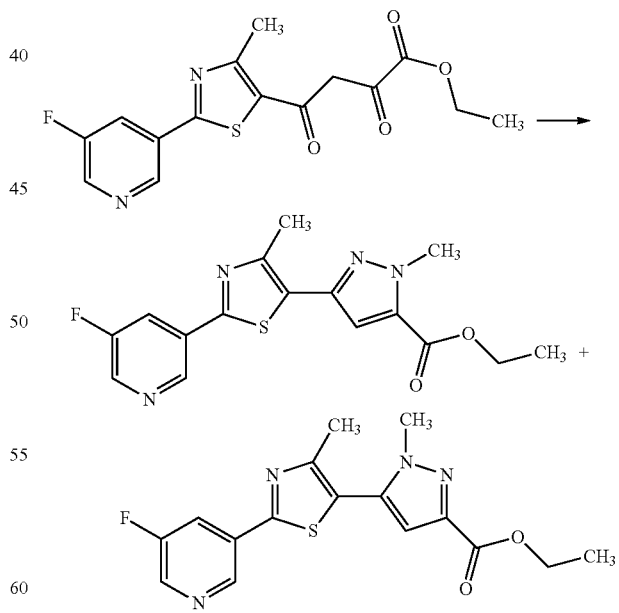

Ethyl 4-[2-(5-fluoropyridin-3-yl)-4-methyl-1,3-thiazol-5-yl]-2,4-dioxobutanoate (6.9 g, 20.5 mmol) and methylhydrazine (0.65 g, 20.5 mmol) were heated in ethanol (250 ml) under reflux for 2 h. The product formed was filtered off with suction and the solvent of the filtrate was removed under reduced pressure. The residue was chromatographed on silica gel (cyclohexane/ethyl acetate eluent). This gave a total of 1.24 g (17% of theory) of ethyl 3-[2-(5-fluoropyridin-3-yl)-4-methyl-1,3-thiazol-5-yl]-1-methyl-1H-pyrazole-5-carboxylate. As a by-product, 4.8 g (67% of theory) of ethyl 5-[2-(5-fluoropyridin-3-yl)-4-methyl-1,3-thiazol-5-yl]-1-methyl-1H-pyrazole-3-carboxylate were obtained.

HPLC-MS: log P(HCOOH): 3.70; mass (m/z): 347.0 (M+H)$^+$ $^1$H NMR (d6-DMSO): 1.35 (t, 3H), 2.63 (s, 3H), 4.15 (s, 3H), 4.35 (q, 2H), 7.17 (s, 1H), 8.19-8.22 (m, 1H), 8.68-8.69 (m, 1H), 9.00-9.01 (m, 1H) ppm Stage 3: 3-[2-(5-Fluoropyridin-3-yl)-4-methyl-1,3-thiazol-5-yl]-1-methyl-1H-pyrazole-5-carboxylic acid

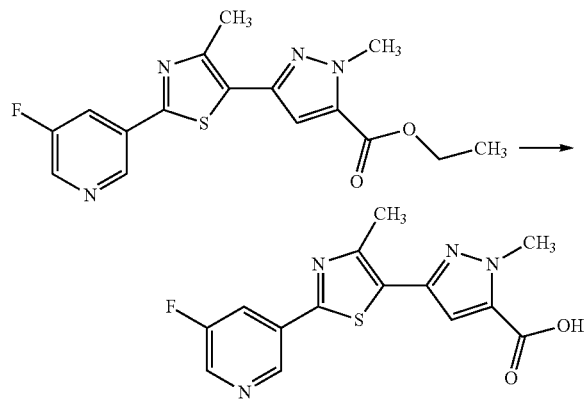

Ethyl 3-[2-(5-fluoropyridin-3-yl)-4-methy 1-1,3-thiazol-5-yl]-1-methyl-1H-pyrazole-5-carboxylate (1.1 g, 3.1 mmol) was dissolved in tetrahydrofuran (200 ml) and water (100 ml), and lithium hydroxide monohydrate (0.26 g, 6.2 mmol) dissolved in water (100 ml) was added. The reaction mixture was stirred at room temperature for 16 h, then neutralized with hydrochloric acid, and the solvent was removed under reduced pressure. The precipitated solid was filtered off with suction. This gave 0.96 g (94% of theory) of 3-[2-(5-fluoropyridin-3-yl)-4-methyl-1,3-thiazol-5-yl]-1-methyl-1H-pyrazole-5-carboxylic acid.

HPLC-MS: log P(HCOOH): 2.05; mass (m/z): 319.0 (M+H)$^+$ $^1$H NMR (d6-DMSO): 2.62 (s, 3H), 4.14 (s, 3H), 7.13 (s, 1H), 8.18-8.22 (m, 1H), 8.68-8.69 (m, 1H), 9.00-9.01 (m, 1H) ppm Stage 4: 3-[2-(5-Fluoropyridin-3-yl)-4-methyl-1,3-thiazol-5-yl]-1-methyl-N-(methyl sulphonyl)-1H-pyrazole-5-carboxamide

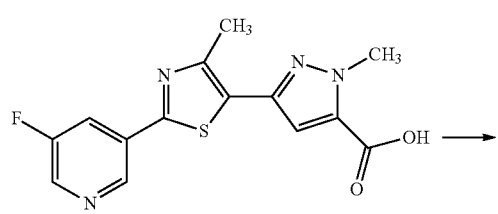

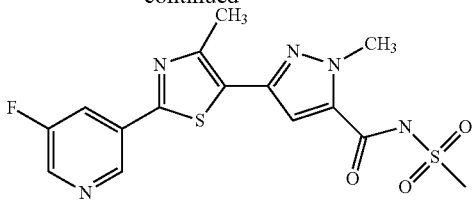

3-[2-(5-Fluoropyridin-3-yl)-4-methyl-1,3-thiazol-5-yl]-1-methyl-1H-pyrazole-5-carboxylic acid (0.08 g, 0.25 mmol) and methanesulphonamide (0.024 g, 0.25 mmol) were initially charged in ice-cooled dichloromethane (10 ml). 4-Dimethylaminopyridine (0.006 g, 0.05 mmol) and N-(3-dimethylaminopropyl)-N'-ethylcarbodiimide hydrochloride (0.053 g, 0.275 mmol) were added. The reaction mixture was stirred at 0° C. for 2 h and then at room temperature for 16 h. The solvent was removed under reduced pressure and the residue was chromatographed on silica gel (dichloromethane/ethyl acetate eluent). This gave 0.074 g (72% of theory) of 3-[2-(5-fluoropyridin-3-yl)-4-methyl-1,3-thiazol-5-yl]-1-methyl-N-(methylsulphonyl)-1H-pyrazole-5-carboxamide.

HPLC-MS: log P(HCOOH): 2.04; mass (m/z): 396.0 (M+H)$^+$ $^1$H NMR (d6-DMSO): 2.55 (s, 3H), 3.40 (s, 3H), 4.12 (s, 3H), 7.68 (m, 1H), 8.12 (m, 1H), 8.69 (m, 1H), 9.01 (m, 1H) ppm Example J Methyl 6-[2-(5-fluoropyridin-3-yl)-1,3-thiazol-5-yl]pyridine-2-carboximidoate Stage 1: 6-[2-(5-Fluoropyridin-3-yl)-1,3-thiazol-5-yl]pyridine-2-carbonitrile

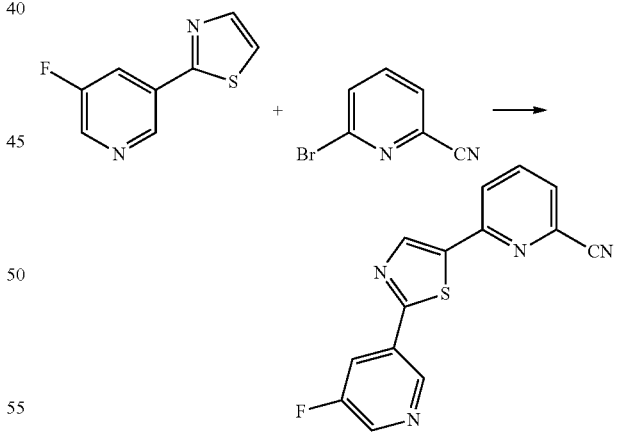

Under argon, 3-fluoro-5-(1,3-thiazol-2-yl)pyridine (0.99 g, 5.47 mmol) and 6-bromopyridin-2-carbonitrile (1.0 g, 5.47 mmol) were initially charged in DMF (15 ml). After 10 min, at room temperature, tris(2-methylphenyl)phosphine (0.13 g, 0.23 mmol) and palladium(II) chloride (0.1 g, 0.55 mmol) were added. The reaction mixture was stirred at 130° C. for 14 h. After cooling, water and ethyl acetate were added and the precipitated product was filtered off with suction. The organic phase of the filtrate was removed and the aqueous phase was extracted three times with ethyl acetate. The combined organic phases were dried over magnesium sulphate and the solvent was removed under reduced pressure. The residue was stirred with dichloromethane and filtered off with suction. This gave a total of 0.94 g (61% of theory) of 6-[2-(5-fluoropyridin-3-yl)-1,3-thiazol-5-yl]pyridine-2-carbonitrile.

HPLC-MS: log P(HCOOH): 2.51; mass (m/z): 283 (M+H)$^+$ $^1$H NMR (d6-DMSO): 8.02 (d, 1H), 8.20 (t, 1H), 8.32-8.46 (m, 1H), 8.44 (d, 1H), 8.75 (d, 1H), 8.84 (s, 1H), 9.12 (s, 1H) ppm Stage 2: Methyl 6-[2-(5-fluoropyridin-3-yl)-1,3-thiazol-5-yl]pyridine-2-carboximidoate

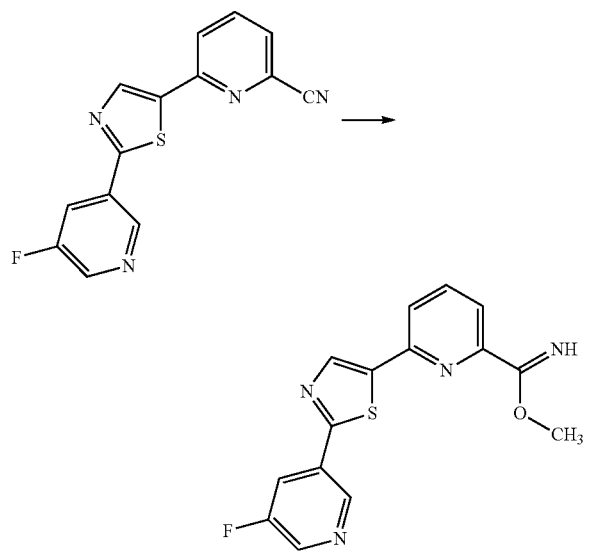

6-[2-(5-Fluoropyridin-3-yl)-1,3-thiazol-5-yl]pyridine-2-carbonitrile (0.33 g, 1.17 mmol) and sodium methoxide (0.13 g, 0.23 mmol) were stirred in methanol (10 ml) and dichloromethane (10 ml) at room temperature for 3 d. The precipitated solid was filtered off and the solvent of the filtrate was removed under reduced pressure. The residue was dissolved in dichloromethane and filtered through Celite. The solvent of the filtrate was removed under reduced pressure. This gave 0.32 g (83% of theory) of methyl 6-[2-(5-fluoropyridin-3-yl)-1,3-thiazol-5-yl]pyridine-2-carboximidoate.

HPLC-MS: log P(HCOOH): 0.90; mass (m/z): 315 (M+H)$^+$ $^1$H NMR (d6-DMSO): 4.05 (s, 3H), 7.79-7.81 (m, 2H), 7.87-7.91 (m, 1H), 8.05-8.07 (m, 1H), 8.38 (s, 1H), 8.56 (s, 1H), 9.06 (s, 1H), 9.24 (s, 11-1) ppm Example K 6-[2-(5-Fluoropyridin-3-yl)-1,3-thiazol-5-yl]pyridine-2-carboximide amide hydrochloride (1:1)

Methyl 6-[2-(5-fluoropyridin-3-yl)-1,3-thiazol-5-yl]pyridine-2-carboximidoate (0.1 g, 0.32 mmol) and ammonium chloride (0.016 g, 0.3 mmol) were stirred in methanol (3 ml) and dichloromethane (2 ml) at room temperature for 2 days. The solvent was removed under reduced pressure, and the residue was taken up in methanol and filtered through Celite. The solvent of the filtrate was removed under reduced pressure, and the residue was stirred with t-butyl methyl ether and filtered off with suction. This gave 0.07 g (65% of theory) of 6-[2-(5-fluoropyridin-3-yl)-1,3-thiazol-5-yl]pyridine-2-carboximide amide hydrochloride (1:1).

HPLC-MS: log P(HCOOH): 0.71; mass (m/z): 300 (M+H)$^+$ $^1$H NMR (d6-DMSO): 8.19-8.22 (m, 1H), 8.26-8.31 (m, 2H), 8.39-8.41 (m, 1H), 8.74-8.75 (m, 1H), 8.93 (s, 1H), 9.07-9.08 (m, 1H) ppm The following compounds of the formula (I) were obtained analogously to or according to the preparation processes described above:

| Number | Compound | logP (HCOOH) | NMR data | Mass M$^+$ + 1 |
|---|---|---|---|---|
| 1 (PE A) | | 1.26 | 1H NMR (d6-DMSO): 6.82 (d, 1H), 7.45 (d, 1H), 7.59 (dd, 1H), 7.78 (t, 1H), 8.30 (m, 2H), 8.57 (dd, 1H), 9.09 (s, 1H), 9.17 (d, 1H), 10.55 ppm (s, 1H). | 316.0 |

-continued

| Number | Compound | logP (HCOOH) | NMR data | Mass M+ + 1 |
|---|---|---|---|---|
| 2 (PE B) | | 1.86 | 1H NMR (d6-DMSO): 7.60 (m, 1H), 7.88 (m, 1H), 7.96 (m, 1H), 8.12 (m, 1H), 8.30 (m, 1H), 8.70 (m, 1H), 8.89 (m, 1H), 9.10 (m, 1H) ppm. | 433 |
| 3 (PE C) | | 1.79 | 1H NMR (d6-DMSO): 3.40 (s, 3H), 8.22 (m, 1H), 8.30 (m, 1H), 8.48 (m, 1H), 8.59 (m, 1H), 8.82 (m, 1H), 9.18 (m, 1H), 12.1 (br) ppm. | 380.1 |
| 4 (PE D) | | 1.98 | 1H NMR (d6-DMSO): 3.40 (s, 3H), 7.98 (m, 1H), 8.08 (m, 2H), 8.2 (m, 1H), 8.58 (m, 1H), 8.70 (m, 1H), 9.08 (m, 1H), 9.40 (m, 1H) ppm. | 362.1 |
| 5 | | 1.86 | 1H NMR (d6-DMSO): 2.66 (s, 6H), 7.78-7.85 (m, 3H), 8.50 (s, 1H), 9.17 (s, 1H), 9.26 (s, 1H), 9.40 (s, 2H) | 373 |
| 6 | | 2.44 | 1H NMR (d6-DMSO): 1.18 (m, 4H), 3.15 (m, 1H), 8.04 (m, 1H), 8.15 (m, 1H), 8.33 (m, 2H), 8.74 (s, 1H), 8.91 (s, 1H), 9.11 (s, 1H), 11.8 (br) ppm. | 404.9 |
| 7 | | 1.63 | 1H NMR (d6-DMSO): 1.31 (t, 3H), 3.58 (q, 2H), 7.96-7.98 (m, 1H), 8.07-8.14 (m, 2H), 8.83 (s, 1H), 9.20 (s, 1H), 9.38 (s, 2H), 9.52 (s, 1H), 11.60 (s, 1H) | 358 |

| Number | Compound | logP (HCOOH) | NMR data | Mass M⁺ + 1 |
|---|---|---|---|---|
| 8 | | 1.48 | 1H NMR (d6-DMSO): 3.40 (s, 3H), 8.02 (m, 1H), 8.18 (m, 1H), 8.35 (m, 1H), 8, 95 (s, 1H), 9, 30 (s, 1H), 9, 40 (s, 2H), 11.8 (br) ppm. | 362 |
| 9 | | 2.05 | 1H NMR (d6-DMSO): 3.42 (s, 3H), 8.02 (m, 1H), 8.19 (m, 1H), 8.34 (m, 2H), 8.75 (m, 1H), 8.93 (m, 1H), 9.11 (m, 1H), 11.8 (br) ppm. | 379 |
| 10 | | 1.43 | 1H NMR (d6-DMSO): 3.21 (s, 3H), 3.78 (t, 2H), 3.92 (m, 2H), 6.79 (d, 1H), 7.45 (d, 1H), 7.60 (dd, 1H), 7.78 (t, 1H), 8.29 (m, 2H), 8.58 (dd, 1H), 9.10 (s, 1H), 9.16 (d, 1H), 10.67 ppm (br. s, 1H). | 360.2 |
| 11 | | 1.79 | 1H NMR (d6-DMSO): 6.75 (m, 1H), 7.50 (m, 1H), 7.93 (m, 2H), 8.12 (m, 1H), 8.32 (m, 1H), 8.70 (m, 2H), 9.10 (m, 1H) ppm. | 415 |
| 12 | | 1.56 | 1H NMR (d6-DMSO): 3.42 (s, 3H), 7.78 (m, 1H), 8.00 (m, 1H), 8.18 (m, 1H), 8.32 (m, 1H), 8.50 (m, 1H), 8.75 (m, 1H), 8.90 (s, 1H), 9.29 (m, 1H), 11.8 (br) ppm. | 361 |

-continued

| Number | Compound | logP (HCOOH) | NMR data | Mass M⁺ + 1 |
| --- | --- | --- | --- | --- |
| 13 | | 2.94 | 1H NMR (d6-DMSO): 7.70 (m, 3H), 7.88 (m, 1H), 8.08 (m, 3H), 8.30 (m, 2H), 8.75 (m, 1H), 8.90 (s, 1H), 9.12 (m, 1H), 12.3 (br) ppm. | 441 |
| 14 | | 2.15 | 1H NMR (d6-DMSO): 3.74 (s, 6H), 7.59 (dd, 1H), 7.94 (dd, 1H), 8.07 (t, 1H), 8.35 (dt, 1H), 8.51 (s, 1H) k, 8.60 (d, 1H), 9.13 (m, 1H), 9.26 ppm (d, 1H). | 412 |
| 15 | | 1.42 | 1H NMR (d6-DMSO): 6.86 (br. s, 1H), 7.33 (d, 1H), 7.59 (dd, 1H), 7.63 (dd, 1H), 7.72 (t, 1H), 7.94 (br. s, 1H), 8.15 (t, 1H), 8.22 (m, 1H), 8.31 (br. s, 1H), 8.57 (m, 1H), 8.67 (d, 1H), 8.87 (br. s, 1H), 9.09 (d, 1H), 11.34 ppm (br. s, 1H). | 379.1 |
| 16 | | 2.42 | 1H NMR (d6-DMSO): 2.65 (s, 6H), 7.76-7.84 (m, 3H), 8.30-8.34 (m, 1H), 8.45 (s, 1H), 8.57-8.58 (m, 1H), 9.11 (s, 1H), 9.24 (s, 1H) | 390 |
| 17 | | 2.4 | 1H NMR (d6-DMSO): 3.42 (s, 3H), 8.01 (m, 1H), 8.18 (m, 1H), 8.32 (m, 2H), 8.78 (s, 1H), 8.92 (m, 1H), 9.18 (s, 1H), 11.8 (br) ppm. | 395 |
| 18 | | 2.33 | 1H NMR (d6-DMSO): 1.28 (t, 3H), 3.55 (q, 2H), 7.98 (m, 1H), 8.15 (m, 1H), 8.33 (m, 2H), 8.72 (m, 1H), 8.90 (m, 1H), 9.11 (s, 1H), 11.8 (br) ppm. | 393 |

| Number | Compound | logP (HCOOH) | NMR data | Mass M⁺ + 1 |
|---|---|---|---|---|
| 19 | | 1.48 | 1H NMR (d6-DMSO): 1.29 (t, 3H), 3.61 (br. q, 2H), 6.83 (d, 1H), 7.44 (d, 1H), 7.61 (m, 1H), 7.77 (t, 1H), 8.29 (m, 1H), 8.58 (m, 1H), 9.07 (m, 1H), 9.16 (d, 1H), 10.45 ppm (br. s, 1H). | 330.1 |
| 20 | | 2.61 | 1H NMR (d6-DMSO): 1.38 (d, 6H), 3.85 (m, 1H), 7.99 (m, 1H), 8.15 (m, 1H), 8.35 (m, 2H), 8.75 (s, 1H), 8.92 (s, 1H), 9.11 (s, 1H), 11.8 (br) ppm. | 407.1 |
| 21 | | 2.97 | 1H NMR (d6-DMSO): 4.85 (s, 2H), 7.48 (m, 5H), 8.00 (m, 1H), 8.18 (m, 1H), 8.33 (m, 2H), 8.72 (s, 1H), 8.89 (s, 1H), 9.10 (s, 1H), 11.8 (br) ppm. | 455.1 |
| 22 | | 1.38 | 1H NMR (d6-DMSO): 3.44 (s, 3H), 7.98-8.00 (m, 1H), 8.08-8.15 (m, 2H), 8.84 (s, 1H); 9.20 (s, 1H), 9.38 (s, 2H), 9.54 (s, 1H), 11.75 (s, 1H) | 344 |
| 23 | | 2.24 | 1H NMR (D6-DMSO): 7.39-7.42 (m, 3H), 7.74-7.88 (m, 5H), 8.43 (s, 1H), 9.15 (s, 1H), 9.19-9.20 (m, 1H), 9.39 (s, 2H) ppm | 406.0 |
| 24 | | 1.48 | 1H NMR (D6-DMSO): 3.43 (s, 3H), 7.61-7.64 (m, 1H), 7.96-7.99 (m, 1H), 8.09-8.11 (m, 2H), 8.28-8.31 (m, 1H), 8.58-8.60 (m, 1H), 8.75 (s, 1H), 9.17-9.18 (m, 1H), 9.50 (s 1H), 11.70 (s, 1H) ppm | 344.0 |

-continued

| Number | Compound | logP (HCOOH) | NMR data | Mass M+ + 1 |
|---|---|---|---|---|
| 25 | | 1.77 | 1H NMR (D6-DMSO): 1.31 (t, 3H), 3.59 (q, 2H), 7.61-7.64 (m, 1H), 7.95-7.97 (m, 1H), 8.09-8.11 (m, 2H), 8.28-8.32 (m, 1H), 8.56-8.60 (m, 1H), 8.76 (s, 1H), 9.17-9.18 (m, 1H), 9.49 (s, 1H), 11.70 (s, 1H) ppm | 358.1 |
| 26 | | 2.21 | 1H NMR (D6-DMSO): 1.16 (t, 3H), 2.49-2.52 (m, 2H), 7.79-7.89 (m, 3H), 8.33-8.36 (m 1H), 8.47 (s, 1H), 8.57-8.58 (m, 1H), 9.11 (s, 1H), 9.25 (s, 1H) ppm | 376.0 |
| 27 | | 1.96 | 1H NMR (D6-DMSO): 2.95 (s, 6H), 7.61-7.64 (m 1H), 7.94-7.97 (m, 1H), 8.09-8.10 (m, 1H), 8.59-8.60 (m, 1H), 8.74 (s, 1H), 9.18-9.19 (m, 1H), 9.49 (s, 1H), 11.40 (s, 1H) ppm | 373.1 |
| 28 | | 1.76 | 1H NMR (D6-DMSO): 1.14-1.17 (M, 2H); 1.24-1.26 (m, 2H), 3.15-3.22 (m, 1H), 7.98-8.00 (m, 1H), 8.08-8.15 (m, 2H); 8.83 (s, 1H), 9.20 (s, 1H), 9.38 (s, 1H), 9.52 (s, 1H), 11.7 (s, 1H) ppm | 371.0 |
| 29 | | 2.35 | | 388.0 |
| 30 | | 1.85 | 1H NMR (D6-DMSO): 1, 12-1.17 (m, 2H), 1.23-1.27 (m, 2H), 7.61-7.64 (m, 1H), 7.95-8.00 (m 2H), 8.08-8.11 (m, 2H), 8.28-8.32 (m, 1H), 8.59-8.60 (m, 1H), 8.75 (s, 1H), 9.17-9.18 (m, 1H), 9.48 (s, 1H), 11.80 (s, 1H) ppm | 370.1 |

| Number | Compound | logP (HCOOH) | NMR data | Mass M+ + 1 |
|---|---|---|---|---|
| 31 | | 2.82 | 1H NMR (D6-DMSO): 7.38-7.42 (m, 3H), 7.74-7.88 (m, 5H), 8.32-8.36 (m, 1H), 8.39 (s, 1H), 8.56-8.58 (m, 1H), 9.10 (s, 1H), 9.18 (s, 1H) ppm | 424.0 |
| 32 | | 2.26 | 1H NMR (D6-DMSO): 7.42-7.43 (m, 3H), 7.55-7.59 (m, 1H), 7.76-7.89 (m, 5H), 8.31-8.34 (m, 1H), 8.38 (s, 1H), 8.54-8.56 (m, 1H), 9.14 (s, 1H), 9.17-9.18 (m, 1H) ppm | 406.0 |
| 33 | | 2.89 | 1H NMR (D6-DMSO): 4.48 (s, 2H), 7.24-7.34 (m, 5H), 7.72-7.90 (m, 3H), 8.33-8.36 (m, 1H), 8.46 (s, 1H), 8.57-8.58 (m, 2H), 9.1 (s, 1H), 9.25 (s, 1H) ppm | 438.1 |
| 34 | | 2.28 | 1H NMR (D6-DMSO): 4.44 (s 2H), 7.24-7.34 (m, 5H), 7.72-7.83 (m, 3H), 8.47 (s, 1H), 9.16 (s, 1H), 9.24 (s, 1H), 9.41 (s, 2H) ppm | 421.1 |
| 35 | | 2.44 | 1H NMR (D6-DMSO): 4.48 (s, 2H), 7.24-7.34 (m, 5H), 7.57-7.60 (m, 1H), 7.73-7.84 (m, 3H), 8.32-8.35 (m, 1H), 8.42 (s, 1H), 8.55-8.57 (m, 1H), 9.19-9.20 (m, 2H) ppm | 420.2 |

-continued

| Number | Compound | logP (HCOOH) | NMR data | Mass M⁺ + 1 |
|---|---|---|---|---|
| 36 (PE G) | | 1.25 | 1H NMR (D6-DMSO): 3.38 (S, 3H), 7.48-7.49 (m, 1H), 8.32-8.35 (m, 1H), 8.45 (s, 1H), 8.56 (s, 1H), 8.59-8.60 (m, 1H), 9.19-9.20 (m, 1H), 9.34 (s, 1H) ppm | 350.1 |
| 37 | | 1.66 | 1H NMR (D6-DMSO): 8.33-8.37 (m, 1H), 8.46 (s, 1H), 8.51 (s, 1H), 8.61-8.62 (m, 1H), 9.11 (s, 1H), 9.39 (s, 1H) ppm | 368.0 |
| 38 | | 2.36 | 1H NMR (D6-DMSO): 1.15 (t, 6H), 3.44 (q, 4H), 7.94-7.96 (m, 1H), 8.06-8.13 (m, 2H), 8.81 (s, 1H), 9.20 (s, 1H), 9.38 (s, 2H), 8.52 (s, 1H) ppm | 402.1 |
| 39 | | 2.98 | 1H NMR (D6-DMSO): 1.14 (t, 6H), 3.43 (q, 4H), 7.93-7.95 (m, 1H), 8.05-8.12 (m, 2H), 8.27-8.31 (m, 1H), 8.61-8.62 (m, 1H), 8.77 (s, 1H), 9.10 (s, 1H), 9.50 (s; 1H) ppm | 419.1 |
| 40 | | 2.49 | 1H NMR (D6-DMSO): 1.14 (t, 6H), 3.42 (q, 4H), 7.60-7.64 (m, 1H), 7.91-7.93 (m, 1H), 8.05-8.07 (m, 2H), 8.29-8.32 (m, 1H), 8.58-8.60 (m, 1H), 8.71 (s, 1H), 9.18-9.19 (m, 1H), 9.46 (s, 1H) ppm | 401.1 |
| 41 (PE F) | | 1.17 | 1H NMR (D6-DMSO): 2.03 (s, 3H), 7.60-7.64 (m, 1H), 7.92-7.94 (m, 1H), 8.08-8.10 (m, 1H), 8.17-8.20 (m, 1H), 8.29-8.31 (m, 1H), 8.37 (s, 1H), 8.59-8.60 (m, 1H), 9.16-9.17 (m, 1H), 9.26 (s, 1H), 12.31 (s, 1H) ppm | 344.1 |

-continued

| Number | Compound | logP (HCOOH) | NMR data | Mass M⁺ + 1 |
|---|---|---|---|---|
| 42 | | 1.43 | 1H NMR (D6-DMSO): 0.92 (t, 3H), 2.32 (q, 2H), 7.60-7.64 (m, 1H), 7.92-7.94 (1H), 8.07-8.09 (m, 1H), 8.17-8.20 (m, 1H), 8.28-8.31 (m, 1H), 8.36 (s, 1H), 8.59-8.60 (m, 1H), 9.16-9.17 (m, 1H), 9.26 (2H), 12.3 (s, 1H) ppm | 358.1 |
| 43 | | 1.49 | 1H NMR (D6-DMSO): 0.66-0.70 (m, 2H), 0.83-0.86 (m, 2H), 1.84 (m, 1H), 7.60-7.64 (m, 1H), 7.89-7.91 (m, 1H), 8.05-8.10 (m, 1H), 8.16-8.19 (m, 1H), 8.29-8.32 (m, 1H), 8.36 (s, 1H), 8.58-8.60 (m, 1H), 9.17-9.18 (m, 1H), 9.28 (s, 1H), 12.6 (br, 1H) ppm | 370.1 |
| 44 | | 1.55 | 1H NMR (D6-DMSO): 2.08 (s, 3H), 7.93-7.95 (m, 1H), 8.06-8.08 (m, 1H), 8.18-8.22 (m 1H), 8.30-8.32 (m, 1H), 8.39 (s, 1H), 8.62-8.63 (m, 1H), 9.09 (s, 1H), 9.31 (s, 1H) ppm | 362.1 |
| 45 | | 1.16 | 1H NMR (D6-DMSO): 3.20 (S, 1H), 7.59-7.62 (m, 1H), 8.26 (s, 1H), 8.27-8.30 (m, 2H), 8.40 (s, 1H), 8.57-8.58 (m, 1H), 9.13 (s, 1H), 9.14-9.15 (m, 1H) ppm | 305.1 |
| 46 (PE H) | | 1.68 | 1H NMR (D6-DMSO): 2.99, (s, 3H), 7.96 (s, 1H), 8.33 (s, 1H), 8.34 (s, 1H), 8.55-8.57 (m, 1H), 9.10 (s, 1H), 9.12 (s, 1H) ppm | 368.0 |
| 47 | | 1.4 | 1H NMR (D6-DMSO): 3.65 (3, 1H), 7.92-7.93 (m, 1H), 8.04-8.06 (m, 1H), 8.16-8.20 (m, 1H), 8.29-8.33 (m, 1H), 8.35 (s, 1H), 8.63-8.64 (m, 1H), 9.09 (s, 1H), 9.28 (s, 1H) ppm | 438.1 |
| 48 | | | 1H NMR (DMSO-d6): 7.60-7.62 (1H, m), 8.24-8.29 (2H, m), 8.38-8.41 (2H, m), 8.27-8.73 (1H, s), 9.20-9.21 (1H, m) ppm | 282 (HCl salt-free) |

| Number | Compound | logP (HCOOH) | NMR data | Mass M⁺ + 1 |
|---|---|---|---|---|
| 49 | | | 1H NMR (CDCl3) δ: 9.27-9.25 (2H, m), 8.71-8.69 (1H, m), 8.37 (1H, s), 8.32-8.29 (1H, m), 7.89-7.77 (3H, m), 7.45-7.41 (1H, m), 4.04 (3H, s) ppm | |
| 50 (PE J) | | | 1H NMR (CDCl3) δ: 9.24 (1H, s), 9.06 (1H, s), 8.56 (1H, s), 8.38 (1H, s), 8.07-8.05 (1H, m), 7.91-7.87 (1H, m), 7.81-7.79 (2H, m), 4.05 (3H, s) ppm | |
| 51 | | 1.95 | 1H NMR (d6-DMSO) = 3.4 (s, 3H), 8.02 (m, 1H), 8.20 (m, 1H), 8.33 (m, 1H), 8.95 (m, 2H), 9.15 (m, 1H), 9.48 (m, 1H), 11.80 (br, 1H) ppm. | 386.0 |
| 52 | | 2.275 | 1H NMR (d6-DMSO) = 3.35 (s, 3H), 3.57 (s, 3H), 7.68 (m, 1H), 8.12 (m, 1H), 8.30 (m, 2H), 8.72 (m, 1H), 8.80 (m, 1H), 9.11 (m, 1H) ppm. | 393.0 |
| 53 | | 2.54 | 1H NMR (d6-DMSO) = 2.95 (s, 6H), 8.00 (m, 1H), 8.17 (m, 1H), 8.35 (m, 2H), 8.75 (m, 1H), 8.95 (m, 1H), 9.11 (m, 1H), 11.5 (br, 1H) ppm. | 408.0 |
| 54 | | 3.29 | 1H NMR (d6-DMSO) = 1.4-1.6 (m, 6H), 3.2-3.4 (m, 4H), 7.99 (m, 1H), 8.18 (m, 1H), 8.33 (m, 2H), 8.75 (m, 1H), 8.89 (m, 1H), 9.12 (m, 1H), 11.3 (br, 1H) ppm. | 448.0 |
| 55 | | 2.19 | 1H NMR (d6-DMSO) = 3.15 (m, 2H), 3.78 (m, 2H), 7.97 (m, 1H), 8.18 (m, 1H), 8.33 (m, 2H), 8.72 (m, 1H), 8.90 (m, 1H), 9.10 (m, 1H), 11.7 (br, 1H) ppm. | 423.1 |

-continued

| Number | Compound | logP (HCOOH) | NMR data | Mass M⁺ + 1 |
|---|---|---|---|---|
| 56 | | 2.77 | 1H NMR (d6-DMSO) = 1.40 (s, 9H), 7.90 (m, 1H), 8.10 (m, 1H), 8.30 (m, 2H), 8.71 (m, 1H), 8.85 (m, 1H), 9.09 (m, 1H), 11.0 (br, 1H) ppm. | 421.1 |
| 57 | | 2.58 | 1H NMR (d6-DMSO) = 4.71 (m, 2H), 7.99 (m, 1H), 8.15 (m, 1H), 8.33 (m, 2H), 8.74 (m, 1H), 8.88 (m, 1H), 9.11 (m, 1H) ppm. | 447.0 |
| 58 | | 3 | 1H NMR (d6-DMSO) = 2.69 (s, 6H), 7.90 (m, 1H), 8.05 (m, 1H), 8.25 (m, 1H), 8.33 (m, 1H), 8.71 (m, 1H), 8.84 (m, 1H), 9.11 (m, 1H) ppm. | 460.0 |
| 59 | | 3.41 | 1H NMR (d6-DMSO) = 2.55 (s, 3H), 7.91 (m, 1H), 8.05 (m, 1H), 8.25 (m, 1H), 8.32 (m, 1H), 8.71 (m, 1H), 8.81 (m, 1H), 9.10 (m, 1H) ppm. | 495.9 |
| 60 | | 3.09 | 1H NMR (d6-DMSO) = 1.05 (d, 6H), 2.85 (s, 3H), 4.18 (m, 1H), 7.98 (m, 1H), 8.17 (m, 1H), 8.32 (m, 2H), 8.72 (m, 1H), 8.90 (m, 1H), 9.11 (m, 1H) ppm. | 436.0 |
| 61 | | 3.47 | 1H NMR (d6-DMSO) = 0.3-1.2 (m, 8H), 2.99 (s, 3H), 3.30 (m, 1H), 7.98 (m, 1H), 8.16 (m, 1H), 8.31 (m, 2H), 8.72 (m, 1H), 8.90 (m, 1H), 9.11 (m, 1H) ppm. | 462.0 |

-continued

| Number | Compound | logP (HCOOH) | NMR data | Mass M+ + 1 |
|---|---|---|---|---|
| 62 | | 1.9 | 1H NMR (d6-DMSO) = 2.95 (s, 6H), 8.00 (m, 1H), 8.17 (m, 1H), 8.32 (m, 1H), 8.95 (m, 1H), 9.30 (m, 1H), 9.40 (m, 1H), 11.4 (m, 1H) ppm. | 391.0 |
| 63 (PE I) | | 2.04 | 1H NMR (d6-DMSO) =- 2.55 (s, 3H), 3.40 (s, 3H), 4.12 (s, 3H), 7.68 (m, 1H), 8.12 (m, 1H), 8.69 (m, 1H), 9.01 (m, 1H) ppm. | 396.0 |
| 64 | | 1.84 | 1H NMR (d6-DMSO) = 2.45 (s, 3H), 3.25 (s, 3H), 3.90 (s, 3H), 7.12 (m, 1H), 8.29 (m, 1H), 8.72 (m, 1H), 9.04 (m, 1H) ppm. | 396.0 |
| 65 | | 2.28 | 1H NMR (d6-DMSO) = 3.71 (s, 3H), 4.98 (s, 2H), 7.70 (m, 1H), 8.17 (m, 1H), 8.35 (m, 2H), 8.75 (m, 1H), 8.85 (m, 1H), 9.09 (m, 1H) ppm. | 418.1 |
| 66 | | 2.01 | 1H NMR (d6-DMSO) = 2.93 (s, 6H), 7.60 (m, 1H), 8.00 (m, 1H), 8.15 (m, 1H), 8.32 (m, 1H), 8.40 (m, 1H), 8.73 (m, 1H), 8.90 (m, 1H), 9.23 (m, 1H), 11.5 (br, 1H) ppm. | 390.0 |
| 67 | | 1.72 | 1H NMR (d6-DMSO) = 2.01 (s, 3H), 8.03 (m, 1H), 8.25 (m, 2H), 8.40 (m, 1H), 8.78 (m, 1H), 8.80 (m, 1H), 9.09 (m, 1H), 12.3 (br, 1H) ppm. | 379.0 |
| 68 | | 2.56 | 1H NMR (d6-DMSO) = 3.65 (s, 3H), 4.71 (s, 2H), 7.70 (m, 1H), 8.12 (m, 1H), 8.32 (m, 2H), 8.71 (m, 1H), 8.81 (m, 1H), 9.10 (m, 1H) ppm. | 417.0 |

-continued

| Number | Compound | logP (HCOOH) | NMR data | Mass M+ + 1 |
|---|---|---|---|---|
| 69 (PE E) | | 1.3 | 1H NMR (d6-DMSO) = 2.03 (s, 3H), 7.61 (m, 1H), 8.02 (m, 1H), 8.13 (m, 1H), 8.30 (m, 1H), 8.41 (m, 1H), 8.71 (m, 1H), 8.91 (m, 1H), 9.20 (m, 1H) ppm. | 361.0 |
| 70 | | 2.07 | 1H NMR (d6-DMSO) = 1.3 (t, 3H), 3.6 (m, 2H), 8.2 (m, 1H), 8.3 (m, 1H) 8.45 (m, 1H), 8.6 (m, 1H) 8.85 (s, 1H) 9.2 (s, 1H) 12 (s, 1H) ppm | 393.4 |
| 71 | | 2.14 | 1H NMR (d6-DMSO) = 1.15 (m, 2H), 1.25 (m, 1.25), 3.15 (m, 1H), 8.2 (m, 1H), 8.3 (m, 1H) 8.45 (m, 1H), 8.6 (m, 1H) 8.85 (s, 1H) 9.2 (s, 1H) 12 (s, 1H) ppm | 405 |
| 72 | | 2.31 | 1H NMR (d6-DMSO) = 1.35 (d, 6H), 3.8 (m, 1H), 8.2 (m, 1H), 8.3 (m, 1H) 8.45 (m, 1H), 8.6 (m, 1H) 8.85 (s, 1H) 9.2 (s, 1H) 12 (s, 1H) ppm | 407 |
| 73 | | 2.42 | | 447 |

-continued

| Number | Compound | logP (HCOOH) | NMR data | Mass M⁺ + 1 |
|---|---|---|---|---|
| 74 | | 1.97 | 1H NMR (d6-DMSO) = 3.2 (m, 3H), 3.75 (s, 2H), 3.8 (m, 2H) 8.2 (m, 1H), 8.3 (m, 1H), 8.5 (m, 1H), 8.6 (m, 1H) 8.85 (s, 1H) 9.2 (s, 1H) 12 (s, 1H) ppm | 423 |
| 75 | | 2.38 | | 447 |
| 76 | | 1.43 | | 506 |

-continued

| Number | Compound | logP (HCOOH) | NMR data | Mass M⁺ + 1 |
|---|---|---|---|---|
| 77 | | 2.38 | | 421 |
| 78 | | 3.08 | | 482 |
| 79 (PE K) | | | 1H NMR (DMSO-D6) δ: 9.08-9.07 (1H, m), 8.93 (1H, s), 8.75-8.74 (1H, m), 8.41-8.39 (1H, m), 8.31-8.26 (2H, m), 8.22-8.19 (1H, m) ppm | 300 (HCl salt-free) |

The preparation processes described above were used to obtain the following intermediates of the formula (XII):

| Number | Compound | logP (HCOOH) | NMR data |
|---|---|---|---|
| XII-1 | | 2.4 | 1H NMR (D6-DMSO): 4.83 (s, 3H), 7.34-7.40 (m, 5H), 7.94-7.95 (m, 1H), 7.98-8.00 (m, 1H), 8.05-8.07 (m, 1H), 12.3 (bs, 1H) |
| XII-2 | | 1.82 | 1H NMR (D6-DMSO): 2.90 (s, 6H), 7.93-8.00 (m, 2H), 8.04-8.06 (m, 1H), 11.80 (s, 1H) |

| Number | Compound | logP (HCOOH) | NMR data |
|---|---|---|---|
| XII-3 | | 1.15 | ¹H NMR (d6-DMSO): 3.33 (s, 3H), 7.78 (m, 1H), 8.05 (m, 2H) ppm. |
| XII-4 | | 1.28 | ¹H NMR (d6-DMSO): 3.37 (s, 3H), 7.95 (m, 2H), 8.06 (m, 1H) ppm. |
| XII-5 | | 1.54 | 1H NMR (D6-DMSO): 1.27 (t, 3H), 3.50 (q, 2H), 7.94-8.01 (m, 2H), 8.05-8.07 (m, 1H), 11.90 (s, 1H) |
| XII-6 | | 2.32 | 1H NMR (DMSO): 7.57-7.70 (m, 3H), 7.84-8.01 (m, 5H) |
| XII-7 | | 1.7 | 1H NMR (D6-DMSO): 1.07-1.21 (m, 4H), 3.05-3.11 (m, 1H), 7.93-8.01 (m, 3H), 8.06-8.08 (m, 2H), 12.00 (s, 1H) |

The preparation processes described above were used to obtain the following intermediates of the formula (XIII):

| Number | Compound | logP (HCOOH) | NMR data |
|---|---|---|---|
| XIII-1 | | 1.51 | 1H NMR (DMSO): 7.93 (m, 1H), 8.03 (m, 1H), 8.17 (m, 1H), 8.63 (m, 1H), 9.02 (m, 1H) |
| XIII-2 | | 1.94 | 1H NMR (DMSO): 7.96 (m, 1H), 8.05 (m, 1H), 8.42 (m, 1H), 8.73 (m, 1H), 9.11 (m, 1H) |
| XIII-3 | | 0.69 | 1H NMR (DMSO): 7.95 (m, 1H), 8.07 (m, 1H), 9.25 (m, 1H), 9.30 (m, 2H) |

-continued

| Number | Compound | logP (HCOOH) | NMR data |
|---|---|---|---|
| XIII-4 | NC-pyridine-thiazole | 1.34 | 1H NMR (DMSO): 8.00 (m, 1H), 8.08 (m, 1H), 8.83 (m, 1H) 9.12 (m, 1H), 9.40 (m, 1) |

The preparation processes described above were used to obtain the following intermediates of the formula (XIV):

| Number | Compound | logP (HCOOH) | NMR data |
|---|---|---|---|
| XIV-1 | Br-pyridine-SO2-NH-C(O)Et | 1.32 | 1H NMR (d6-DMSO): 0.92 (t, 3H), 2.28 (q, 2H), 7.99 (m, 1H), 8.06-8.23 (m, 2H), 12.39 (br, 1H) |
| XIV-2 | Br-pyridine-SO2-NH-C(O)Me | 0.95 | 1H NMR (d6-DMSO): 1.98 (s, 3H), 7.98-8.12 (m, 3H), 12.4 (br, 1H) ppm |

The preparation processes described above were used to obtain the following intermediates of the formula (XV):

| Number | Compound | logP (HCOOH) | NMR data |
|---|---|---|---|
| XV-1 | Br-thiazole-C(O)NH-SO2Me | 0.82 | 1H NMR (d6-DMSO): 3.33 (s, 3H), 8.61 (s, 1H), 12.00 (s, 1H) |

The preparation processes described above were used to obtain the following intermediates of the formula (XVI):

| Number | Compound | logP (HCOOH) | NMR data |
|---|---|---|---|
| XVI-1 | Br-thiazole-C(O)NH-SO2Me | 0.63 | 1H NMR (d6-DMSO): 3.31 (s, 3H), 8.31 (s, 1H) |

The preparation processes described above were used to obtain the following intermediates of the formula (XVII):

| Number | Compound | logP (HCOOH) | NMR data |
|---|---|---|---|
| XVII-1 | pyrazole-pyridine-SO2NH2 with pyridyl | 0.99 | 1H NMR (d6-DMSO): 7.43 (s, 2H), 7.60-7.63 (m, 1H), 7.76 (d, 1H), 8.00 (d, 1H), 8.11 (t, 1H), 8.28-8.31 (m, 1H), 8.53 (s, 1H), 8.58-8.60 (m, 1H), 9.16-9.17 (m, 1H), 9.33 (s, 1H) |

| Number | Compound | logP (HCOOH) | NMR data |
|---|---|---|---|
| XVII-2 | (structure) | 1.44 | 1H NMR (d6-DMSO): 7.78 (s, 2H), 7.77-7.79 (m, 1H), 7.99-8.01 (m, 1H), 8.12-8.14 (m, 1H), 8.29-8.32 (m, 1H), 8.57 (s, 1H), 8.62-8.63 (m, 1H), 9.09 (s, 1H), 9.41 (s, 1H) |
| XVII-3 | (structure) | 0.89 | 1H NMR (d6-DMSO): 7.48 (s, 2H), 7.78-7.80 (m, 1H), 7.99-7.80 (m, 1H), 8.12-8.16 (m, 1H), 8.60 (s, 1H), 9.21 (s, 1H), 9.38 (s, 2H), 9.41 (s, 1H) |

1) Description of Method for Determination of the Log P Values (Formic Acid Method)

The Log P values given in the table were determined in accordance with EEC Directive 79/831 Annex V.A8 by HPLC (High Performance Liquid Chromatography) using a reverse-phase column (C18). Temperature: 55° C.

Eluents for determination in the acidic range (pH 3.4):

Eluent A: acetonitrile+1 ml of formic acid/liter. Eluent B: water+0.9 ml of formic acid/liter.

Gradient: from 10% eluent A/90% eluent B to 95% eluent A/5% eluent B in 4.25 min.

The calibration was effected with unbranched alkan-2-ones (having 3 to 16 carbon atoms) with known Log P values (logP values determined on the basis of the retention times by linear interpolation between two successive alkanones). The lambda max values were determined in the maxima of the chromatographic signals using the UV spectra from 200 nm to 400 nm.

2) Measurement of the NMR Spectra

The NMR spectra were determined with a Bruker Avance 400 fitted with a flow probe head (volume 60 µl). The solvent used was $CD_3CN$ or $d_6$-DMSO, with tetramethylsilane (0.00 ppm) used as a reference. In particular cases, the NMR spectra were determined with a Bruker Avance II 600. The solvent used was $CD_3CN$ or $d_6$-DMSO, with tetramethylsilane (0.00 ppm) used as a reference.

The splitting of the signals was described as follows: s (singlet), d (doublet), t (triplet), q (quartet), quin (quintet), m (multiplet).

Biological Examples

Myzus Test (Spray Treatment)

Solvent: 78 parts by weight of acetone
1.5 parts by weight of dimethylformamide
Emulsifier: 0.5 part by weight of alkylaryl polyglycol ether To prepare an appropriate active ingredient preparation, 1 part by weight of active ingredient is mixed with the stated amounts of solvent and emulsifier, and the concentrate is diluted with emulsifier-containing water to the desired concentration.

Discs of Chinese cabbage (*Brassica pekinensis*) infested by all stages of the green peach aphid (*Myzus persicae*) are sprayed with an active ingredient preparation of the desired concentration.

After the desired time, the efficacy in % is determined. 100% means that all of the aphids have been killed; 0% means that none of the aphids have been killed.

In this test, for example, the following compounds of the Preparation Examples showed, at an application rate of 500 g/ha, an efficacy of 80%: 1, 10, 15, 21, 28, 62, 63

In this test, for example, the following compounds of the Preparation Examples showed, at an application rate of 500 g/ha, an efficacy of 90%: 5, 14, 23, 32, 34, 37, 38, 45, 47, 48, 65, 74

In this test, for example, the following compounds of the Preparation Examples showed, at an application rate of 500 g/ha, an efficacy of 100%: 2, 3, 4, 6, 7, 8, 9, 11, 12, 13, 16, 17, 18, 19, 20, 22, 24, 25, 26, 27, 29, 30, 31, 33, 35, 36, 39, 40, 41, 42, 43, 44, 46, 51, 52, 53, 54, 55, 56, 57, 58, 59, 60, 61, 64, 66, 67, 68, 69, 70, 71, 72, 73, 75, 76, 77, 78.

*Tetranychus* Test, OP-Resistant (Spray Treatment)

Solvent: 78.0 parts by weight of acetone
1.5 parts by weight of dimethylformamide
Emulsifier: 0.5 part by weight of alkylaryl polyglycol ether To prepare an appropriate active ingredient preparation, 1 part by weight of active ingredient is mixed with the stated amounts of solvent and emulsifier, and the concentrate is diluted with emulsifier-containing water to the desired concentration. Discs of bean leaves (*Phaseolus vulgaris*) infested by all stages of the red spider mite (*Tetranychus urticae*) are sprayed with an active ingredient preparation of the desired concentration.

After the desired time, the efficacy in % is determined. 100% means that all of the spider mites have been killed; 0% means that none of the spider mites have been killed.

In this test, for example, the following compound of the Preparation Examples showed, at an application rate of 500 g/ha, an efficacy of 100%: 5.

*Meloidogyne Incognita* Test

Solvent: 80.0 parts by weight of acetone

To prepare an appropriate active ingredient preparation, 1 part by weight of active ingredient is mixed with the stated amounts of solvent, and the concentrate is diluted with water to the desired concentration.

Vessels are filled with sand, active ingredient solution, *Meloidogyne incognita* egg/larvae suspension and lettuce seeds. The lettuce seeds germinate and the plants develop. Galls develop on the roots.

After the desired time, the nematicidal action is determined by the gall formation in %. 100% means that no galls were found; 0% means that the number of galls on the treated plants corresponds to the untreated control.

In this test, for example, the following compounds of the preparation examples showed, at an application rate of 20 ppm, an efficacy of 100%: 56, 70, 75, 78.

Myzus Spray Test

Preliminary mixture solvent: Sorpol® SD: Sorpol® BDB: dimethylformamide=3:3:14

To prepare an appropriate active ingredient preparation, 10 mg of active ingredient are mixed with 0.05 ml of solvent and the concentrate is diluted with water to the desired concentration. The solution in each case contains 1000 ppm of RME (rapeseed oil methyl ester) and AMS (ammonium sulphate).

Aubergine plants (*Solanum melongena* var. *Senryo* 2gou) infested by all stages of the green peach aphid (*Myzus persicae* organophosphate/carbamate resistant strain) are sprayed, with an active ingredient preparation of the desired concentration.

After 6 days, the efficacy in % is determined:
100%: all insects killed,
98%: 1-4 insects survive,
95%: 5-20 insects survive,
60%: fewer insects survive than in the untreated control and
0%: no difference from the untreated control.

In this test, for example, the following compounds of the preparation examples showed, at an application rate of 100 ppm, an efficacy of 100%: 49, 50.

The invention claimed is:
1. A compound of the formula (I)

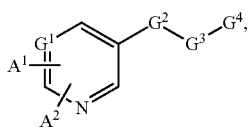

in which
$A^1$ and $A^2$ are each independently hydrogen, halogen, cyano, nitro, alkyl, cycloalkyl or alkoxy,
$G^1$ is $C\text{-}A^1$,
$G^2$ is a radical

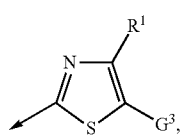

in which the arrow marks the bond to the adjacent ring,
$R^1$ is hydrogen, halogen, cyano, alkyl, alkoxy, amino, alkylamino, dialkylamino, alkylthio or haloalkyl,
$G^3$ is a substituted pyridyl

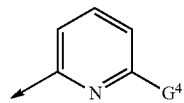

and
$G^4$ is a radical (E), (L) or (N)

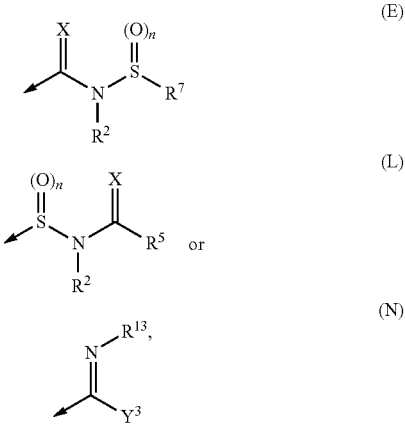

in which the arrow in each case marks the bond to $G^3$,
X is oxygen or sulphur,
n is 1 or 2,
$R^2$ is in each case hydrogen, alkyl, haloalkyl, cyanoalkyl, alkoxy, haloalkoxy, alkenyl, alkynyl or alkoxyalkyl, in each case optionally halogen-substituted alkylcarbonyl or alkylsulphonyl, in each case optionally halogen-substituted alkoxycarbonyl, in each case optionally halogen-, alkyl-, alkoxy-, haloalkyl- or cyano-substituted cycloalkylcarbonyl, or a cation,
$R^7$ is in each case optionally substituted alkyl, alkenyl or alkynyl, in each case optionally substituted cycloalkyl, cycloalkylalkyl or cycloalkenyl, in which the rings may contain at least one heteroatom selected from the group consisting of sulphur, oxygen (where oxygen atoms must not be immediately adjacent) and nitrogen, in each case optionally substituted aryl, heteroaryl, arylalkyl or heteroarylalkyl or an optionally substituted amino group,
$R^5$ is in each case optionally substituted alkyl, alkoxy, alkenyl or alkynyl, in each case optionally substituted cycloalkyl, cycloalkylalkyl or cycloalkenyl, in which the rings may contain at least one heteroatom selected from the group consisting of sulphur, oxygen (where oxygen atoms must not be immediately adjacent) and nitrogen, in each case optionally substituted aryl, heteroaryl, arylalkyl or heteroarylalkyl, or an optionally substituted amino group, or
$R^2$ and $R^5$ in the radical (L), together with the N—C(X) group to which they are bonded form a saturated or unsaturated and optionally substituted 4- to 8-membered ring which may contain one or more further heteroatoms selected from the group consisting of sulphur, oxygen (where oxygen atoms must not be immediately adjacent) and nitrogen and/or at least one carbonyl group, and
$R^2$ and $R^7$ in the radical (E), together with the N—S(O)$_n$ group to which they are bonded form a saturated or unsaturated and optionally substituted 4- to 8-membered ring which may contain one or more further heteroatoms selected from the group consisting of sulphur, oxygen (where oxygen atoms must not be immediately adjacent) and nitrogen, and/or at least one carbonyl group,
$R^{13}$ is a radical selected from the group consisting of hydrogen, alkyl, haloalkyl, cyano, cyanoalkyl, hydroxyalkyl, hydroxyl, alkoxy, alkoxyalkyl, alkylthioalkyl, alkenyl, haloalkenyl, cyanoalkenyl, alkynyl, haloalkynyl, cyanoalkynyl, alkylcarbonyl and alkoxycarbonyl, Y³ is a radical selected from the group consisting of alkoxy, haloalkoxy, alkylthio, haloalkylthio and NR¹⁴R¹⁵ where R¹⁴ and R¹⁵ are each independently radicals from the group of hydrogen, alkyl, cycloalkyl, cycloalkylalkyl, haloalkyl, cyano, cyanoalkyl, hydroxyl, alkoxy, haloalkoxy, hydroxyalkyl, alkoxyalkyl, alkylahoalkyl, alkenyl, haloalkenyl, cyanoalkenyl, alkynyl, haloalkynyl, cyanoalkynyl, alkylcarbonyl and alkoxycarbonyl, or R¹⁴ and R¹⁵ together with the nitrogen atom to which they are bonded may form an optionally substituted saturated or unsaturated 5- to 8-membered ring optionally containing heteroatoms, or G³ and G⁴ together form an optionally substituted heterocycle which optionally contains one or more further heteroatoms selected from the group consisting of oxygen, nitrogen and sulphur, and a salt or N-oxide of the compound of formula (I).

2. A compound of formula (IA)

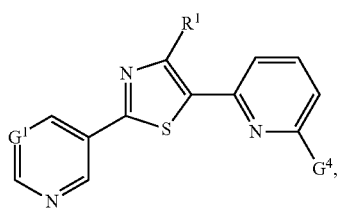

or a salt or N-oxide thereof,
in which
G¹ is C—H, C—F, or C—Cl,
R¹ is hydrogen or methyl, and
G⁴ is a radical (E), (L) or (N)

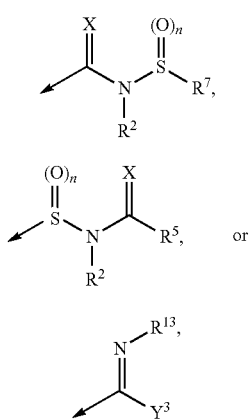

in which the arrow in each case marks the bond to the adjacent ring,
X is oxygen or sulphur,
n is 1 or 2,
R² is in hydrogen, alkyl, haloalkyl, cyanoalkyl, alkoxy, haloalkoxy, alkenyl, alkynyl or alkoxyalkyl, in each case optionally halogen-substituted alkylcarbonyl or alkylsulphonyl, in each case optionally halogen-substituted alkoxycarbonyl, in each case optionally halogen-, alkyl-, alkoxy-, haloalkyl- or cyano-substituted cycloalkylcarbonyl, or a cation, R⁷ is in each case optionally substituted alkyl, alkenyl or alkynyl, in each case optionally substituted cycloalkyl, cycloalkylalkyl or cycloalkenyl, in which the rings may contain at least one heteroatom selected from the group consisting of sulphur, oxygen (where oxygen atoms must not be immediately adjacent) and nitrogen, in each case optionally substituted aryl, heteroaryl, arylalkyl or heteroarylalkyl, or an optionally substituted amino group, or R² and R⁷ in the radical (E), together with the N—S(O)$_n$ group to which they are bonded form a saturated or unsaturated, and optionally substituted 4- to 8-membered ring which may contain one or more further heteroatoms selected from the group consisting of sulphur, oxygen (where oxygen atoms must not be immediately adjacent) and nitrogen, and/or at least one carbonyl group, R⁵ is in each case optionally substituted alkyl, alkoxy, alkenyl or alkynyl, in each case optionally substituted cycloalkyl, cycloalkylalkyl or cycloalkenyl, in which the rims may contain at least one heteroatom selected from the group consisting of sulphur, oxygen (where oxygen atoms must not be immediately adjacent) and nitrogen, in each case optionally substituted aryl, heteroaryl, arylalkyl or heteroarylalkyl, or an optionally substituted amino group, or R² and R⁵ in the radical (L), together with the N—C(X) group to which they are bonded form a saturated or unsaturated and optionally substituted 4- to 8-membered ring which may contain one or more further heteroatoms selected from the group consisting of sulphur, oxygen (where oxygen atoms must not be immediately adjacent) and nitrogen, and/or at, least one carbonyl group, or R¹³ is a radical selected from the group consisting of hydrogen, alkyl, haloalkyl, cyano, cyanolkyl, hydroxyalkyl, hydroxyl, alkoxy, alkoxyalkyl, alkylthioalkyl, alkenyl, haloalkenyl, cyanoalkenyl, alkynyl, haloalkynyl, cyanoalkynyl, alkylcarbonyl, and alkoxycarbonyl, and Y³ is a radical selected from the group consisting of alkoxy, haloalkoxy, alkylthio, haloalkylthio and NR¹⁴R¹⁵ where R¹⁴ and R¹⁵ are each independently radicals from the group of hydrogen, alkyl, cycloalkyl, cycloalkylalkyl, haloalkyl, cyano, cyanoalkyl, hydroxyl, alkoxy, haloalkoxy, hydroxyalkyl, alkoxyalkyl, alkylthioalkyl, alkenyl, haloalkenyl, cyanoalkenyl, alkynyl, haloalkynyl, cyanoalkynyl, alkylcarbonyl and alkoxycarbonyl, or R¹⁴ and R¹⁵ together with the nitrogen atom to which they are bonded may form an optionally substituted saturated or unsaturated 5- to 8-membered ring optionally containing heteroatoms.

3. The compound according to claim 1, or a salt or N-oxide thereof,
in which
A¹ and A² are each independently hydrogen, halogen, cyano, nitro, $C_1$-$C_6$-alkyl, $C_3$-$C_6$-cycloalkyl or $C_1$-$C_6$-alkoxy,
R¹ is hydrogen, halogen, cyano, $C_1$-$C_6$-alkyl, $C_1$-$C_6$-alkoxy or $C_1$-$C_6$-haloalkyl,
R² is in each case hydrogen, $C_1$-$C_6$-alkyl, $C_1$-$C_6$-haloalkyl, cyano-$C_1$-$C_6$-alkyl, $C_1$-$C_6$-alkoxy, $C_1$-$C_6$-haloalkoxy, $C_2$-$C_6$-alkenyl, $C_2$-$C_6$-alkynyl, or $C_1$-$C_6$-alkoxy-$C_1$-$C_6$-alkyl, in each case optionally halogen-substituted $C_1$-$C_6$-alkylcarbonyl or $C_1$-$C_6$-alkylsulphonyl, optionally halogen-substituted $C_1$-$C_6$-alkoxycarbonyl, in each case optionally halogen-, $C_1$-$C_6$-alkyl-, $C_1$-$C_6$-alkoxy-, $C_1$-$C_6$-haloalkyl- or cyano-substituted $C_3$-$C_6$-cycloalkylcarbonyl, or a mono or divalent metal ion, or an optionally $C_1$-$C_6$-alkyl- or aryl-$C_1$-$C_6$-alkyl-substituted ammonium ion, $R^7$ is in each case optionally halogen-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl- or $C_1$-$C_6$-haloalkylsulphonyl-substituted $C_1$-$C_6$-alkyl, $C_2$-$C_6$-alkenyl or $C_2$-$C_6$-alkynyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl, $C_3$-$C_6$-cycloalkyl-$C_1$-$C_6$-alkyl or $C_3$-$C_6$-cycloalkenyl, in which the rings may contain at least one heteroatom selected from the group consisting of sulphur, oxygen (where oxygen atoms must not be immediately adjacent) and nitrogen, or is in each case a radical

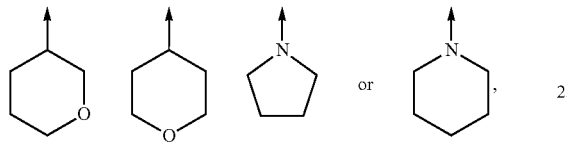

where the arrow in each case marks the bond to the sulphur atom in the radical (E), or is in each case optionally halogen-, cyano- (including in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-haloalkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted aryl, heteroaryl, aryl-$C_1$-$C_6$-alkyl or heteroaryl-$C_1$-$C_6$-alkyl, or NR'R" in which R' and R" are each independently a radical selected from the group consisting of hydrogen, $C_1$-$C_6$-alkyl, $C_1$-$C_6$-haloalkyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-alkylcarbonyl and $C_1$-$C_6$-alkoxylcarbonyl, $R^5$ is in each case optionally halogen-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-haloalkylsulphinyl-, $C_1$-$C_6$-alkylsulphonyl- or $C_1$-$C_6$-haloalkylsulphonyl-substituted $C_1$-$C_6$-alkyl, $C_1$-$C_6$-alkoxy, $C_2$-$C_6$-alkenyl or $C_2$-$C_6$-alkynyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl, $C_3$-$C_6$-cycloalkyl-$C_1$-$C_6$-alkyl or $C_3$-$C_6$-cycloalkenyl, in which the rings may contain at least one heteroatom selected from the group consisting of sulphur, oxygen (where oxygen atoms must not be immediately adjacent) and nitrogen, in each case optionally halogen-, cyano- (including in the alkyl moiety), nitro-, $C_1$-$C_6$-alkyl-, $C_1$-$C_6$-haloalkyl-, $C_3$-$C_6$-cycloalkyl-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted aryl, heteroaryl, aryl-$C_1$-$C_6$-alkyl or heteroaryl-$C_1$-$C_6$-alkyl, or NR'R" in which R' and R" are each independently a radical selected from the group consisting of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxylcarbonyl, or $R^2$ and $R^5$ in the radical (L), together with the N—C(X) group to which they are bonded, form a saturated or unsaturated and optionally halogen-, $C_1$-$C_6$-alkyl-, $C_1$-$C_6$-haloalkyl-, $C_1$-$C_6$-alkoxy-, or $C_1$-$C_6$-haloalkoxy-substituted 5- to 7-membered ring which may contain one or more further heteroatoms selected from the group consisting of sulphur, oxygen (where oxygen atoms must not be immediately adjacent) and nitrogen, and/or at least one carbonyl group, or $R^2$ and $R^5$ in the radical (L), together with the N—C(X) group to which they are bonded, form a radical

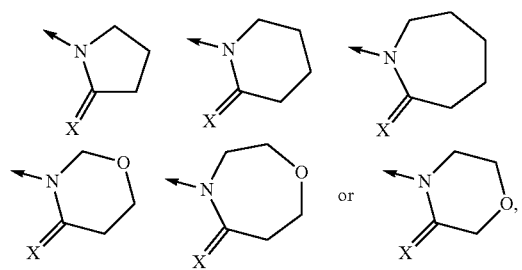

in which the arrow in each case marks the bond to the sulphur atom in the radical (L), or $R^2$ and $R^7$ in the radical (E), together with the N—S(O)$_n$ group to which they are bonded, form a saturated or unsaturated and optionally halogen-, $C_1$-$C_6$-alkyl-, $C_1$-$C_6$-haloalkyl-, $C_1$-$C_6$-alkoxy-, or $C_1$-$C_6$-haloalkoxy-substituted 5- to 7-membered ring which may contain one or more further heteroatoms selected from the group of consisting sulphur, oxygen (where oxygen atoms must not be immediately adjacent) and nitrogen, and/or at least one carbonyl, group, or $R^2$ and $R^7$ in the radical (E), together with the N—S(O)$_n$ group to which they are bonded, form a radical

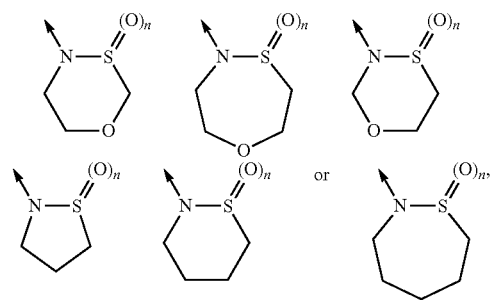

in which the arrow in each case marks the bond to the C(X) group, $R^{13}$ is a radical selected from the group consisting of hydrogen, $C_1$-$C_6$-alkyl, $C_1$-$C_6$-haloalkyl, cyano, $C_1$-$C_6$- cyanoalkyl, $C_1$-$C_6$-hydroxyalkyl, hydroxyl, $C_1$-$C_6$-alkoxy, $C_1$-$C_6$-alkoxy-$C_1$-$C_6$-alkyl, $C_1$-$C_6$-alkylthio-$C_1$-$C_6$-alkyl, $C_2$-$C_6$-alkenyl, $C_2$-$C_6$-haloalkenyl, $C_2$-$C_6$-cyanoalkenyl, $C_2$-$C_6$-alkynyl, $C_2$-$C_6$-haloalkynyl, $C_2$-$C_6$-cyanoalkynyl, $C_1$-$C_7$-alkylcarbonyl and $C_1$-$C_7$-alkoxycarbonyl, and $Y^3$ is a radical selected from the group consisting of $C_1$-$C_6$-alkoxy, $C_1$-$C_6$-haloalkoxy, $C_1$-$C_6$-alkylthio, $C_1$-$C_6$-haloalkylthio and $NR^{14}R^{15}$ where $R^{14}$ and $R^{15}$ are each independently a radical selected from the group consisting of hydrogen, $C_1$-$C_6$-alkyl, $C_3$-$C_8$-cycloalkyl, $C_3$-$C_8$-cycloalkyl-$C_1$-$C_6$-alkyl, $C_1$-$C_6$-haloalkyl, cyano, $C_1$-$C_6$-cyanoalkyl, hydroxyl, $C_1$-$C_6$-alkoxy, $C_1$-$C_6$-haloalkoxy, $C_1$-$C_6$-hydroxyalkyl, $C_1$-$C_6$-alkoxy-$C_1$-$C_6$-alkyl, $C_1$-$C_6$-alkylthio-$C_1$-$C_6$-alkyl, $C_2$-$C_6$-alkenyl, $C_2$-$C_6$-haloalkenyl, $C_2$-$C_6$-cyanoalkenyl, $C_2$-$C_6$-alkynyl, $C_2$-$C_6$-haloalkynyl, $C_2$-$C_6$-cyanoalkynyl, $C_1$-$C_7$-alkylcarbonyl and $C_1$-$C_7$-alkoxycarbonyl, or $R^{14}$ and $R^{15}$ together with the nitrogen atom to which they are bonded are, an optionally halogen-, cyano-, $C_1$-$C_6$-alkyl-, $C_1$-$C_6$-haloalkyl-, $C_1$-$C_6$-alkoxy-, $C_3$-$C_8$-cycloalkyl- or $C_1$-$C_6$-alkylthio-substituted saturated or unsaturated 5- to 8-membered ring which may contain one or more further atoms selected from the group consisting of sulphur, oxygen (where oxygen atoms must not be immediately adjacent) and nitrogen, and/or at least one carbonyl group; or $R^{14}$ and $R^{15}$ together with the nitrogen atom to which they are bonded is a radical

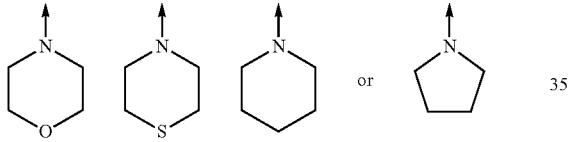

(in which the arrow in each case marks the bonds to the carbon atom in the (N) radical).

4. The compound according to claim 1, or a salt or N-oxide thereof, in which $A^1$ is hydrogen, halogen or cyano,
$A^2$ is hydrogen,
$R^1$ is hydrogen or $C_1$-$C_4$-alkyl,
X is oxygen,
n is 2,
$R^2$ is in each case hydrogen, $C_1$-$C_4$-alkyl, $C_2$-$C_4$-alkynyl, cyano-$C_1$-$C_4$alkyl or $C_1$-$C_4$-alkoxy-$C_1$-$C_4$-alkyl, optionally halogen-substituted $C_1$-$C_4$-alkylcarbonyl or $C_1$-$C_4$-alkylsulphonyl, in each case optionally halogen-substituted $C_1$-$C_4$-alkoxycarbonyl, optionally halogen-, $C_1$-$C_4$-alkyl-, $C_1$-$C_4$-haloalkyl- or cyano-substituted $C_3$-$C_6$-cycloalkylcarbonyl, or a mono- or divalent metal ion or an optionally $C_1$-$C_4$-alkyl- or aryl-$C_1$-$C_4$-alkyl-substituted ammonium ion,
$R^5$ is in each case optionally halogen-, $C_1$-$C_4$-alkoxy-, $C_1$-$C_4$-haloalkoxy-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- or $C_1$-$C_4$-haloalkylsulphonyl-substituted $C_1$-$C_4$-alkyl, $C_2$-$C_4$-alkenyl or $C_2$-$C_4$-alkynyl, in each case optionally halogen-, $C_1$-$C_4$-alkyl-, $C_1$-$C_4$-haloalkyl-, $C_1$-$C_4$-alkoxy-, or $C_1$-$C_4$-haloalkoxy-substituted $C_3$-$C_6$-cycloalkyl, $C_3$-$C_6$-cycloalkyl-$C_1$-$C_4$-alkyl or $C_3$-$C_4$-cycloalkenyl, in which the rings may contain at least one heteroatom selected from the group consisting of sulphur, oxygen (where oxygen atoms must not be immediately adjacent) and nitrogen, or
is in each case a radical

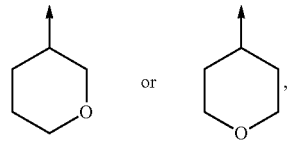

where the arrow in each case marks the bond to the carbon atom in the radical (L), or
is in each case optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkenyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl or heteroaryl-$C_1$-$C_4$-alkyl, or NR'R" in which R' and R" are each independently hydrogen or $C_1$-$C_4$-alkyl, and $R^7$ is in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- or $C_1$-$C_4$-haloalkylsulphonyl-substituted $C_1$-$C_4$-alkyl, $C_2$-$C_4$-alkenyl or $C_2$-$C_4$-alkynyl, in each case optionally halogen-, $C_1$-$C_4$-alkyl-, $C_1$-$C_4$-haloalkyl-, $C_1$-$C_4$-alkoxy-, or $C_1$-$C_4$-haloalkoxy-substituted $C_3$-$C_6$-cycloalkyl, $C_3$-$C_6$-cycloalkyl-$C_1$-$C_4$-alkyl or $C_3$-$C_4$-cycloalkenyl, in which the rings may contain at least one heteroatom selected from the group consisting of sulphur, oxygen (where oxygen atoms must not be immediately adjacent) and nitrogen, or
is in each case a radical

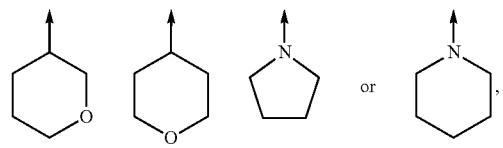

where the arrow in each case marks the bond to the sulphur atom in the radical (E), or
is in each case optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-

$C_4$-alkyl or heteroaryl-$C_1$-$C_4$-alkyl, or NR'R" in which R' and R" are each independently a radical selected from the group consisting of hydrogen, $C_1$-$C_4$-alkyl and $C_3$-$C_6$-cycloalkyl-$C_1$-$C_4$-alkyl, $R^{13}$ is a radical selected from the group consisting of hydrogen, $C_1$-$C_4$-alkyl, $C_1$-$C_4$-haloalkyl, cyano, $C_1$-$C_4$-cyanoalkyl, $C_1$-$C_4$-hydroxyalkyl, hydroxyl, $C_1$-$C_4$-alkoxy, $C_1$-$C_4$-alkoxy-$C_1$-$C_4$-alkyl, $C_1$-$C_4$-alkylthio-$C_1$-$C_4$-alkyl, $C_2$-$C_4$-alkenyl, $C_2$-$C_4$-haloalkenyl, $C_2$-$C_4$-cyanoalkenyl, $C_2$-$C_4$-alkynyl, $C_2$-$C_4$-haloalkynyl, $C_2$-$C_4$-cyanoalkynyl, $C_1$-$C_5$-alkylcarbonyl and $C_1$-$C_5$-alkoxycarbonyl, $Y^3$ is a radical selected from the group consisting of $C_1$-$C_4$-alkoxy, $C_1$-$C_4$-haloalkoxy, $C_1$-$C_4$-alkylthio, $C_1$-$C_4$-haloalkylthio and $NR^{14}R^{15}$ where $R^{14}$ and $R^{15}$ are each independently a radical selected from the group of hydrogen, $C_1$-$C_4$-alkyl, $C_3$-$C_6$-cycloalkyl, $C_3$-$C_6$-cycloalkyl-$C_1$-$C_4$-alkyl, $C_1$-$C_4$-haloalkyl, cyano, $C_1$-$C_4$-cyanoalkyl, hydroxyl $C_1$-$C_4$-alkoxy, $C_1$-$C_4$-haloalkoxy, $C_1$-$C_4$-hydroxyalkyl, $C_1$-$C_4$-alkoxy-$C_1$-$C_4$-alkyl $C_1$-$C_4$-alkylthio-$C_1$-$C_4$-alkyl, $C_2$-$C_4$-alkenyl, $C_2$-$C_4$-haloalkenyl, $C_2$-$C_4$-cyanoalkenyl, $C_2$-$C_4$-alkynyl, $C_2$-$C_4$-haloalkynyl, $C_2$-$C_4$-cyanoalkynyl, $C_1$-$C_5$-alkylcarbonyl and $C_1$-$C_5$-alkoxycarbonyl, or $R^{14}$ and $R^{15}$ together with the nitrogen atom to which they are bonded form an optionally halogen-, cyano-, $C_1$-$C_4$-alkyl-, $C_1$-$C_4$-haloalkyl-, $C_1$-$C_4$-alkoxy-, $C_3$-$C_6$-cycloalkyl- or $C_1$-$C_4$-thioalkyl-substituted saturated or unsaturated five- to six-membered ring which may contain a further atom selected from the group consisting of sulphur, oxygen and nitrogen, and/or a carbonyl group; or $R^{14}$ and $R^{15}$ together with the nitrogen atom to which they are bonded is a radical

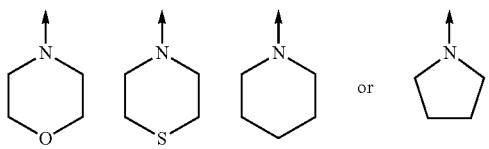

(in which the arrow in each case marks the bond to the carbon atom in the (N) radical).

5. The compound according to claim 1, or a salt or N-oxide thereof,
in which
$A^1$ is hydrogen, fluorine or chlorine,
$A^2$ is hydrogen,
$R^1$ is hydrogen or methyl,
X is oxygen,
is 2,
$R^2$ is hydrogen, methyl, ethyl, $CH_2OCH_3$, $CH_2OCH_2CH_3$, $COCH_3$, $COCH_2CH_3$, $CH_2CN$, propynyl, cyclopropyl, $Na^+$, $K^+$ or $^+N(CH_3)_4$,
$R^5$ is methyl, ethyl, i-propyl, $CF_3$, $CHF_2$, $CH_2F$, $CH_2CF_3$, cyclopropyl, dimethylammo, diethylamino, phenyl or benzyl, and
$R^7$ is methyl, ethyl, i-propyl, $CF_3$, $CHF_2$, $CH_2F$, $CH_2CF_3$, cyclopropyl, dimethylamino, diethylamino, phenyl and benzyl.

6. The compound according to claim 1, or a salt or N-oxide thereof,
in which
$A^1$ is hydrogen, fluorine or chlorine,
$A^2$ is hydrogen,
$R^1$ is hydrogen or methyl, and
$G^3$ and $G^4$ form a bicycle group

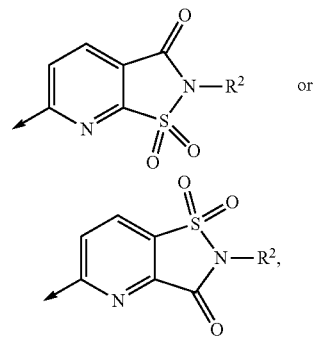

in which the arrow marks the bond to the adjacent ring.

7. The compound according to claim 2, or a salt or N-oxide thereof,
in which
$G^1$ is C—F,
$R^1$ is hydrogen, and
$G^4$ is the radical (E),

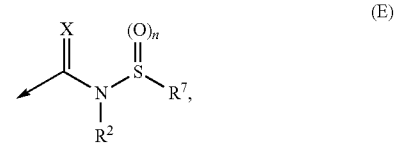

(E)

in which the arrow marks the bond to the adjacent ring, wherein $R^2$ and $R^7$ are as defined in claim 2.

8. A compound according to claim 1 which is:

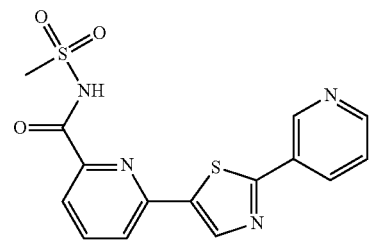 [SMILES: CS(=O)(=O)NC(=O)c1cccc(-c2cnc(-c3cccnc3)s2)n1]

9. A composition comprising at least one compound of the formula (I) or a salt or N-oxide thereof according to claims 1 or 2, and a carrier.

10. A method for controlling pests, comprising allowing at least one compound of formula (I) or a salt or N-oxide thereof according to claim 1 or 2, to act on the pests and/or their habitat.

11. A method for controlling pests, comprising allowing a composition according to claim 9, to act on the pests and/or their habitat.

* * * * *